US010776533B2

(12) United States Patent
Fisker et al.

(10) Patent No.: US 10,776,533 B2
(45) Date of Patent: Sep. 15, 2020

(54) 3D MODELING OF A DENTAL RESTORATION USING TEXTURAL FEATURES

(75) Inventors: Rune Fisker, Virum (DK); Tais Clausen, Klagshamn (SE); Nikolaj Deichmann, Klagshamn (SE); Mikkel Bille Stegmann, Vanløse (DK); Karl-Josef Hollenbeck, Copenhagen Ø (DK); Thomas Højgaard Allin, Espergærde (DK); Lars Schjøth, Copenhagen SV (DK)

(73) Assignee: 3SHAPE A/S, Copenhagen K (DK)

( * ) Notice: Subject to any disclaimer, the term of this patent is extended or adjusted under 35 U.S.C. 154(b) by 970 days.

(21) Appl. No.: 13/809,797

(22) PCT Filed: Jul. 11, 2011

(86) PCT No.: PCT/DK2011/050273
§ 371 (c)(1),
(2), (4) Date: May 7, 2013

(87) PCT Pub. No.: WO2012/007003
PCT Pub. Date: Jan. 19, 2012

(65) Prior Publication Data
US 2013/0218531 A1 Aug. 22, 2013

Related U.S. Application Data

(60) Provisional application No. 61/363,735, filed on Jul. 13, 2010.

(30) Foreign Application Priority Data

Jul. 12, 2010 (DK) .................................. 2010 00617

(51) Int. Cl.
*G06F 17/50* (2006.01)
*A61C 5/77* (2017.01)
(Continued)

(52) U.S. Cl.
CPC ................ *G06F 30/20* (2020.01); *A61C 5/77* (2017.02); *A61C 9/004* (2013.01); *A61C 9/0053* (2013.01);
(Continued)

(58) Field of Classification Search
CPC ... A61C 13/0004; A61C 9/004; A61C 9/0053; A61C 5/77; G06F 17/5009; B33Y 50/00; B33Y 80/00; G16H 20/40
See application file for complete search history.

(56) References Cited

U.S. PATENT DOCUMENTS 6,744,914 B1 6/2004 Rubbert et al.
7,156,655 B2 * 1/2007 Sachdeva ................. A61C 7/00
433/213
(Continued)

FOREIGN PATENT DOCUMENTS

CN 101686853 A 3/2010
JP 2009-216485 A 9/2009
(Continued)

OTHER PUBLICATIONS

Tomatis, Stefano, Mauro Carrara, Aldo Bono, Cesare Bartoli, Manuela Lualdi, Gabrina Tragni, Ambrogio Colombo, and Renato Marchesini. "Automated melanoma detection with a novel multispectral imaging system: results of a prospective study." Physics in medicine and biology 50, No. 8 (2005): 1675.*
(Continued)

*Primary Examiner* — Aniss Chad
(74) *Attorney, Agent, or Firm* — Buchanan Ingersoll & Rooney PC

(57) ABSTRACT

3D modeling of an object using textural features. Disclosed is a method and a system for 3D modeling of a 3D object adapted to be inserted in or worn by a patient. The 3D modeling applies information of one or more features from (Continued)

an acquired 2D digital representation including textural data of the location where the 3D object is adapted to be arranged.

22 Claims, 28 Drawing Sheets

(51) Int. Cl.
| | |
|---|---|
| G06F 30/20 | (2020.01) |
| A61C 13/00 | (2006.01) |
| A61C 9/00 | (2006.01) |
| B33Y 50/00 | (2015.01) |
| B33Y 80/00 | (2015.01) |
| G16H 20/40 | (2018.01) |

(52) U.S. Cl.
CPC ........... *A61C 13/0004* (2013.01); *B33Y 50/00* (2014.12); *B33Y 80/00* (2014.12); *G16H 20/40* (2018.01)

(56) References Cited

U.S. PATENT DOCUMENTS

| | | | |
|---|---|---|---|
| 7,234,934 B2 | 6/2007 | Rosenberg | |
| 7,234,937 B2 | 6/2007 | Sachdeva et al. | |
| 8,257,083 B2 * | 9/2012 | Berckmans, III | A61C 8/0001 433/213 |
| 8,706,672 B2 * | 4/2014 | Malfliet | A61B 6/5247 264/16 |
| 2002/0180760 A1 | 12/2002 | Rubbert et al. | |
| 2004/0015327 A1 | 1/2004 | Sachdeva et al. | |
| 2004/0107080 A1 | 6/2004 | Deichmann et al. | |
| 2004/0197727 A1 | 10/2004 | Sachdeva et al. | |
| 2006/0115793 A1 | 6/2006 | Kopelman et al. | |
| 2007/0262983 A1 | 11/2007 | Wonchool | |
| 2008/0024768 A1 | 1/2008 | Babayoff | |
| 2008/0057478 A1 | 3/2008 | Choi | |
| 2009/0133260 A1 | 5/2009 | Durbin et al. | |
| 2009/0187393 A1 * | 7/2009 | Van Lierde | A61C 1/084 703/11 |
| 2009/0316966 A1 | 12/2009 | Marshall et al. | |
| 2010/0124731 A1 * | 5/2010 | Groscurth | A61C 9/00 433/213 |
| 2010/0145898 A1 | 6/2010 | Malfliet et al. | |
| 2013/0158958 A1 * | 6/2013 | Methot | A61C 13/0004 703/1 |
| 2013/0295518 A1 * | 11/2013 | Parker | A61B 1/00048 433/29 |

FOREIGN PATENT DOCUMENTS

| | | |
|---|---|---|
| JP | 2009-271650 A | 11/2009 |
| JP | 2010-134382 A | 6/2010 |
| JP | 2010-524529 A | 7/2010 |
| WO | WO 00/19935 A1 | 4/2000 |
| WO | WO 2006/065955 A2 | 6/2006 |
| WO | WO 2008/028058 A2 | 3/2008 |
| WO | 2008/083857 A1 | 7/2008 |
| WO | WO 2008/128700 A1 | 10/2008 |
| WO | 2009/006273 A2 | 1/2009 |
| WO | 2009/006303 A2 | 1/2009 |
| WO | 2012/000511 A1 | 1/2012 |

OTHER PUBLICATIONS

Manual for SpectroShade Version 2.30 / 2.31—MHT Optic Research AG, Dec. 2006.*

English Translation of the Office Action (Notice of Reasons for Rejection) dated Jun. 23, 2015, by the Japanese Patent Office in corresponding Japanese Patent Application No. 2013-518955. (11 pages).

Search Report dated Feb. 18, 2011, by the Danish Patent Office for Application No. PA 2010 00617.

International Search Report (PCT/ISA/210) dated Sep. 14, 2011, by the Dannish Patent Office as the International Searching Authority for International Application No. PCT/DK2011/050273.

English translation of Office Action (Notice of Reasons for Rejection) dated Mar. 8, 2016, by the Japanese Patent Office in corresponding Japanese Patent Application No. 2013-518955. (6 pages).

Office Action (Notice of Reasons for Rejection) dated Mar. 7, 2017, by the Japanese Patent Office in corresponding Japanese Patent Application No. 2013-518955, and an English Translation of the Office Action. (16 pages).

Office Action (Notification of Reason for Refusal) dated Apr. 19, 2017, by the Korean Intellectual Property Office in corresponding Korean Patent Application No. 10-2013-7003585, and an English Translation of the Office Action. (13 pages).

The extended European search report dated Apr. 30, 2020, by the European Patent Office in corresponding European Patent Application No. 19214718.9. (9 pages).

* cited by examiner

3D MODELING OF A DENTAL RESTORATION USING TEXTURAL FEATURES

This invention generally relates to a method for 3D modeling of an object adapted to be inserted in a cavity of a patient or worn by a patient. More particularly, the invention relates to acquiring digital representations of at least a part of the location where the object is adapted to be arranged.

Designing and modeling of teeth are known in the field of dental restorations. When a patient requires a dental restoration, such as crowns, bridges, abutments, or implants, the dentist will prepare the teeth e.g. a damaged tooth is grinded down to make a preparation where a crown is glued onto. An alternative treatment is to insert implants, such as titanium screws, into the jaw of the patient and mount crowns or bridges on the implants. After preparing the teeth or inserting an implant, the dentist can make an impression of the upper jaw, the lower jaw and a bite registration or a single impression in a double-sided tray, also known as triple trays. The impressions are sent to the dental technicians who manufacture the restorations e.g. the bridge. The first step to manufacture the restoration is traditionally to cast the upper and lower dental models from impressions of the upper and the lower jaw, respectively. The models are usually made of gypsum and often aligned in a dental articulator using the bite registration to simulate the real bite and chewing motion. The dental technician builds up the dental restoration inside the articulator to ensure a nice visual appearance and bite functionality.

CAD technology for manufacturing dental restorations is rapidly expanding improving quality, reducing cost and facilitating the possibility to manufacture in attractive materials otherwise not available. The first step in the CAD manufacturing process is to create a 3-dimensional model of the patient's teeth. This is traditionally done by 3D scanning one or both of the dental gypsum models. The 3-dimensional replicas of the teeth are imported into a CAD program, where the entire dental restoration, such as a bridge substructure, is designed. The final restoration 3D design is then manufactured e.g. using a milling machine, 3D printer, rapid prototyping manufacturing or other manufacturing equipment. Accuracy requirements for the dental restorations are very high otherwise the dental restoration will not be visual appealing, fit onto the teeth, could cause pain or cause infections.

WO0019935A discloses a computer-implemented method for use in creating a digital model of an individual component of a patient's dentition, the method comprising: (a) receiving a data set that forms a three-dimensional (3D) representation of the patient's dentition; (b) applying a computer-implemented test to the data set to identify data elements that represent portions of an individual component of the patient's dentition; and (c) creating a digital model of the individual component based upon the identified data elements.

U.S. Pat. No. 7,234,937B relates to a system for use in diagnosis and planning treatment of a human patient and comprises: a general purpose computer system having a processor and a user interface; a memory accessible to said general purpose computer system storing a) a first set of digital data representing patient craniofacial image information obtained from a first imaging device, and b) a second set of digital data representing patient craniofacial image information obtained from a second image device different from said first image device, said first and second sets of data representing at least in part common craniofacial anatomical structures of said patient, at least one of said first and second sets of digital data including data representing the external visual appearance or surface configuration of the face of the patient, wherein said first and second digital data sets are each obtained at different points in time and are not captured in a correlated fashion; and a set of computer instructions stored on a machine readable storage medium accessible to said general purpose computer system, wherein said set of instructions comprises instructions for causing said general computer system to: 1) automatically, and/or with the aid of operator interaction, superimpose said first set of digital data and said second set of digital data so as to provide a composite, combined digital representation of said craniofacial anatomical structures created from said first and second digital data sets each obtained at different points in time and not captured in a correlated fashion in a common coordinate system; wherein said set of instructions comprise instructions for creating a virtual 3D face at least from a portion of said craniofacial anatomical structures using an active model matching strategy; 2) display said composite, combined digital representation of said craniofacial anatomical structures, including said virtual 3D face, to a user of said system.

US2009133260A discloses systems and methods to fabricate a restorative prosthesis. The system includes a scanner to intra orally capture color and translucency information along with a three dimensional (3D) shape of the dentition being reconstructed. The system also includes a computer aided design (CAD) module to receive the color and translucency information and the 3D shape to render a color accurate representation of the prosthesis for review, wherein the color, translucency and surface information is combined in a single digital prescription which is electronically transferred to a laboratory or CAD/CAM system for fabrication. The system provides the capability for 3D shape, color and translucency characteristics of the final prosthesis to be measured and quantitatively compared to the prescribed requirements.

However, it remains a problem to improve and expand the use of geometrical data and textural data for patient related technology.

Disclosed is a method for 3D modeling of a 3D object adapted to be inserted in or worn by a patient, wherein the method comprises:
  acquiring a 3D digital representation of at least a part of the location where the 3D object is adapted to be arranged, where the 3D digital representation comprises geometrical data of the location;
  acquiring a 2D digital representation of at least a part of the location where the object is adapted to be arranged, where the 2D digital representation comprises textural data relating to one or more features of the location;
  where a desired coverage of the location is obtained by acquiring each of the 2D digital representation comprising textural data and the 3D digital representation comprising geometrical data from one or more different viewpoints relative to the location;
  aligning the 2D digital representation comprising textural data and the 3D digital representation comprising geometrical data;
  combining at least a part of the 2D digital representation comprising textural data and the 3D digital representation comprising geometrical data to obtain a combined 3D digital representation comprising both geometrical data and textural data of the location;

visualizing the combined 3D representation comprising the geometrical data and the textural data of the location; and 3D modeling the 3D object such that the modeled 3D object is adapted to be inserted in or worn by a patient, where said 3D modeling applies information of the one or more features from the acquired 2D digital representation comprising textural data.

Disclosed is a method for 3D modeling of a 3D object adapted to be inserted in or worn by a patient, wherein the method comprises the steps of:

acquiring a 3D digital representation of at least a part of the location where the object is adapted to be arranged, where the 3D digital representation comprises geometrical data of the location;

acquiring a 2D digital representation of at least a part of the location where the object is adapted to be arranged, where the 2D digital representation comprises textural data of the location;

where the acquisition of the 2D digital representation comprising textural data and 3D digital representation comprising geometrical data is performed by repositioning the location and acquisition means relative to each other for obtaining a desired coverage of the location;

aligning and combining at least part of the 2D digital representation comprising textural data and the 3D digital representation comprising geometrical data to obtain a combined 3D digital representation comprising both geometrical data and textural data of the location;

visualizing the combined 3D representation comprising the geometrical data and the textural data of the location; and applying information of one or more features from the 2D digital representation comprising textural data of the location, when modeling the 3D object.

In some embodiments, the location is automatically repositioned relative to an acquisition unit during the acquisition of the 2D digital representation comprising textural data and during the acquisition of the 3D digital representation comprising geometrical data, such that at least one of the digital representations is acquired automatically from a number of different viewpoints and the desired coverage is obtained.

Disclosed is a method for 3D modeling of a 3D object adapted to be inserted in or worn by a patient, wherein the method comprises:

acquiring a 3D digital representation of at least a part of the location where the 3D object is adapted to be arranged, where the 3D digital representation comprises geometrical data of the location;

acquiring a 2D digital representation of at least a part of the location where the object is adapted to be arranged, where the 2D digital representation comprises textural data relating to one or more features of the location;

where a desired coverage of the location is obtained by acquiring each of the 2D digital representation comprising textural data and the 3D digital representation comprising geometrical data from one or more different viewpoints relative to the location;

aligning the 2D digital representation comprising textural data and the 3D digital representation comprising geometrical data; and 3D modeling the 3D object such that the modeled 3D object is adapted to be inserted in or worn by a patient, where said 3D modeling applies information of the one or more features from the acquired 2D digital representation comprising textural data.

In some embodiments, at least a part of the 2D digital representation comprising textural data and the 3D digital representation comprising geometrical data are combined to obtain a combined 3D digital representation comprising both geometrical data and textural data of the location, and where the method comprises visualizing the combined 3D representation comprising the geometrical data and the textural data of the location.

Disclosed is a system for 3D modeling of a 3D object adapted to be inserted in or worn by a patient, wherein the system comprises:

an illumination unit configured for illuminating at least part of a scan volume of the system;

an acquisition unit configured for acquiring a 2D digital representation comprising textural data and a 3D digital representation comprising geometrical data of a location arranged in the scan volume;

a first digital signal processor unit configured for:
analyzing the acquired 2D digital representations and 3D digital representations,
aligning the 2D digital representation and the 3D digital representation; and
combining at least part of the 2D digital representation and the 3D digital representation to obtain a combined 3D digital representation comprising both geometrical data and textural data of the location;

a visualization device for visualizing the combined 3D representation comprising the geometrical data and the textural data of the location; and a second digital signal processor unit configured for 3D modeling the 3D object such that the modeled 3D object is adapted to be inserted in or worn by a patient, where said 3D modeling comprises applying information from the acquired 2D digital representation.

In the context of the present invention, the phrase "scan volume" may refer to the volume in which a location can be illuminated with light from the light source(s) and light reflected from the location can be received by the cameras, such that the 2D digital representation and the 3D digital representation can be acquired of a location arranged in the scan volume.

In the context of the present invention, the phrase "applying information of one or more features from the 2D digital representation" may refer to case where the 2D digital representation provides the information of the one or more features.

The feature may be part of the location or defined on the location, a physical model or an impression of the location, and the acquired 2D digital representation comprising textural data may provide the information of the one or more features. In the context of the present invention, the phrases "object" and "3D object" may be used interchangeably.

In the context of the present invention, the phrases "modeling" and "3D modeling" may be used interchangeably.

A feature having a geometry that allows the feature to be identified in a digital representation of the location may be referred to as a geometrical feature.

A feature having a texture that allows the feature to be identified in a digital representation of the location may be referred to as a textural feature.

A feature may have a both a geometry and a texture. A feature may thus both be referred to as a geometrical feature and an textural feature when the feature has both a geometry and a texture that allows the feature to be identified in a digital representation of the location.

The location may be the part or at the part of the patients body where the 3D object adapted to be inserted in or worn by the patient In the context of the present invention, the phrase "a feature of the location" may refer to situations where the feature is an integrated part of the location, such as e.g. the margin line of a tooth prepared for a restoration, to situations where the feature is defined directly on the location, such e.g. a part of an orthodontic appliance or a line drawn on a patients teeth by a dental technician, or situations where the feature is defined on a physical model or an impression of the location, such as a line drawn on a gypsom model of a set of teeth.

The phrase "the location" may refer to the location itself, a physical model of the location or an impression of the location. For example may the phrase "acquiring a 2D digital representation of the location" refer to the situation where a 2D digital representation is acquired of the location, of a physical model of the location, or of an impression of the location.

The phrase "textural data of the location" may accordingly refer to situations where the feature having a texture is an integrated part of the location, and where the features is defined by e.g. a dental technician directly on the location or on a physical model or an impression of the location. For example, one feature may be a colored line drawn on a physical model of a set of teeth, where the feature is a boundary of a removable partial denture, and the texture of the feature is the color in which the boundary is defined. The feature is hence not an integrated part of the location, i.e. the patients mouth, but is defined later on the physical model. In the context of the present invention, the drawn line may still be considered to be a feature of the location.

The 2D digital representation comprising textural data of the location may comprise one or more 2D images of the location or of a physical model or an impression of the location. The one or more 2D images may be acquired from the same or from different viewpoints relative to the location.

The 2D digital representation comprising textural data may be acquired from the same viewpoints as the 3D digital representation comprising geometrical data. This may allow for a relatively straight forward alignment of the 2D digital representation and the 3D digital representation.

The 2D digital representation comprising textural data may be acquired from viewpoints that are not the same as the viewpoints from which the 3D digital representation comprising geometrical data is acquired.

A 2D image comprising data relating to the texture of the location may be referred to as a textural image or a texture image.

Consequently, it is an advantage that features from the 2D digital representation comprising textural data of a location can be used for facilitating 3D modeling of an object which is adapted to be arranged in that location. When using textural data of the location when modeling the object, the result of the modeling may be improved because different types of data are used, whereby different types of features of the location can be detected and accounted for in the modeling process of the object.

Texture is defined as the feel, shape, and look of the surface of the location, thus texture may comprise the smoothness, roughness, softness, color etc. of the location. Texture can refer to the properties held and sensations caused by the external surface of the location received through the sense of touch. Texture can also be used to describe the feel of non-tactile sensations. Texture can comprise a pattern, color or other visual properties of the surface of the location. Thus textural data is data describing the texture of the surface of the location.

Geometry is defined as the size, shape, relative position of features, and the properties of space, and does therefore concern lengths, areas and volumes of the location. Thus geometrical data is data describing the geometry of the surface of the location.

The 2D digital representation comprising textural data and the 3D digital representation comprising geometrical data of the location can be acquired from any viewpoint by means of repositioning the location and acquisition means, such as light source and camera used for acquiring the digital representations, relative to each other. The repositioning may be performed automatically using at least a two-axis motion system in e.g. a scanner. Thus the scanner may comprise a two-axis or three-axis motion system adapted to perform acquisition automatically of the digital representations of the location from any viewpoint.

Thus it may be an advantage that the same motion system is used for repositioning the location for acquisition of both geometrical and textural data. The motion system may be arranged in a 3D scanner into which a model or an impression to be scanned is placed. The motion system may perform translational and/or rotational movement of the model or impression or of the acquisition means, i.e. the light source and/or the camera for acquiring the 2D digital representation comprising textural data and the 3D digital representation comprising geometrical data. Thus the repositioning may be of the location for which data are being captured, e.g. the model or impression, and/or the repositioning may be of the acquisition means, light source(s) and camera. When having two or three axes in the motion system, the model or impression can be scanned both from the sides and from the top.

A desired coverage of the location may be full coverage of the entire location or of part of the location, or just coverage of a specific area of the location. A desired coverage may be obtained by capturing e.g. three or four textural images, which can then be assembled into a composite textural image. More or less textural images may be captured for obtaining a desired coverage.

The aligning and the combining may describe how the two digital representations, the 3D digital representations comprising geometrical data and the 2D digital representations comprising textural data of the location, are processed in order to obtain a combined 3D digital representation comprising the geometrical and the textural data.

Alignment may be defined as the adjustment of a digital representation of a location in relation with another digital representation of the location, such that structures of the digital representations are coinciding. Thus common or alike structures of the 3D digital representation comprising geometrical data of the location and the 2D digital representation comprising textural data of the location are aligned.

Aligning and combining the representations may improve the visualization and the precision of feature detection.

In the context of the present invention, the phrase "visualizing the combined 3D representation" may refer to a visualization of all data provided by the combined 3D representation or to a visualization of a part of the data provided by the combined 3D representation. The visualized combined 3D representation may hence provide a visualization of the extracted information rather than all the data which can be provided from the 2D digital representation.

Applying the information of the one or more textural features of the location, when modeling the object, can be defined as that when modeling the object which is adapted to be inserted, worn or arranged in the location, the information of the textural features of the location is used such that the object fits into the location taking account of the textural features of the location. Fitting of the object may mean that the insertion or wearing of the object does not cause pain for the patient, and that the insertion or wear of the object is esthetically pleasing.

Within dentistry, modeling of an object may comprise modeling of one or more dental restorations or restoration substructures, modeling of one or more implants or implant abutments, modeling orthodontic appliances or modeling orthodontic movement of one or more teeth, modeling a denture, e.g. a full or partial fixed or removable partial denture, or modeling one or more teeth in a denture.

Thus the modeling may comprise modeling of restorations, orthodontic appliances, implants, dentures etc. When the 3D computer-aided design (CAD) modeling comprises for example restorations, the virtually modeled restorations, such as crowns and bridges, can be manufactured by means of computer-aided manufacturing (CAM), and the manufactured restorations or appliance can then eventually be inserted into the patient's mouth by a dentist.

The step of applying the information of the one or more features of the location when modeling the object and other steps of the method may be performed digitally on a computer and shown on a user interface such as a screen, such that the user or operator obtains a visual representation of the data sets and the different operations performed on the data sets, and the operator can then perform, finalize or check the modeling of the object.

The method may comprise manufacturing of the modeled 3D object and/or treatment planning of the location using one or more objects manufactured by means of the method.

Disclosed is also a method of manufacturing a 3D object adapted to be inserted in or worn by a patient, where the method of manufacturing comprises the steps of the method for 3D modeling of the 3D object and a step of manufacturing the modeled 3D object.

As an alternative to the wording acquiring a digital representation of at least a part of the location where the object is adapted to be arranged, the method may comprise acquiring a digital representation of the location where the object is adapted to be arranged.

The 3D digital representation of the location and the 3D model of the 3D object may be by a triangular-based representation, where 3D surface are parameterized by a number of vertices, which are connected by triangles.

Thus the geometrical scans are surface scans providing a surface representation. When modeling the object for fitting into the location, it is thus the surface of the object which is being modeled, or the modeling is performed on the surface of the object or outside the surface of the object. For performing modeling outside the surface, an offset of the surface may be made digitally. In the offset a copy of the surface is placed a distance from the surface, such that modeling can be performed on a shape similar to the surface shape, but without modeling the object surface itself.

In e.g. CT scans, a volume is scanned and thus a volumetric representation and not a surface representation is made.

WO0019935 described above discloses a method of obtaining data sets that forms 3D representations of the patient's dentition and to identify data elements representing individual components, where the individual component can be an individual tooth or gum tissue. Thus that method is concerned with 3D representations for identifying e.g. a individual tooth and thus not concerned with the detection of features of the tooth, e.g. detected from a 2D representation. The method is used for creating orthodontic appliances to implement a treatment plan.

U.S. Pat. No. 7,234,937 described above discloses a system for storing and combining different data representations of craniofacial image information of a patient including external visual appearance or surface configuration of the face of the patient for creating a virtual 3D face. Thus this document relates to craniofacial image information, and the document does for example not disclose using information of features or modeling of an object.

In US2009133260A also described above, the color and translucency information and the 3D shape is used to render a color accurate representation of the prosthesis for review, such that the user can review whether the color of the prosthesis is correct.

US2004107080 relates to manufacture of ear pieces and discloses a method for computer-assisted modelling of customised earpieces comprising at least one part being individually matched to an auditory canal and/or a meatus, where the method comprises a number of steps including the step of: a) obtaining a three-dimensional computer model, 3D-model, of the location, i.e. of at least part of the auditory canal, where the 3D-model of the location has an outer surface. The document also discloses that in some embodiments an impression of the ear or auditory canal, which is used to generate the 3D digital representation of the canal, is scanned such that a texture scan, including a colour scan, is provided. Furthermore, in some embodiments texture marked on the impression is used for initial arrangement, and in some embodiments the method comprises assigning colours and/or texturing to the surface of the shell. US2004107080 does for example not disclose that the acquisition of the 2D digital representation comprising textural data and 3D digital representation comprising geometrical data are performed by automatically repositioning the location and acquisition means relative to each other for obtaining a desired coverage of the location. Furthermore, the document does not disclose a combined and aligned 3D digital representation.

In some embodiment, the method comprises extracting the information of the one or more features from the 2D digital representation comprising textural data.

Thus information of the one or more features may be extracted before applying the information of the features, when modeling the 3D object.

In some embodiments extracting the information of the one or more features is performed automatically.

Automatically extracting information of one or more features of the location may be defined as that one or more of the features of the location is automatically detected from the 2D digital representation comprising textural data.

The information may be extracted from features that are defined using a rather complex pattern on the location. A feature may for example be defined using a closed loop to mark the edges of the feature and number of intersecting lines arranged to form a grid within this edge. A feature may also be defined using a line comprising a number of disjunct line segments. For a line comprising a number of disjunct line segments, the full line may be formed by joining the line segments. This may be realized by estimating the gradients of neighboring line segment at the ends facing each other. When the gradient vectors are substantially parallel, the two line segments are possibly sections of the same line, and can hence be virtually joined. When a number of intersecting lines form a grid, the gradients of the line segments between the intersections may be determined and the evaluation of the relative arrangement of the lines in the intersections may comprise identifying the different parts of the intersection from the gradient of the lines between the intersections.

Alternatively, the extraction of information of the one or more features is performed manually by the operator.

In some embodiments the method comprises translating one ore more 2D features from the 2D digital representation comprising textural data into 3D features.

It may be an advantage that features from the 2D digital representation can be transformed into 3D features, since hereby the information from the 2D digital representation can be applied in the 3D modeling of the 3D object. The one or more 2D features may comprise a 2D point, a 2D curve or a 2D spline. The 3D feature may comprise comprises a 3D point, a 3D curve or a 3D spline, such as a 3D spline extracted from the textural data of the 2D digital representation.

In the context of the present invention, the phrase "a 2D feature" may refer to the shape of a feature of the location as captured in one 2D image of the 2D digital representation comprising textural data. Each of these 2D images may comprise part of the information of the feature and this part may be extracted as said 2D feature. The combining may comprise projecting the 2D features from one or more 2D images onto the 3D digital representation. The 2D features may be translated into 3D features based on a combined 3D digital representation, where the combined 3D digital representation may comprise the 3D digital representation onto which the 2D features from one or more 2D images of the 2D digital representation are projected. The information of the 2D digital representation may be the 3D feature, such that the 3D modeling applies the 3D feature.

In some embodiments combining the 2D digital representation and the 3D digital representation to obtain a combined 3D digital representation comprises projecting extracted information from the 2D digital representation onto the 3D digital representation.

Thus combining the two representations may comprise projecting one of the representations onto the other representation, for example projecting the 2D digital representation comprising textural data of the location onto the 3D digital representation comprising geometrical data of the location.

A system for acquiring the 3D digital representation comprising geometrical data and the 2D digital representation comprising textural data may comprise several components such as one or more illumination units, acquisition units, and a positioning unit for translation and/or rotation the location relative to the illumination and acquisition units. A straightforward projection of a part of the 2D digital representation onto the 3D digital representation of the location formed from said 3D digital representation is possible when detailed knowledge of the arrangement of the location and the units of the system is available. In some embodiments, the system is thoroughly characterized to provide this knowledge and the relative arrangement of e.g. the positioning units, the light sources of the illumination unit and the cameras of the acquisition unit is hence known for each acquired digital representation or part of a digital representation. The relative positions of the acquisition units and the location can thus be identified for each acquired part of the 2D digital representation and the acquired 2D digital representation or the parts of the 2D digital representation can straightforward be projected onto the 3D digital.

One way of proving a precise projection of 2D digital representations of the 3D digital representation is to integrate a virtual model of the system in the software, such that the orientation of the location relative to the camera(s) used for acquiring the 2D images of the 2D digital representation is known for each acquired 2D image of the 2D digital representation. The software can then project the 2D images or parts of the 2D images of the 2D digital representation onto the 3D digital representation. The software may also be configured for implementing other steps of the method according to the present invention. Lens distortion may also be taken into account and e.g. be included in the virtual model of the system.

In some embodiments the 3D digital representation is acquired by scanning a physical model of the location, by scanning an impression of the location, and/or by performing a direct scanning of the location.

When the 2D digital representation is provided by acquiring 2D images of a physical model or an impression of the location, the feature may be defined on the physical model or an impression of the location prior to acquiring the 2D images. That is, the feature may not be part of the location but something which is added prior to the acquisition of the 2D digital representation. The feature may also be something which is added to the location prior to obtaining a physical model or impression of the location or prior to a direct acquisition of the 2D digital representation.

In the context of the present invention, the phrase "acquiring a 2D digital representation of at least a part of the location where the object is adapted to be arranged, where the 2D digital representation comprises textural data of the location" may also refer to the case where the textural data of the location are defined on a physical model or an impression of the location or directly on the location prior to a direct scanning of the location. The textural data may be defined by an operator, such as a dental technician, for example by drawing features on a physical model of the location.

In some embodiments, acquiring the 3D digital representation comprising geometrical data of the location and the 2D digital representation comprising textural data of the location is performed by means of a system adapted for acquiring geometrical data and textural data.

The system may comprise an acquisition unit configured for acquiring the digital representations of the location and a positioning unit configured for positioning the location relative to the acquisition unit, and the method comprises arranging the location, a physical model of or an impression of the location, in relation to the system. The acquisition unit and the positioning unit may be part of a 3D scanner. The acquisition unit may comprise one or more cameras adapted for acquiring both geometrical data and textural data In some embodiments, the location is automatically repositioned relative to the acquisition unit during the acquisition of the 2D digital representation comprising textural data and during the acquisition of the 3D digital representation comprising geometrical data, such that at least one of the digital representations is acquired automatically from a number of different viewpoints and the desired coverage is obtained. Both the 2D digital representation and the 3D digital representation may be acquired automatically from a number of different viewpoints In some embodiments, the positioning unit provides an automatic repositioning of the location relative to the acquisition unit.

Within dentistry, the dental technician may draw features directly on a physical model or an impression of the location, which drawn features may be denoted annotations, and where the features may be lines to be used for modeling of the object. The lines may for example be the preparation margin line for a tooth restoration, or the major connector, clasps and retention grids for a partial denture. Thus these drawn features, such as lines, may be used as the texture information.

When using direct scanning, such as intra oral scanning, the texture may be present on the teeth in the form of colors, shades, material properties etc. The feature may be a line drawn directly on the teeth or on the soft tissue of the patient's palette. For instance, when the 3D object comprises a removable partial, a preferred shape of the removable partial can be indicated on the teeth and soft tissue.

When using impression scanning the texture is present on the impression in the form of for example the fine-structure of the surface of the impression material. Within dentistry grinding a tooth or grinding a preparation line produces a more rough surface structure, where the grinding is made, and this rough structure is transferred to the impression material when making an impression of the teeth. The part of a tooth which is not grinded has a smoother surface than the rough surface of the grinding.

In some embodiments acquiring the 2D digital representation comprising textural data and the 3D digital representation comprising geometrical data of the location comprise acquiring 2D images and scanning, respectively, the location from a number of different viewpoints. Acquiring the 2D digital representation may comprise acquiring one or more 2D images of a physical model of the location or of an impression of the location, and/or by acquiring 2D images directly of the location. The 2D images may be acquired using one or more cameras.

An advantage of this is that when acquiring 2D images and scanning, respectively, the location from different viewpoints, then data for all or the relevant features of the location may be acquired. Different viewpoints may comprise different angles etc.

In some embodiments, the part of the 2D digital representation comprising textural data which is combined with the 3D digital representation comprises one or more sections of the 2D images of the acquired 2D digital representation. The one or more sections of the 2D images may be the sections that relates to the feature of the location.

In some embodiments the 3D modeling of the 3D object is performed automatically based on the one or more features.

An advantage of this embodiment is that the user does not need to perform any manual modeling of the 3D object on the user interface, when the modeling can be performed fully automatic. If an automatic modeling takes place, then the user may check that the modeling is satisfying, and maybe perform small corrections to the modeling.

In some embodiments, the 3D modeling comprises defining one or more edges of the 3D object based on the information.

The method may comprise providing a 3D model of the 3D object, and the 3D modeling may comprise adapting the provided 3D model of the 3D object based on the information. The provided 3D model may be provided from a library.

The adapting of the provided 3D model of the 3D object may comprise shaping the edges of the provided 3D model of the 3D object based on the information. This may for example be realized using computer software which allows the user to identify the information, such as said 3D spline, as the edge of the 3D object.

The automatic modeling may comprise modeling the 3D object based on the information extracted from the 2D digital representation comprising textural data of the location. The extracted information may relate to a boundary of the modeled 3D object, such as e.g. the perimeter of a restoration which is modeled to be positioned at a prepared tooth where the feature is the margin line of the prepared tooth. The extracted information may be in the form of a 2D spline following the feature on in a 2D image of the 2D digital representation or of a 3D spline following the feature on the 3D digital representation comprising geometrical data.

Once the edge of the 3D object is extracted from the 3D spline, the 3D object may be defined using standard algorithms such as algorithms that can be implemented using computer software. The 3D object or at least parts of the object may be formed using input from libraries, such as when a structure of a part is defined by input from a library and the perimeter of the part is defined by the 3D spline. This may e.g. be the case for the retention grid of a removable partial denture, where a holed structure of the surface may be provided from a library while the perimeter may be derived from a 3D spline.

In situations where the 3D object is an object used within dentistry, such as a restoration or a removable partial denture, the shape of the 3D object may partially be extracted from the 3D digital representation comprising geometrical data and partially from the 3D spline. That is the cusp or incisal edge and the labial, proximal and lingual surfaces of a tooth preparation can be extracted from the 3D digital representation comprising geometrical data while the surface of the restoration facing the margin line of the prepared tooth or abutment is extracted from the feature.

In some embodiments the 3D object is adapted to replace an anatomical object of the patient's body.

Thus the object may be an artificial hip for replacing a broken hip, or a respiratory device for replacing the respiratory tract or a part of it, or a breast prosthesis for replacing a breast which has been removed due to e.g. a malignant tumor. Thus the objects may be used as replacements if the original anatomical object is broken or attacked by a disease.

However, the object may also replace an anatomical object for pure cosmetic reasons, such as replacing or remodeling breasts, bottoms, lips, nose, face, stomach, thighs etc. using e.g. plastic surgery.

In some embodiments the 3D object is adapted to be inserted in a body cavity of the patient.

Examples of objects which are adapted to be inserted in a body cavity are hearing devices to be inserted in the ear canal, dental restorations, dental implants, orthodontic appliances etc. to be inserted in the mouth, contraceptive devices, such as a diaphragm, to be inserted in a female vagina, a glass eye to be inserted in an empty eye socket etc.

In some embodiments the location is the mouth of the patient.

In some embodiments the location is one or more teeth of the patient.

The location may be a tooth preparation prepared for a restoration such as a crown or a bridge.

In some embodiments the location is an ear canal of the patient.

In some embodiments extracting information of one or more features of the location comprises feature detection.

An advantage of this embodiment is that feature detection comprises methods that compute abstractions of image information and perform local decisions of every image point, where the decisions concern whether there is a feature of a given type at that point or not. Thus the resulting feature may be subsets of the image domain, e.g. in the form of isolated points, continuous curves or connected regions.

In some embodiments the extraction of information of features is performed by detecting features which are present on the combined 3D digital representation and/or on the 3D digital representation comprising geometrical data.

An advantage of this embodiment is that features can be detected by comparing the textural data and the geometric data at each point of the location. For example both the geometrical data and the textural data may show a feature, e.g. curve, in the same place, and this may mean that the feature is both geometrical and textural, and it may also be a confirmation that the feature is a real feature in the location, e.g. on the model or impression, and not just an error. If for example only the geometrical data show a feature in that place, and then this means that there is no textural feature there, or only the textural data may show a feature in that place, and this means that the feature is not geometrical or spatial but only textural, e.g. visible color. The last may be the case, when the dental technician has drawn some features on e.g. a model of the teeth for example for indicating where a removable partial denture should be arranged on the model and eventually in the mouth of the patient. Many dental technicians may prefer to work manually with a gypsum model, and when they draw the outline of e.g. a partial removable partial denture on the gypsum model, then the drawing is detected or captured when performing the textural data acquisition.

In some embodiments feature detection comprises examining every pixel in one or more of the digital representations to detect if there is at least part of a feature present at that pixel.

In some embodiments the one or more features are selected from the group of lines, contours, curves, edges, ridges, corners, or points.

It is an advantage that the different features can be detected by means of a feature detector which may be a software algorithm. Feature detectors can be classified into two different categories: intensity-based detectors and structure-based detectors. The intensity-based detectors analyze local differential geometry or intensity patterns to find points or regions that satisfy some uniqueness and stability criteria. The structure-based detectors analyze structural features such as lines, edges, and curves to define so-called interest points or regions.

Edges may be defined as points where there is a boundary or edge between two image regions, and edges can thus be defined as sets of points in the image which have a strong gradient magnitude. Some algorithms can link high gradient points together to form a more complete description of an edge. The algorithms may put constraints on the properties of an edge, such as shape, smoothness, and gradient value.

Corners are point-like features in an 2D image, which have a local 2D structure. After performing edge detection, the edges can be analyzed to detect rapid changes in direction, i.e. a corner.

Points or interest points are points which can be detected by searching for high levels of curvature in the image gradient. E.g. a dark spot or point on a white background can be detected by looking at the curvature in the image gradient.

Blobs or larger regions of interest points are areas in a 2D image which may be too smooth to be detected as a point, but these regions may still have a preferred or key point, such as a local maximum or a centre of gravity.

A ridge can be defined as a one-dimensional curve that represents an axis of symmetry and also has an attribute of local ridge width associated with each ridge point.

When a feature has been detected, the result may be a feature descriptor or feature vector which identifies a local region of the image.

When a feature has been detected, a local image patch around the feature can be extracted by means of image processing, and the result may be denoted a feature descriptor or feature vector.

Some common feature detectors are:
for detecting edges: Canny and Sobel;
for detecting interest points or corners: Harris, Shi & Thomasi, level curve curvature, and FAST;
for detecting blobs or larger regions of interest points: Maximally stable extremal regions (MSER) and principal curvature-based region detector (PCBR). MSER is an example of an intensity-based detector.

In feature detection tasks changes in lightning, pose, color and texture can cause considerable variation in local intensities, and therefore local intensity may not provide a stable detection cue. Intensity-based detectors may therefore fail to identify discriminative features. An alternative to capturing local intensity cues is to capture semi-local structural cues such as edges and curvilinear shapes. These structural cues may be more robust to intensity, color, and pose variations. The PCBR detector exploits these more reliable image structural cues.

The information of the one or more feature may comprise one or more 3D splines that are extracted from the 2D digital representation comprising textural data using various techniques. The 3D spline may e.g. correspond to pencil markings on a physical model of the location, and the method may comprise extracting the 3D spline and applying it in the 3D modeling of the 3D object.

For some applications, such as when extracting information from pencil markings on a physical model, the presentation of the features in the 2D images of the acquired 2D digital representation may need to be improved by for example by enhancing the contrast or by removing of noise from the 2D image. The features may be detected in the 2D images of the 2D digital representation and registered into the 3D digital representation comprising geometrical data.

In addition to the image processing and the feature detection, the method may comprise 3D spline detection, where the 3D spline detection comprises merging two or more 2D splines to provide the 3D spline.

The image processing may comprise a filtering, such as a Coherence-Enhancing Diffusion Filtering, applied to remove sensor noise. In addition to sensor noise, the features may comprise segments that are not coherent and/or segments that are not ideally defined on the location. When e.g. drawing a line with a pencil on a physical model of the location, the pencil may jump over the surface of the physical model thus leaving gaps in the line, or the operator may have drawn a line consisting of partially overlapping segments. In the case of segmented line a gradient approach may be applied to determine whether to adjacent lines are oriented such that one segment is arranged such that it can be considered an extension of the other segment. In that case, the two line segments may be considered to be part of the same line.

The image processing may comprise a contrast enhancement in the 2D image, such that e.g. pencil markings on a physical model of the location appear more clearly in the 2D images of the 2D digital representation. The contrast enhancement may be provided by e.g. a modified Sigmoid function, where the amount of contrast enhancement is decided by a single parameter, the alpha parameter, going from 0 to 1, where alpha values approaching 0 gives a linear exchange (no effect) and an alpha value of 1 gives an even sigmoid function.

Image sharpening making the transition between markings and background more obvious may also improve the reliability of the extracted information of the one or more features.

After the image processing, the features may be isolated in the 2D images, such that they can be detected and the information can be extracted. An automatic Scale-space selection may be used for the detection of the features.

Depending on the broadness of e.g. a pencil stroke on a physical model of the location, the scale at which the markings are best identified can automatically be found. The Scale-space selection may also be part of the images processing.

The detection of the features as ridges or edges in the 2D images of the 2D digital representation may provide a number of possible pixel candidates to be identified as the feature. These candidates need to be sorted and converted to splines. This may be done in a sequence comprising excluding very small line pieces. Whether this exclusion is to take place may depend on the image quality. If the image quality and/or the definition of features are such that disjunct line pieces of the features cannot be closed or connected during preprocessing of the 2D images and/or the feature detection, it may be advantageous that the exclusion of small line pieces does not take place.

A rough sorting may be used to exclude candidates whose 3D position is on a facet with a very steep angle to the eye-ray of the camera used for acquiring the 2D image. This will exclude silhouette-edges as well as low quality data.

Possible 3D splines corresponding to e.g. the pencil marking of a dental technician can then be identified using both geometrical data from the 3D digital representation and the detected 2D ridges/edges in combination. In the identification of the 3D splines, certain rules may have to be set up in order to handle line crossings, corners, and blobs.

Image patches showing sections of the surface of the location can be found from the 2D images of the 2D digital representation comprising textural data. The image patches may be aligned such that patches relating to neighboring sections of the location are aligned side by side. Texture weaving may then be applied in order to ensure that any visible transitions appearing at the borderline between neighboring image patches are made less visible. Such a visible transition could e.g. be a transition between a section imaged with a more intense illumination of the location and a section imaged with a less intense illumination of the location. The texture weaving may be made to smoothen visible transition between the different sections of the visualized combined 3D digital representation in order to improve the appearance of the visualized 3D digital representation. During the extraction of information, such transitions could also in some cases lead to a false identification of the transition as a feature of the location. The texture weaving may be performed by comparing pixel intensities within two neighboring patches and assigning intensity values to the pixels across the transition between two patches such that a smooth change in the pixel intensity is obtained.

3D Splines may be optimized by an operator using control points on the 3D spline where the position of these control points relative to the location can be optimized using a pointer tool, such as a mouse, or data entry using e.g. a keyboard.

The 3D modeling of the object may comprise defining a part of the object by the extracted 3D spline. The method may hence comprise automatically adapting the shape of that part to the 3D spline.

In some embodiments the one or more features comprises a margin line of a prepared tooth or die.

The margin line is the preparation margin line, which the dentist has grinded in the patient's tooth for preparing the tooth for a restoration e.g. a crown or bridge. The dental technician may draw a physical line with a color pen on a physical gypsum model for marking the margin line of a prepared tooth.

The texture of the model or die or tooth where a preparation margin line has been grinded is more rough than the surrounding surface, which is smooth, such as enamel on tooth. A preparation line may be made using a dental tool which is typically not less than 1 mm in diameter. So the preparation margin line can be detected by studying the texture of the model or die or tooth. Microtexture may also be detected. Burn marks from the grinding of the preparation line can also be detected in a texture scan.

Thus grinding marks of the margin line may be photographed or captured as textural features using a regular light source and a camera, where the camera for example has a high resolution. However, a 3D scanner comprising a light source and a camera for scanning geometrical features may also be used for scanning preparation margin lines as the geometrical features.

When detecting a preparation margin line in e.g. the geometrical data representation, the margin line may automatically be marked, e.g. as a clear red line, on the digital representation of the location.

In some embodiments the one or more features comprises the shades of the patient's teeth.

An advantage of this embodiment is that if for example the textural data of the features are acquired by performing a direct scanning of the patient's present or existing teeth, then the shade or color of the teeth can be captured as textural data and thus as textural features, and this information can be used to model or apply the correct shade of the object for example a restoration, artificial teeth in a full or partial denture, an implant etc. This may be a very efficient and fast method for determining the correct shade of the object, which is particularly important for dental applications.

In some embodiments the one or more features are drawn on the location, on a physical model of the location, or on an impression of the location by a user prior to the acquisition of the 2D digital representation comprising textural data.

An advantage of this is that the dental technician can design the object manually by drawing or grinding or providing other textural markings on the physical model, if he or she prefers this.

In some embodiments, the features are part of the 3D object that is to be modeled. This may for example be different parts of a removable partial denture or of an orthodontic appliance which are arranged to form part of the location from which the digital representations are acquired. These parts may then be identified in the combined 3D digital representation, and in the 3D modeling of the 3D object these parts may be modified or maintained depending on the preference of the operator.

The 3D object may comprise a removable partial denture such that the one or more features may be major connectors, clasps and/or retention grids, and such that the 3D modeling comprises defining one or more edges of the removable partial denture from the 3D feature.

In some embodiments the one or more features are used for modeling a removable partial denture, and the one or more features are major connectors, clasps and/or retention grids.

An advantage of this is that a partial denture may be a complex object having several different components, and it may be faster and intuitively easier for the dental technician to first design and model this rather complex dental device manually instead of on a graphical user interface.

In some embodiments the 3D object comprises orthodontic appliance or bracket, such that the one or more features are used for modeling such an orthodontic appliance or bracket, and the one or more features are bracket position(s), screw position(s), metal framework, plastic shelves, shells, bite plates, push rods, and/or springs. The 3D modeling may comprise defining the bracket positions and/or the screw position from the 3D feature.

An advantage of this is that an orthodontic appliance may be a complex object having several different components, and it may be faster and intuitively easier for the dental technician to first design and model this rather complex dental device manually instead of on a graphical user interface.

In some embodiments different features are drawn with different colors by the user. An advantage of this is that the different features can easily be distinguished due to the different colors.

Furthermore, the colors used for drawing on the impression or model should be colors with contrast to the model or impression and to the background color in the compartment, e.g. in the scanner, where the impression or model is scanned, such that the drawing can actually be imaged or recorded. For example brown drawings may not provide enough contrast to a dark model or a black background compartment. A definition of contrast is that it is the difference in visual properties that makes an item, or its representation in an image, distinguishable from other items and the background. Thus the item may be an impression or a physical model of teeth or the teeth themselves. In visual perception of the real world, contrast is determined by the difference in the color and brightness of the item and other items within the same field of view.

In some embodiments the feature is a borderline between different structures of the location.

In some embodiments the feature is a borderline between different materials of the location.

A borderline may also be denoted a transition, a relief, or a change in the height and/or material in the location.

A preparation margin line may be a borderline, since it is a transition between a grinded part, the rough preparation margin line, and a non-grinded part, the smooth enamel of the tooth.

Palate wrinkles may be a borderline, since the palate wrinkles are a kind of relief, where the surface changes in height. The detection of palate wrinkles can be used to model e.g. a partial denture for a patient, which will be adjoining the palate.

The transition between papilla of the gums and teeth can be a borderline, since here different materials are present, the hard enamel of the teeth surface and the soft tissue of the gum or gingival.

The borderline may be part of the location and hence directly defined on the location. The borderline may also be defined on a physical model of the location or on an impression of the location In some embodiments acquiring the 3D digital representation comprising geometrical data and acquiring the 2D digital representation comprising textural data are performed sequentially.

Thus the digital representations may be acquired in two separate recordings, using one recording means or two or more recording means, which may be arranged either as separate devices or arranged as one device.

Alternatively the acquisition of the 3D digital representation comprising geometrical data and the acquisition of the 2D digital representation comprising textural data are performed simultaneously.

In some embodiments, at least one of the digital representations is acquired by illuminating at least part of the location, a physical model of the location, or an impression of the location with light, such that the 2D digital representation comprising textural data and/or the 3D digital representation comprising geometrical data may be acquired by illuminating the location with light In some embodiments the light used to acquire at least one of the digital representations is multispectral light comprising light at N wavelengths, wherein the number N is equal to or larger than 2.

In some embodiments, the method comprises using different colors or color codes to identify different features, where the different colors or color codes correspond to the N wavelengths of the multispectral light. Such that the color used to identify one feature reflects light at one wavelength, while the color used to identify another feature reflects light at another wavelength.

Which kind of light illumination to be used when scanning is dependent on whether an impression or a model is scanned or whether direct scanning of the location, e.g. teeth is performed. If using a 3D scanner to scan an impression or a model, the compartment into which the impression or model is arranged for scanning it, could be e.g. black or white. If the compartment is colored white, the light for scanning may be reflected diffusively inside the compartment. The diffusively reflected light may be advantageous for imaging texture on the impression or model. However, if the compartment is colored black, then there may be no reflection of light. Thus for different scanning purposes, such as geometrical scanning or texture scanning, where color can be scanned or recorded, the color and the shape of the compartment of the scanner could advantageously be changeable, such as to be suitable for the different scanning or imaging modes.

A 3D scanning device configured for acquiring the 3D digital representation may be based on the projection of one or more sheets of light or another known pattern of light onto the location. The source of illumination may be a low-power laser in the visible light spectrum, or the illumination of the location for acquisition of geometrical data and/or textural data may be performed using a different kind of laser, a laser diode, or light emitting diodes, LEDs, emitting e.g. red, green, and blue light.

The sensor for receiving, measuring, and converting the reflected light or signal from the location may be a five megapixel camera with a resolution of 35 micrometer. There may be more than one camera for capturing the reflected light from the location, but the cameras may all capture both the geometrical data and the textural data of the location.

In some embodiments the N wavelengths in the multispectral light used for the illumination of the location are provided in a sequence, such as a sequence comprising red, green and blue light. Each step in the sequence may be performed without any overlap or with an overlap with the preceding and/or the following step in the sequence. In case of overlapping steps it may be required that the timing of the acquisition of 2D images of the 2D digital representation is such that the 2D images are acquired while light at only one wavelength illuminate the location. Overlapping steps may also be used in relation to cases where color codes with two or more colors are used for the identification of different parts of the feature or different features.

Alternatively and/or additionally, other spectral peaks may also be employed, e.g. near infrared (NIR) or ultra violet (UV). Wave-length dependent calibration of the optical system may be performed in order to ensure spatial correspondence of the recorded surface reflectivity measures.

Furthermore, color information may be acquired simultaneously through the use of multiple sensors and beam splitters, or through the use of color filter arrays (CFA), which may be arranged in a Bayer-type arrangement.

In some embodiments, N is 3 such that the multispectral light comprises light at a first wavelength, light at a second wavelength, and light at a third wavelength. When N equals 3, the sequence may be first wavelength, second wavelength, and third wavelength. The different permutations of this order is also possible, such that light at the second wavelength is followed by light at the first wavelength which then is followed by light at the third wavelength.

The sequence may thus be first wavelength, third wavelength, and second wavelength.

The sequence may thus be second wavelength, first wavelength, and third wavelength.

The sequence may thus be second wavelength, third wavelength, and first wavelength.

The sequence may thus be third wavelength, second wavelength and first wavelength.

The sequence may thus be third wavelength, first wavelength, and second wavelength.

The first, second and third wavelengths may be in the red, green, and blue range of wavelengths, respectively.

In some embodiments, the N wavelengths in the multispectral light are provided simultaneously.

In some embodiments, the N wavelengths in the multispectral light are provided in a white light source, such that the location is illuminated with the N wavelengths and any other wavelengths of the white light source.

The white light source may comprise white diodes emitting light over a significant part of the visible part of the electromagnetic spectrum.

A 2D image may be acquired for each of said N wavelengths.

In some embodiments an 2D image is acquired for each of said N wavelengths, such as for each of red, green and blue light.

Acquiring data relating to features, e.g. lines, such that they appear or are present in the resulting 2D or 3D representation, may be possible using regular light illumination and e.g. acquiring a black/white representation. But in order for capturing the correct color of the lines, e.g. if they are drawn on the impression or model using a pen, the colors can be acquired using sequential illumination, where the red, the green and the blue light from e.g. light diodes are detected separately.

In some embodiments the 2D images acquired for the each of the N wavelengths in the multispectral light, such as for the red, green and blue light, are stitched together into a common 2D image. The 2D digital representation may comprises one or more common 2D images, each common 2D image comprising 2D images acquired at each of the N wavelengths In the context of the present invention, the phrase "blue light" and "light with a wavelength in the blue range" may be used in relation to electromagnetic waves propating with a wavelength in the range of about 450 nm to about 490 nm.

In the context of the present invention, the phrase "green light" and "light with a wavelength in the green range" may be used in relation to electromagnetic waves propating with a wavelength in the range of about 490 nm to about 560 nm.

In the context of the present invention, the phrase "red light" and "light with a wavelength in the red range" may be used in relation to electromagnetic waves propating with a wavelength in the range of about 635 nm to about 700 nm.

In some embodiments the method comprises texture weaving, which comprises weaving the one or more features together between neighbor 2D images based on the textural data of the 2D digital representation.

An advantage of this embodiments is that the texture such as color in the resulting 2D image appears to be natural and correct, and surface scattering from e.g. skin is accounted for. The object of texture weaving and similar processes are to filter out all changes in appearance that are due viewpoint or light properties, i.e. modulations of the surface that are a result of external processes, rather than inherent properties of the object surface. Texture weaving smoothes out transitions between different images, such that the transitions becomes smooth with regard to texture, such as different features, e.g. color etc. Thus in order to capture textural data for the entire location, a number of 2D images may be acquired and weaved together, e.g. four textural images may be captured for covering the entire location. Image processing may be used to remove specular effects from the surface of the location for which data are being captured.

Scans of the location acquired from different viewpoints relative to the location using e.g a laser as the first light source may be stitched together, and several geometrical scans may be acquired for covering the entire location, and thus the geometrical features may be stitched together.

Texture weaving is sometimes also referred to a texture blending.

Texture weaving is described e.g. in Marco Callieri, Paolo Cignoni, Claudio Rocchini, Roberto Scopigno Weaver, an automatic texture builder from Proceedings of the First International Symposium on 3D Data Processing Visualization and Transmission (3DPVT'02), 2002, IEEE Computer Society.

In some embodiments the method comprises laser modulation of the light used for acquiring the 3D digital representation comprising geometrical data.

An advantage of this embodiment is that laser modulation can help with acquiring geometry on surfaces with non-uniform reflectivity, thus the laser source may be modulated during acquisition of geometrical information in order to compensate for variations in reflectivity, both in a diffuse and in a specular setting. This will, in turn, allow for geometry acquisition of the objects exhibiting a dynamic range greater than that of the camera sensor.

The same approach can be employed for texture acquisition, however here there may be an added requirement of detailed knowledge regarding the amount of emitted light.

Laser modulation may be performed using a modulator which is a device which is used to modulate a beam of light, where the beam may be carried over free space, or propagated through an optical waveguide. The modulator may manipulate different parameters of the light beam, such as amplitude, phase, polarization etc. Modulation of intensity of a light beam can be obtained by modulating the current driving the light source, e.g. a laser diode.

In some embodiments, the method comprises modulation of the light used for acquiring the 2D digital representation comprising textural data.

In some embodiments acquiring the 3D digital representation comprising geometrical data of the location and the 2D digital representation comprising textural data of the location is performed by means of a scanner adapted for capturing geometrical data and textural data.

In some embodiments acquiring the geometrical data and the textural data is performed by means of a camera adapted for capturing both geometrical data and textural data.

The camera may be a five megapixel color camera.

Alternatively, two or more cameras may be provided which have different resolutions to capture data for different kinds of features or for different geometrical or textural features.

In some embodiments acquiring the geometrical data is performed by means of a first light source, and acquiring the textural data is performed by means of a second light source.

The second light source may comprise an array of diodes, where the array of diodes comprises a number of first diodes, a number of second diodes and a number of third diodes, where the first, second diodes and third diodes are adapted to emit light at a first, second and third wavelength, respectively.

The second light source may comprise a diffuser arranged to provide a diffusion of the emitted light, such as a diffusion of the light emitted from a white light source or from an array of red, green and blue diodes.

The geometrical data may be captured using a laser, where a number of scans captured from different angles may be stitched together into an assembled model. Furthermore, the 2D digital representation comprising textural data may be acquired using a regular white light source, and the result may be a 2D image. A few 2D images may be suitable for covering the entire location, and textural weaving may be performed to avoid incoherent or bad transitions between the 2D images.

Alternatively, the same light source may be used for capturing both the geometrical data and textural data. An advantage of using only one light source, is that geometrical data and textural data can be captured simultaneously, whereas when using two light sources, the light sources may not be turned on at the same time, since one of the light sources may disturb the capturing of data using the other light source.

Alternatively and/or additionally, color filters can be employed allowing for simultaneous acquisition of geometry and texture data.

Alternatively and/or additionally, light may be provided at the acquisition unit, e.g. a ring of light around the receiving optics of the camera(s). An advantage of this is that the light/camera angle can be minimized and thereby the amount of deep shadows in deep cavities can be minimized.

The light source may be white light, such as structured white light or white light in combination with a grid.

In some embodiments, the positioning unit comprises at least a two-axis motion system, such that the positioning of the location during the acquisition of the 3D digital representation comprising geometrical data and the 2D digital representation comprising textural data is performed automatically by means of the at least a two-axis motion system.

In some embodiments, the method comprises that the acquisition of geometrical data and textural data is performed automatically by means of at least a two-axis motion system.

It may be an advantage that the acquisition and the motion system runs automatically, such that no operator should manually select each position. The motion system may be e.g. a two-axis or three-axis motion system, since hereby data of the location can e.g. be captured both from the sides and from above.

In some embodiments the method comprises providing a 3D face scan of the patient for facilitating visualizing the result of the modeling of the 3D object.

It may be an advantage to use a 3D face scan of the patient when modeling e.g. restorations, a partial denture, orthodontic appliances etc., because the modeled object can then be seen or viewed in connection with the patient's entire face and look.

In some embodiments the 3D digital representation comprising geometrical data of the location, and/or the 2D digital representation comprising textural data of the location is/are obtained by means of a 3D face scan.

In some embodiments the method is adapted to be used for 3D modeling within dentistry.

In some embodiments dentistry comprises restorations, implants, orthodontics, such as bracket placement and appliances, and partial dentures, such as removable partial dentures.

Within restorations it is an advantage that the preparation margin line can be detected from the representation of geometrical data and textural data.

Within orthodontics it is an advantage that the dental technician can draw on a physical model where the appliance or brackets should be arranged, or that tooth segmentation can automatically be performed using the representations of geometrical data and textural data.

In the modeling of a 3D object used within dentistry, an edge of the one or more parts of the 3D object may be defined by the extracted information, such as the 3D spline. The 3D modeling may comprise extracting a plurality of features, such as a plurality of lines drawn on a physical model of the location, where a number of features relate to one part of the 3D object. For example, when modeling a removable partial denture, the retention grid may be defined by a number of drawn lines on a physical model of the teeth and palette. When a number of features are detected, they may be mapped to specific parts of the 3D object based on knowledge specific parts and/or based on the location, length, color, and shape of the feature. The different parts of a removable partial denture, such as the retention grid, the window, the major connector and the minor connectors may for example be defined using different colors. They may also be identified from the knowledge that the window is at the palette and that the retention grid is on the gingival. When the modeled 3D object is a removable partial denture, the 3D feature may be a 3D spline defining the perimeter of a part of the removable partial denture, such as e.g. the retention grid or the major connector.

The different parts of a 3D object may also be defined using identification marks, such as two or more concentrically arranged circles, crosses, squares, triangles, and so forth. The number of elements in the identification mark may also be used, such that e.g. the retention grid of a removable partial denture has one mark, the major connector has two, and so forth.

In some embodiments, the feature comprises identification marks arranged within a substantially closed edge of the feature. The closed edge may for example be a closed loop drawn on a physical model of the location. The identification marks may be selected from the group of concentrically arranged circles, crosses, squares, triangles, the number of elements in the identification mark, such as the number of dots.

A closed loop may for example be drawn to mark the edge of different parts of a removable partial denture and different identification marks may be used to identify these different parts. The major connector may for example be identified using one dot, the retention grid using two dots and a window using three dots.

Furthermore, the method can for example be used for determining occlusion of a patient by placing a color trace paper between the patient's upper and lower teeth, and when the patient bites his teeth together, the paper will transmit color to the colliding points on the teeth, and this transmitted color can be captured as textural data. Determining occlusion may be performed either directly in the mouth and thus on the real teeth of the patient, or it may be performed on a physical model of the teeth, e.g. gypsum model, using e.g. an articulator.

In some embodiments the method is adapted to be used for 3D modeling of hearing devices. The feature may then define the boundary of an inner face or an outer face of the hearing aid device, the position or cross sectional shape of the vent, or an ID-tag for the hearing aid device.

The feature may be defined on a physical model or an impression of the ear canal in relation to which the hearing aid device is adapted to be arranged. The hearing aid device may be an in-the-ear device, an in-the-canal device, or a behind-the-ear device. The feature may relate to different parts of the hearing aid device, such as to the shell, an ear mould or an integrated face plate of the device.

In some embodiments, the information is extracted by an operator from the visualized combined 3D representation comprising both geometrical data and textural data. The operator may for example identify different pieces of information as relating to the same feature. This may e.g. be done while visualizing the combined model on a graphic display.

The method can also be used for modeling of customized shoes with a perfect fit for the patient, where the geometrical and textural features of the patient's feet are acquired either by direct scanning or by making an impression of the feet and then scanning the impression or producing a physical model from the impression and then scanning the physical model. The textural data of the feet are also acquired.

In some embodiments, the method is implemented on a computer program product comprising program code means for causing a data processing system to perform the method of any one of the preceding claims, when said program code means are executed on the data processing system.

The first and/or the second digital signal processor unit may be configured for extracting the information of the one or more features from the 2D digital representation.

The first and the second digital processor units may be integrated parts of a digital signal processing device, such that the digital signal processing device is configured for analyzing and combining the acquired digital representations and for modeling the 3D object.

The acquisition unit may comprise:
means for acquiring a 3D digital representation of at least a part of a location arranged in said scan volume, where the 3D digital representation comprises geometrical data of the location; and
means for acquiring a 2D digital representation of at least a part of location arranged in said scan volume, where the 2D digital representation comprises textural data of the location;

The acquisition unit may comprise a first set of cameras arranged to receive light from the scan volume and to acquire both said 3D digital representation comprising geometrical data and said 2D digital representation comprising textural data from a location. The first set of cameras is then part of both the means for acquiring a 3D digital representation and the means for acquiring a 2D digital representation. The first set of cameras may comprise two cameras arranged relative to the scan volume and the first light source such that a 3D scan of a location positioned in the scan volume is possible.

The system may comprise one or more further cameras in addition to the first set of cameras, such as a second camera or a second set of cameras.

In some embodiments, the acquisition unit is configured for acquiring textural data for N different features of a location, where each feature has a unique color or color code, and for distinguishing between said N different features based on said color or color code. The features may be defined using e.g. different colored inks or paints. Likewise, the acquisition unit may be configured for acquiring textural data for N different parts of a feature of a location, where each part has a unique color or color code, and for distinguishing between said N different parts based on said color or color code. In the following the description often focused on the acquisition of data relating to different features, but the comments made may apply equally to the case where data for different parts of a feature is acquired.

In some embodiments, the illumination unit of the system comprises a first light source adapted for providing light for the acquisition of geometrical data of a location, and a second light source adapted for providing light for the acquisition of textural data.

The light used for illuminating the location may hence comprise both light emitted from the first light source and the second light source.

The location may be illuminated simultaneously with the first and second light sources, or one at a time.

A light source which is adapted for providing light for the acquisition of geometrical data of a location may be configured for emitting light in substantially parallel rays.

A light source adapted for providing light for the acquisition of the acquisition of textural data may be configured to provide a diffusive light where the directions of different rays of light are more randomly distributed.

The first and second light sources may be arranged such that the optical axis of the first light source and the optical axis of the second light source intersects in a scan volume.

In some embodiments, the first light source comprises a monochromatic laser emitting light at a first laser wavelength. The light from such a monochromatic laser may be propagating in substantially parallel rays allowing for a precise determination of the geometry of a location.

The first laser wavelength may be in the green range of wavelengths, in the red range of wavelengths, or in the blue range of wavelengths. A red laser may, at the present time, provide a cost effective system as such lasers often can be purchased at a lower price than e.g. a blue laser. A green laser may have the advantage of providing a better spatial resolution when color cameras are used for acquiring the digital representations.

The second light source may be arranged at a different angle relative to the scan volume than the first light source but still such that light from the second light source can be reflected from a location in the scan volume towards cameras of the acquisition unit.

In some embodiments, the second light source comprises a broad band light source, such as a white light source, delivering light over a range of wavelengths. The second light source may be configured for providing light at all wavelengths of the colors or color codes used to defined features in a multicolor arrangement.

For some applications relating to the acquisition of textural data it may be preferred that the light is diffusive. The second light source may be adapted for providing diffusive light.

The second light source may be configured for providing light at isolated wavelengths such that a spectrum of the intensity distribution of the emitted light signal versus wavelength comprises a number of peaks.

The second light source may be realized using a design comprising a number of sources each emitting light at a single wavelength or in a relatively narrow wavelength range, where the signals emitted from each of these sources is combined to provide the light emitted from the second light source.

The second light source may be realized using a design utilizing a resonant effect such as a Fabry Perot resonator.

In some embodiments, the second light source comprises an array of diodes, where the array of diodes comprises a number of first diodes, a number of second diodes and a number of third diodes, where the first, second diodes and third diodes are adapted to emit light at a first, second and third diode wavelength, respectively.

In some embodiments, the second light source comprises a diffuser arranged to provide a diffusion of the emitted light, such as the light emitted from a while light source or an array of diodes. Such diffusive light delivered from the second light source may be adequate for acquiring information relating to the texture of the location.

In some embodiments, each camera in the first set of cameras comprises a color camera comprising a color filter array (CFA) arranged in a Bayer-type arrangement, a so-called Bayer filter, in front of a photosensitive element configured to detect electromagnetic signals.

When using a Bayer filter it may be advantageous that the first light source emits light at wavelengths in the green passband of the Bayer filter, since the Bayer filter provides that the spatial resolution provided by the camera is twice the resolution obtained using a first light source which emits light at a wavelength corresponding to red or blue light.

In some embodiments are one or more cameras in the first set of cameras a monochrome camera. Each of the cameras may be monochrome cameras.

In some embodiments, the system comprises a scan plate located such that a location arranged on said scan plate is positioned in said scan volume, such that that light from both the first and second light sources can be reflected from a physical model at the scan plate towards the acquisition unit of the system. The arrangement of the scan plate may hence be such that a least part of physical model or an impression placed on the scan plate is located in the scan volume of the system In some embodiments, the control unit is adapted to control the motion and rotation of this scan plate.

In some embodiments, the system comprises a positioning unit for at least two-axis motion of the scan plate such that acquisition of the 3D digital representation comprising geometrical data and of the 2D digital representation comprising textural data from a number of positions can be performed automatically.

In some embodiments, the system comprises a positioning unit configured for arranging the location in a number of different positions relative to the acquisition unit, such that a desired coverage of the location can obtained by acquiring the 2D digital representation comprising textural data and the 3D digital representation comprising geometrical data from the number of different positions.

In some embodiments, the system comprises a control unit configured for controlling the array of diodes and the positioning unit.

The control unit may be configured to provide that the first, second and third diodes emits light sequentially, such that a sequence of light signals are emitted. The sequence may be first wavelength, second wavelength, and third wavelength.

The control unit may be configured to provide that the sequence is repeated a number of times, such as one time for each relative arrangement of the optical assembly of the system and the scan plate.

In the context of the present invention, the phrase "optical assembly" may refer to the assembly of units used for providing the illumination of the location and for acquiring the 2D and 3D digital representations of the location. The optical assembly may comprise the acquisition unit and the light sources of the system.

In some embodiments, the second light source is designed such that the first, second and third diodes are arranged in according to a Bayer arrangement.

In some embodiments, a digital signal processor of the system is configured for real-time analysis of the acquired 2D digital representations and 3D digital representations.

The first set of cameras may be used to acquire both the 2D digital representation and the 3D digital representation, When placing a Bayer filter in front of the photosensitive elements of the cameras, it may be advantageous to use a laser emitting light in the green wavelength range as the first light source since this may provide a higher spatial resolution compared to a red laser due to the design of a Bayer filter, where twice as many sections allows green light to pass through the filter as there are sections allowing red light to pass through.

A scanning of a physical model or an impression of a location can then required in order to ensure that the acquired representations provides data for the whole feature. This may for instance be the case when the feature is a margin line on a physical model of a tooth prepared for a crown.

In some embodiments, the system comprises a motion system for at least two-axis motion such that acquisition of the 3D digital representation comprising geometrical data and of the 2D digital representation comprising textural data from a number of positions can be performed automatically.

In some embodiments, the system comprises a control unit configured for controlling the array of diodes and the motion system.

The control unit may be configured to provide that the first, second and third diodes emits light sequentially, such that a sequence of light signals are emitted. The sequence may be such the wavelength of the emitted light from the second light source is first wavelength, second wavelength, and third wavelength. Any sequence of wavelengths can in principle be used depending on the purpose of the sequential illumination to the light of the second light source. Preferably, the used sequence must be known by the digital signal processor or microprocessor which links each 2D digital representations to the wavelength(s) used when acquiring each of them.

The control unit may be configured to provide that the sequence is repeated a number of times, such as at least one time for each relative arrangement of the optical assembly and the scan plate.

The first, second and third diodes are arranged according to a Bayer arrangement, with alternating red and green diodes in a number of rows that are separated by rows having alternating green and blue diodes.

The used of a broadband light source, such as a white light source, or an light source configured for emitting light at a number of discrete wavelengths, such as an array of diodes may be advantageous when the different colors define the feature of the location.

The feature may e.g. comprise a section having a color which differs from the color of a different section of the feature and from the color of the surrounding regions of the physical model of the location. Such a section having a color may e.g. be a colored line drawn on on a physical model of the location. A colored section reflects light over a limited range of wavelengths. Outside this limited range the reflection may be negligible such that when the colored section is illuminated with light having wavelengths outside this limited range it will appear dark compared to when illuminated with light inside the range.

If the second light source comprises diodes that are driven to sequentially emit light at different wavelengths and the first set of cameras comprises black and white cameras, different 2D digital representations comprising textural data may be acquired by the black and white cameras, where each 2D digital representation comprising textural data is acquired at one color of the light emitted from the second light source.

The acquisition of 2D digital representations using light at different wavelengths makes it possible to define different types of features or different parts of features using different colors on the location or on e.g. a physical model of the location. The feature may comprise a colored line defined on a physical model of the location, such as a line having a color which allows the feature to be identified from the remaining part of the physical model.

Consequently if a feature is identified on the physical model using the three different colors, such that each color corresponds to the different parts of the feature, the different parts of the feature can be identified from the three different 2D digital representations that can be acquired using different colors from the second light source.

Different features can in the same manner be identified from different 2D digital representations comprising textural data if each feature is identified using a feature specific color e.g. on a physical model of the location.

In some embodiments, the system comprises a digital signal processor or microprocessor configured for real-time analysis of the acquired 2D digital representations and 3D digital representations.

The different part of the optical system can also be integrated in a handheld scanner, where the change between different relative arrangements of the system and the location (or a model or impression of the location) is obtained by moving the handheld scanner. The integration in a handheld scanner may require that some of the components of the system are reduced in size. In a handheld scanner system the digital signal processor or microprocessor may be placed in the scanner handle or in a separate processing box.

Some embodiments of the optical assembly of the system may utilize tunable filters that may be controlled by the control unit such that the tunable filters are synchronized with the acquisition of the 2D digital representations. The first set of cameras may then be monochrome cameras and the pass band of the tunable filters is changed such that 2D digital representations are acquired for a number of different pass bands. One pass band may cover part of the range of wavelengths corresponding to red light, while another may correspond to green light, and yes another to blue light. When tunable filters are used, the second light source may be a broadband source emitting a light over a range of wavelengths covering all pass band ranges of the tunable filter, or at least cover the colors used for defining the features e.g. on a physical model of the location.

The present invention relates to different aspects including the method described above and in the following, and corresponding methods, devices, systems, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a system for performing 3D modeling of a 3D object adapted to be inserted in or worn by a patient, wherein the system comprises:
  means for acquiring a 3D digital representation of at least a part of the location where the object is adapted to be arranged, where the 3D digital representation comprises geometrical data of the location;
  means for acquiring a 2D digital representation of at least a part of the location where the object is adapted to be arranged, where the 2D digital representation comprises textural data of the location;
where the acquisition of the 2D digital representation comprising textural data and 3D digital representation comprising geometrical data is performed by repositioning the location and acquisition means relative to each other for obtaining a desired coverage of the location;
  means for aligning and combining the 2D digital representation comprising textural data and the 3D digital representation comprising geometrical data to obtain a combined 3D digital representation comprising both geometrical data and textural data of the location;
  means for visualizing the combined 3D representation comprising the geometrical data and the textural data of the location; and
  means for applying information of one or more features from the 2D digital representation comprising textural data of the location, when modeling the 3D object.

The acquisition of the 2D digital representation comprising textural data and 3D digital representation comprising geometrical data may be performed by automatically repositioning the location and acquisition means relative to each other for obtaining the desired coverage of the location.

The means for acquiring a 3D digital representation may comprise an acquisition device configured for acquiring a 3D digital representation of a location.

The means for acquiring a 2D digital representation may comprise an acquisition device configured for acquiring a 2D digital representation of a location.

The means for aligning and combining the 2D digital representation comprising textural data and the 3D digital representation may comprise a data processing device configured for aligning and combining a 2D digital representation and a 3D digital representation.

The means for visualizing the combined 3D representation may comprise a visualization device configured for visualizing a 3D representation, such as a graphical user interface, such as a computer screen.

The means for applying information of one or more features from the 2D digital representation may comprise a device configured for applying information when modelling the 3D object.

The system may be configured for providing that the 3D modeling is computer implemented.

In some embodiments, the acquisition unit, the positioning unit, and the first and second light sources, are provided in a 3D scanner.

The first and/or the second digital signal processor unit may be configured for extracting the information of the one or more features from the 2D digital representation.

In some embodiments, the first and second digital processor units are integrated parts of a digital signal processing device. The digital signal processing device may hence perform both the analyzes and the 3D modeling of the 3D object.

In some embodiments, the acquisition unit comprises:
means for acquiring a 3D digital representation of at least a part of a location arranged in said scan volume, where the 3D digital representation comprises geometrical data of the location; and
means for acquiring a 2D digital representation of at least a part of a location arranged in said scan volume, where the 2D digital representation comprises textural data of the location.

In some embodiments, the acquisition unit comprises a first set of cameras arranged arranged to receive light from the scan volume and to acquire both said 3D digital representation comprising geometrical data and said 2D digital representation comprising textural data from a location.

In some embodiments, the illumination unit comprises a first light source adapted for providing light for the acquisition of geometrical data of a location, and a second light source adapted for providing light for the acquisition of textural data.

The optical axis of the first light source and the optical axis of the second light source may intersects in the scan volume.

In the context of the present invention, the phrase "optical axis" may refer to an imaginary line that defines the path along which light propagates through the system. The optical axis of the first light source may hence be a line connecting the first light source and a point on the scan plate of the system, where the point is in the volume which is illuminated by the first light source.

In some embodiments, the first light source comprises a monochromatic laser emitting light at a first laser wavelength.

The first laser wavelength may be in the green range of wavelengths, in the red range of wavelengths, or in the blue range of wavelengths, or in the infrared range of wavelengths, or in the ultraviolet range of wavelengths.

In some embodiments, the second light source comprises a broadband light source, such as a white light source.

The acquisition unit may be configured for acquiring textural data for N different features of a location, where each feature has a unique color or color code, and for distinguishing between said N different features based on said color or color code.

The color or color codes may be defined using colored ink or paint, or the color or color codes may be naturally occurring on the location.

In some embodiments, the second light source is configured for emitting light that allows features having a unique color or color code to be identified from an acquired 2D digital representation based on the wavelength of the light emitted from the second light source.

The second light source may comprise an array of diodes, where the array of diodes comprises a number of first diodes, a number of second diodes and a number of third diodes, where the first, second diodes and third diodes are adapted to emit light at a first, second and third diode wavelength, respectively.

In some embodiments, the second light source comprises a diffuser arranged to provide a diffusion of the emitted light.

The use of diffusive light for the acquisition of the 2D digital representation may provide that the textural data of the 2D digital representation are more detailed than when using a beam of parallel rays.

At least one of the cameras in the first set of cameras, such as both cameras in the first set of cameras, may comprise a color camera comprising a color filter array (CFA) arranged in a Bayer-type arrangement in front of a photosensitive element configured to detect electromagnetic signals At least one of the cameras in the first set of cameras is a monochrome camera. Each camera in the first set of cameras may be a monochrome camera In some embodiments, the system comprises a scan plate arranged such that a location arranged on said scan plate is positioned in said scan volume.

The scan plate may be part of the 3D scanner.

In some embodiments, the system comprises a positioning unit configured for positioning the location in a number of different positions and/or orientations relative to the acquisition unit, such that a desired coverage of the location can obtained by acquiring the 2D digital representation comprising textural data and the 3D digital representation comprising geometrical data with the location arranged at different positions and/or orientations relative to the acquisition unit.

The positioning unit may be configured for at least two-axis motion of the scan plate such that acquisition of the 3D digital representation comprising geometrical data and of the 2D digital representation comprising textural data from a number of viewpoints can be performed automatically.

In some embodiments, the system comprises a control unit configured for controlling the array of diodes and the positioning unit.

The control unit may be configured to provide that the first, second and third diodes emits light sequentially, such that a sequence of light signals are emitted. The sequence may be first wavelength, second wavelength, and third wavelength, or any of said permutations.

The control unit may be configured to provide that the sequence is repeated a number of times, such as one time for each relative arrangement of the optical assembly of the system and the scan plate.

The first, second and third diodes of the second light source may be arranged according to a Bayer arrangement.

The first digital signal processor and the digital signal processing device may be configured for real-time analysis of the acquired 2D digital representations and 3D digital representations.

Disclosed is system for performing 3D modeling of a 3D object adapted to be inserted in or worn by a patient, wherein the system comprises:

means for acquiring a 3D digital representation of at least a part of the location where the 3D object is adapted to be arranged, where the 3D digital representation comprises geometrical data of the location;

means for acquiring a 2D digital representation of at least a part of the location where the object is adapted to be arranged, where the 2D digital representation comprises textural data relating to one or more features of the location;

where a desired coverage of the location is obtained by acquiring each of the 2D digital representation comprising textural data and the 3D digital representation comprising geometrical data from a number of different viewpoints relative to the location;

means for aligning the 2D digital representation comprising textural data and the 3D digital representation comprising geometrical data;

means for combining at least a part of the 2D digital representation comprising textural data and the 3D digital representation comprising geometrical data to obtain a combined 3D digital representation comprising both geometrical data and textural data of the location;

means for visualizing the combined 3D representation comprising the geometrical data and the textural data of the location; and means for 3D modeling the 3D object such that the modeled 3D object is adapted to be inserted in or worn by a patient, where said 3D modeling applies information of the one or more features from the acquired 2D digital representation comprising textural data.

Disclosed is also a computer program product comprising program code means for causing a data processing system to perform the method, when said program code means are executed on the data processing system, and a computer program product comprising a computer-readable medium having stored there on the program code means.

Disclosed is also a system wherein fluorescence is used for acquisition of a 2D digital representation comprising textural data.

Fluorescence effects may also be utilized when the feature comprises a fluorescent material. The feature may e.g. be defined using fluorescent ink on a physical model of the location.

A feature comprising a fluorescent material having an excitation band including the wavelength of the first light source may provide a Stoke shift of the wavelength of the first light source. In contrast, the light reflected from the location maintains its wavelength. Using various optical configurations known to the skilled person it is then possible to extract both the geometrical data and the texture data using only the first light source to illuminate the location.

Since the fluorescence typically is orders of magnitudes weaker than the reflected light it may be advantageous to detect the reflected light using the first set of cameras, while the fluorescence signal is detected using a second set of cameras. The second set of cameras may comprise a filter arranged to block light within the wavelength of the first light source, or filters may be placed between the location and the second set of cameras. The fluorescence may also be detected using a single second cameras, i.e. such that the second set of cameras contains only one camera. In one embodiment, the feature is defined using a paint or ink comprising a fluorescent material configured for two-photon excitation and the first light source emits light at a wavelength in the infra red range, such that when two infra red photons are absorbed, a photon in the visible range is emitted. The 3D representation comprising geometrical data is then acquired by detecting reflected infra red photons from the location, while the textural data directly can be acquired and related to the geometrical data.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

In the following description, reference is made to the accompanying figures, which show by way of illustration how the invention may be practiced.

Figure 1:
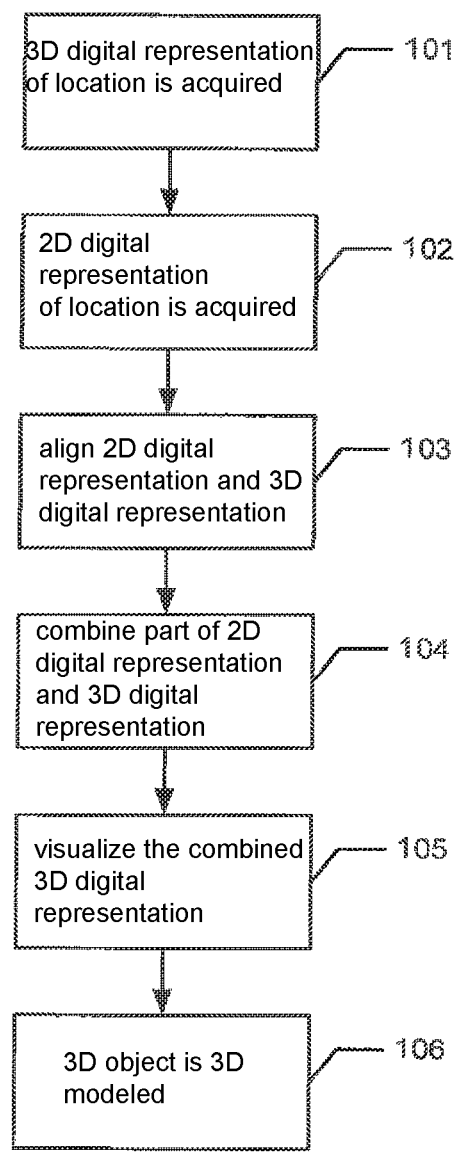
FIG. 1 shows an example of a flowchart of the method.

FIG. 1 shows an example of a flowchart of the method. The method is for 3D modeling of an object, which is adapted to be inserted in or worn by a patient.

In step 101 a 3D digital representation of at least a part of the location where the object is adapted to be arranged is acquired, where the 3D digital representation comprises geometrical data of the location.

In step 102 a 2D digital representation of at least a part of the location where the object is adapted to be arranged is acquired, where the 2D digital representation comprises textural data relating to one or more features of the location.

A desired coverage of the location is obtained by acquiring each of the 2D digital representation comprising textural data and the 3D digital representation comprising geometrical data from one or more different viewpoints relative to the location. Repositioning of the location relative to the system which is used for acquiring the digital representations may be performed manually or automatically;

In step 103, the 2D digital representation comprising textural data and the 3D digital representation comprising geometrical data are aligned.

In step 104 at least a part of the 2D digital representation comprising textural data and the 3D digital representation comprising geometrical data are combined to obtain a combined 3D digital representation comprising both geometrical data and textural data of the location.

In step 105, the combined 3D digital representation comprising the geometrical data and the textural data of the location is visualized. The digital representations may be shown on a graphical user interface, such as a computer screen.

In step 106 the 3D object is 3D modeled such that the modeled 3D object is adapted to be inserted in or worn by a patient, where said 3D modeling applies information of the one or more features provided by the acquired 2D digital representation comprising textural data.

The aligning, the combining, the visualization, and the application of information of the one or more features from the 2D representation for modeling may be digital, virtual actions, performed by means of software.

FIG. 2 shows examples of a model of teeth with textural features.

Figure 2A:
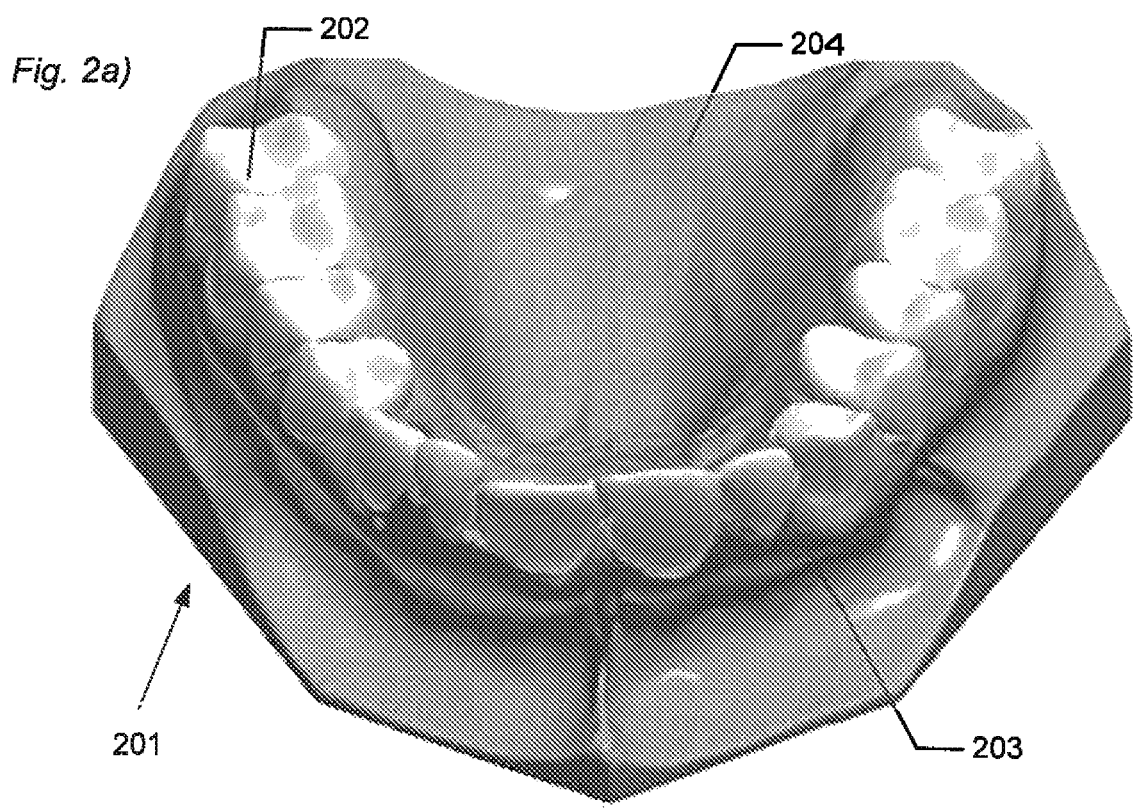
FIGS. 2a to 2e show examples of a model of teeth with textural features.

FIG. 2a) shows the model 201 which comprises teeth 202, gingival 203, and the palate 204 of a patient's mouth. The model 201 may be a physical model or a virtual model.

Figure 2B:
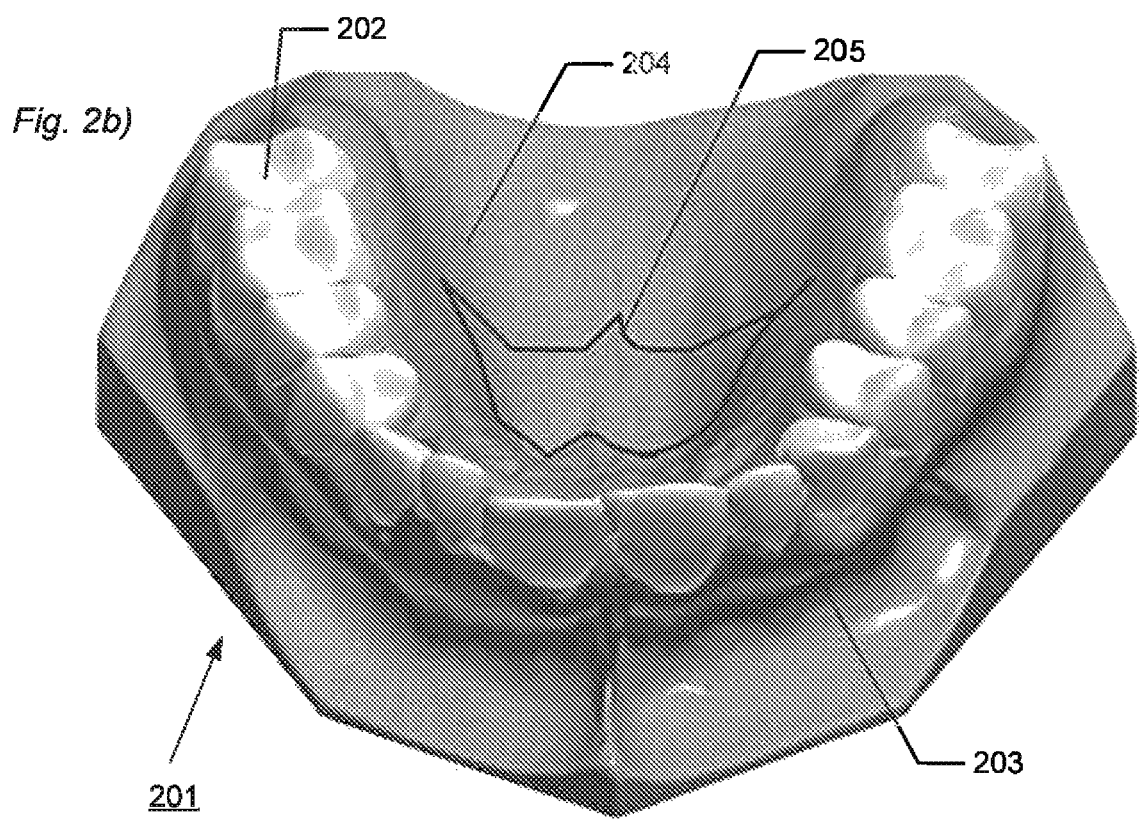

FIG. 2b) shows the model 201 with teeth 202, gingival 203, and the palate 204 of a patient's mouth. On the palate 204 a feature 205 is drawn. The feature 205 shows where on the palate 204 and with which shape a part of a removable partial denture should be arranged. At present no teeth 202 are missing on the model 201, but one or more of the teeth 202 may be replaced with artificial teeth in a partial denture, for instance if some of the teeth are broken, weak or dead.

The outline of the removable partial denture feature 205 may be drawn on a physical model 201 by a dental technician or it may be drawn digitally on a virtual model 201 shown on a computer screen.

A 3D scanning of the physical model 201 using e.g. a laser scanner for acquiring geometrical data of the model may only capture the data for the geometrical features of the model.

For acquiring the textural data of the feature(s) 205, e.g. the drawn outline of the partial denture, a 2D digital representation can be acquired by capturing the 2D images of the model.

When both geometrical and textural data are acquired, 2D features can be derived from the textural data to be used in the modeling of the 3D object which should fit the scanned location.

Figure 2C:
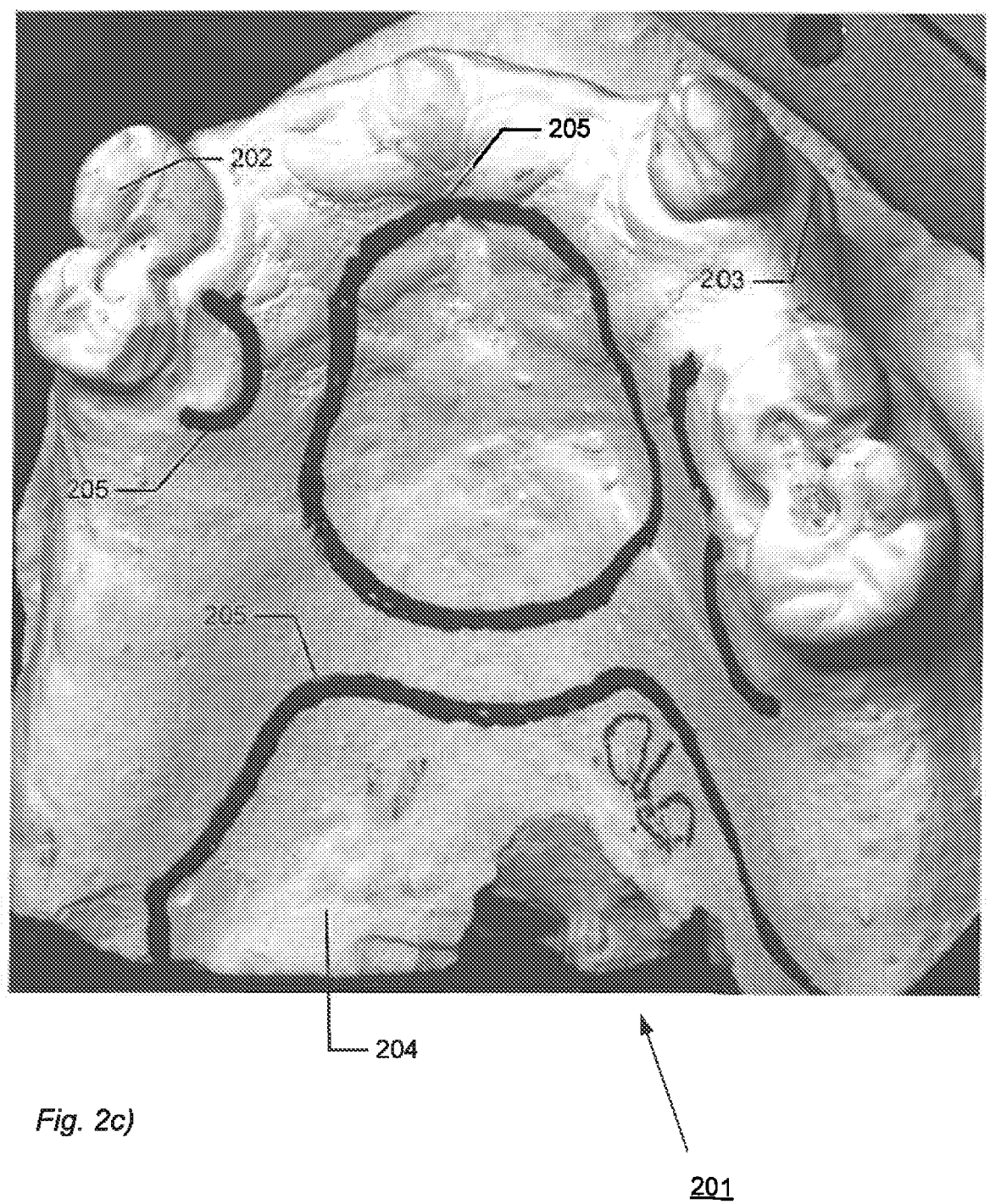

FIG. 2c) shows the a texture image of the physical model 201 with teeth 202, gingival 203, and the palate 204 of a patient's mouth. On the palate 204 and around some of the teeth 202, features 205 have been drawn. The features 205 show where and with which shape on the palate 204 and around the teeth 202 a partial denture should be arranged. Only five teeth 202 are present on the model 201, and thus several teeth are missing on the model 201, and one or more of the missing teeth will be replaced with artificial teeth in the partial denture.

The outline of the partial denture features 205 have been drawn on the physical model 201 by e.g. a dental technician or dentist.

This texture image clearly shows the features which are drawn physically and manually on the model.

For the 3D modeling of some cases, it may be advantageous to draw the lines on the physical model in different colors to increase to level of information that can be derived from the acquired 2D digital representation(s).

Figure 2D:
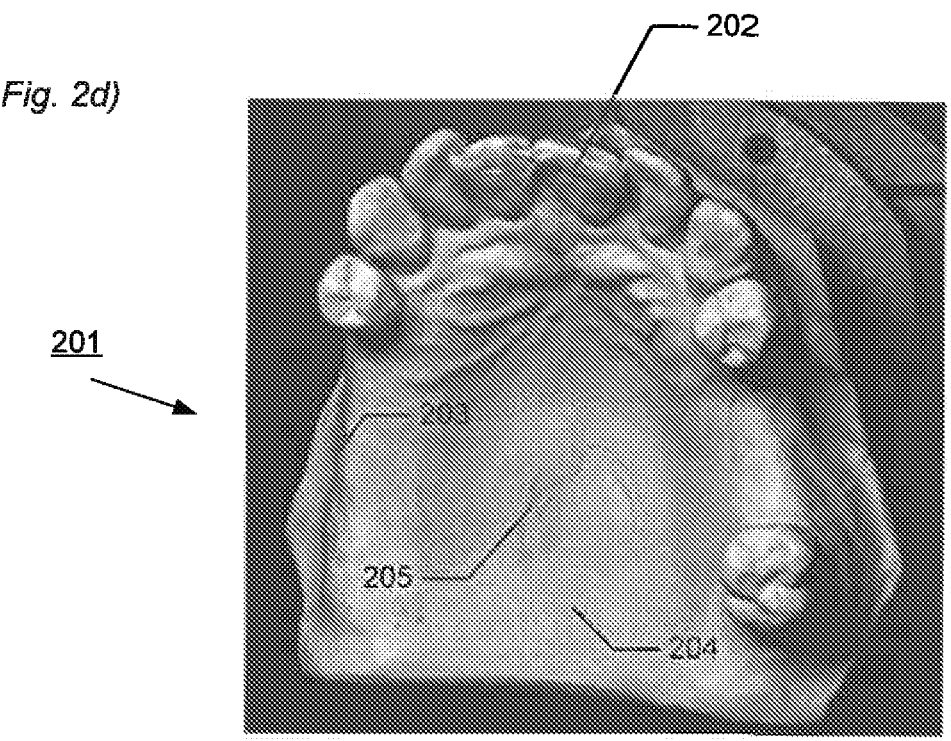

FIG. 2d) shows another result of a texture image or scan of the model 201 with teeth 202, gingival 203, and the palate 204 of a patient's mouth. On the palate 204 features 205 have been drawn. The features 205 show where on the palate 204 that a part of a partial denture should be arranged. Nine teeth 202 are present on the model 201, and thus several teeth are missing on the model 201, and one or more of the missing teeth can be replaced with artificial teeth in the partial denture.

The outline of the partial denture features 205 have been drawn on the physical model 201 by e.g. a dental technician or dentist.

This texture image or scan clearly shows the features which are drawn physically and manually on the model.

Figure 2E:
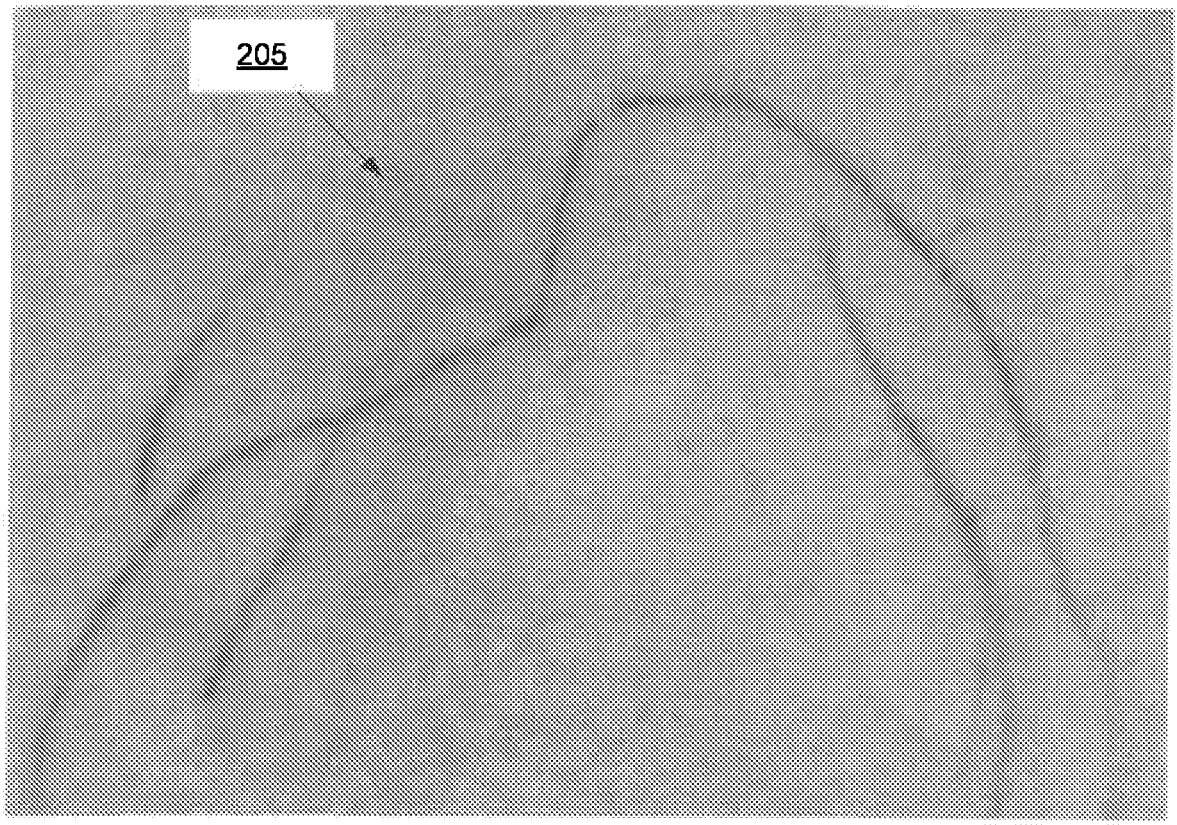

FIG. 2e) is a zoom of the feature 205 seen in FIG. 2d). The texture images are acquired using a 5 megapixel camera.

FIG. 3 shows an example of 3D modeling of a removable partial denture.

Figure 3A:
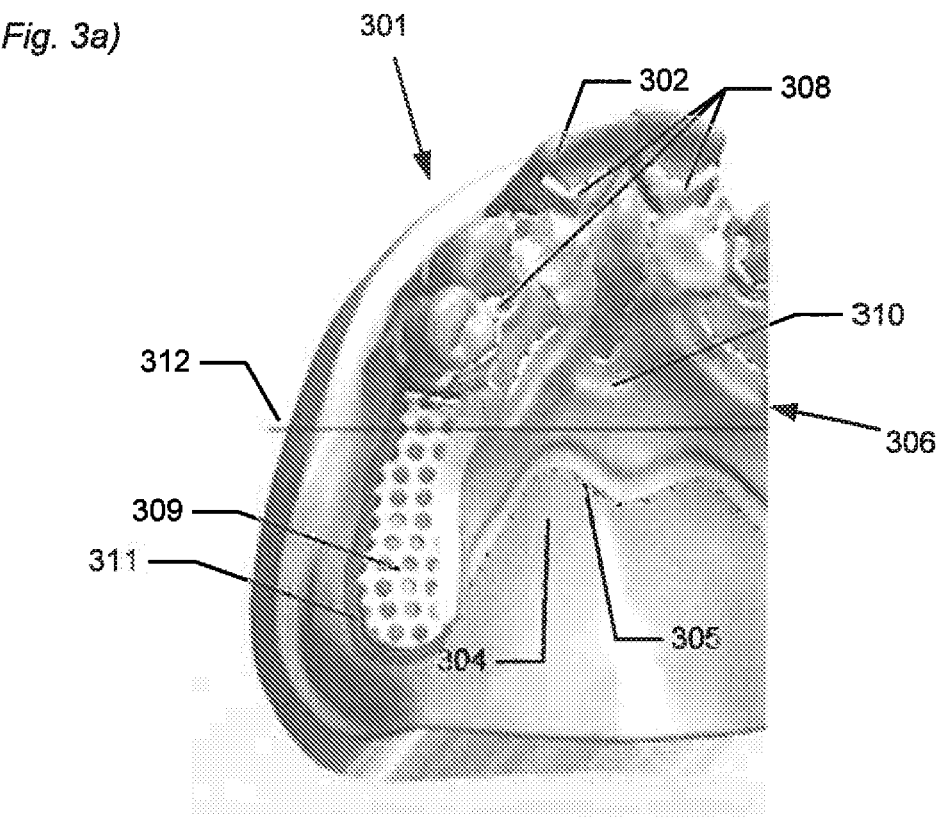
FIGS. 3a to 3c show an example of 3D modeling of a removable partial denture.

FIG. 3a) shows the removable partial denture 306 as seen from above.

Figure 3B:
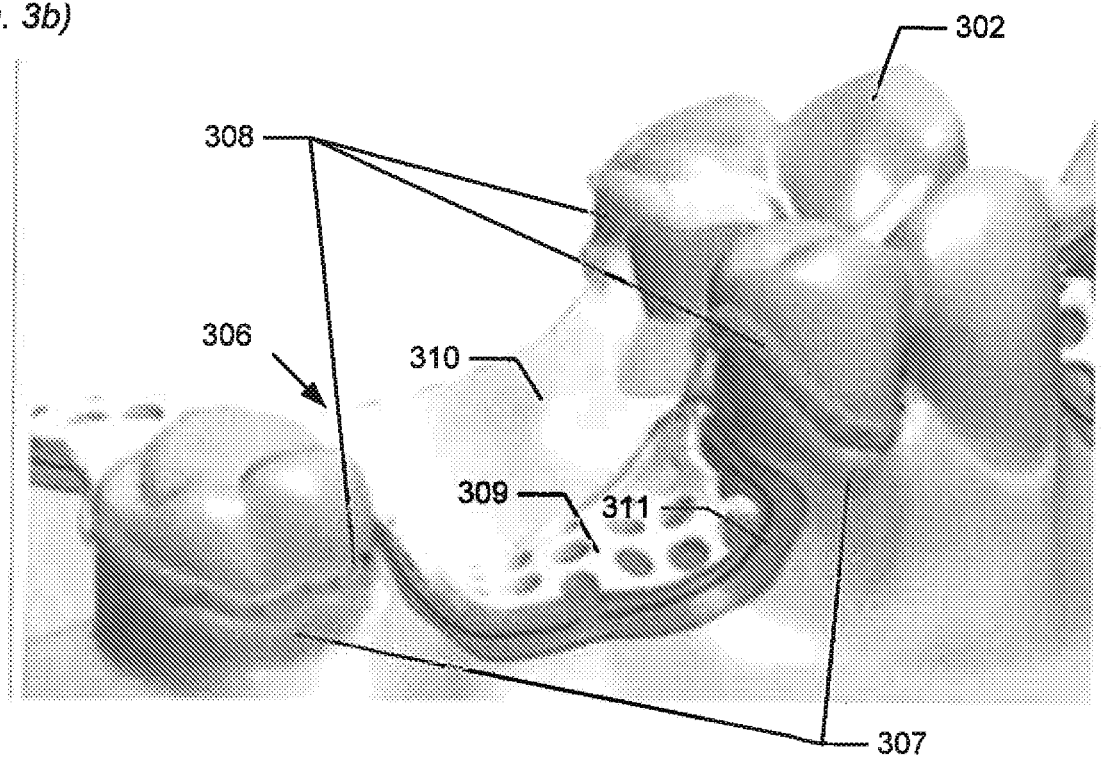

FIG. 3b) shows the removable partial denture 306 in a side view.

Figure 3C:
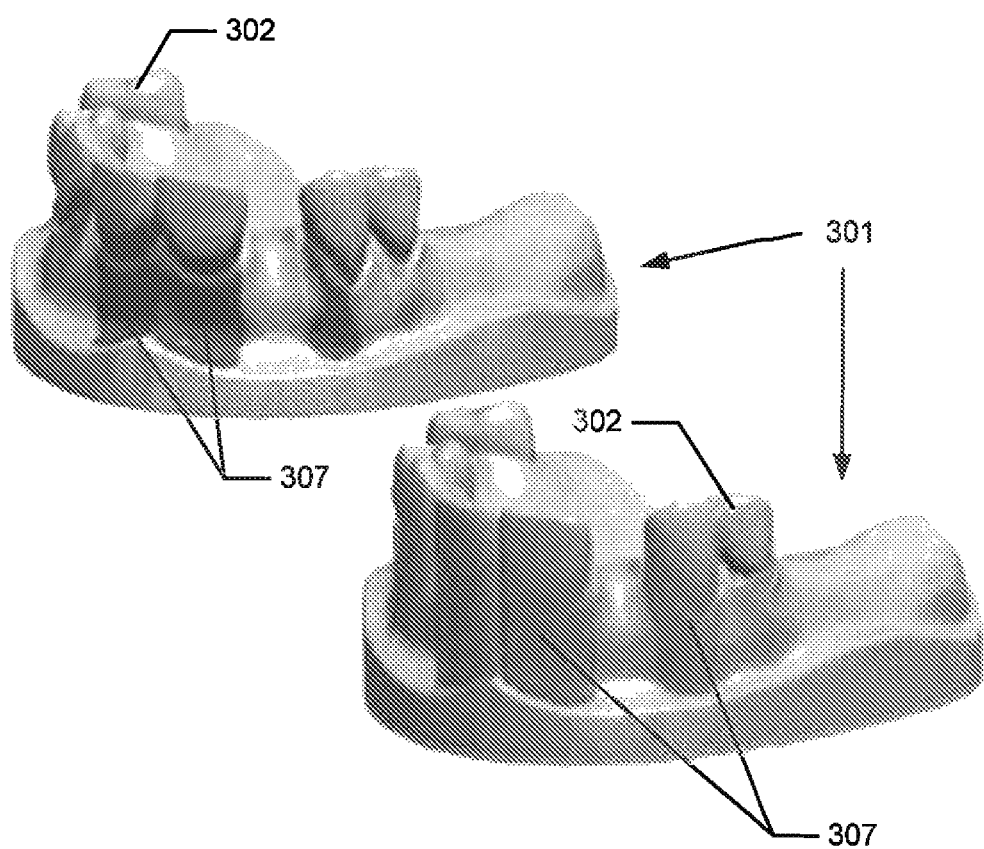

FIG. 3c) shows an example of blocking out of undercuts 307 and exposing undercuts 307 for clasp 308 planning.

After the physical model with the drawn texture, e.g. lines, has been scanned, the removable partial denture 306 can be digitally modeled.

First a dental 3D scanner can be used to scan a physical gypsum model or alternatively an impression to provide the 3D digital representation of the location where the removable partial denture 306 is to be worn by the patient. The scanner may scan geometrical features and textural features for securing an optimal image of the model 301 with teeth 302 and with the drawn texture 305, such as lines, for designing all the removable partial denture components with high accuracy in a few minutes, such as only 100 seconds. The removable partial denture components comprise clasps 308 for attachment to the teeth 302, retention grids 309 which stretches out on the gums where there are no teeth, the major connector 310 on the palate connecting the retention grids 309 and the claps 308.

FIGS. 3a), 3b) and 3c) show that the digital design process may intuitively mimic the manual steps, including blocking out of undercuts 307, exposing undercuts 307 for clasp 308 planning, retention grid 309 design with automatic resin gap 311, application of major connector 310 and, finally, addition of clasps 308 to the grid structure 309. The completely virtual workflow enables the dental technician to work on-screen as if he/she were using traditional wax tools.

When designing the retention grid 309, the first step may be to select from a list of pre-defined grid patterns and apply mesh to the digital model for a perfect fit. Then the next step may be marking the area for the major connector 310 using e.g. a fast edit tool. The system automatically designs for optimal strength.

If the lines, i.e. the textural features 305, have not already been drawn on the physical model, then the lines for clasp 308 placement may be virtually drawn. Predefined or customized clasps 308 are applied to the model, when the lines are present. By means of an interactive preview fine-adjustment of each feature of the removable 306 can be performed through control points.

A 2D cross section of the 3D digital model 301 may be shown, and the line 312 indicates where a cross section can be made.

Modeling a removable partial denture 306 as shown here is a highly productive and reliable customization of removable partial dentures 306, providing labs with accurate digital control over the process while reducing production time and costs. The process may cover all the steps for optimal design of both metal and flexible frameworks.

The method provides a high degree of flexibility and a digital workflow that maps out the practiced processes familiar to laboratory technicians.

The digital design removes the need for second re-factory model-making saving both time and money. The system's high accuracy and measurement features provide complete dimensional control over clasp 308 and connector 310 design and ensure good results, such as high esthetics, easy removability, proper chewing, and a perfect fit.

The completely digital survey accurately identifies undercuts 307, facilitates virtual wax block-out for easy removability, and enables undercut 307 exposure for optimal clasp 308 design.

Thus the method provides faster and easier design of perfectly fitting partials 306, provides a fast partial design by reducing the manual process time, provides that the intuitive workflow maps out the manual process, provides that ideal block-out points and retention areas can be identified in record time, reduces orders for readjustments and remakes, and increases dentist and patient satisfaction.

FIG. 4 shows an example of a modeled removable partial denture.

Figure 4A:
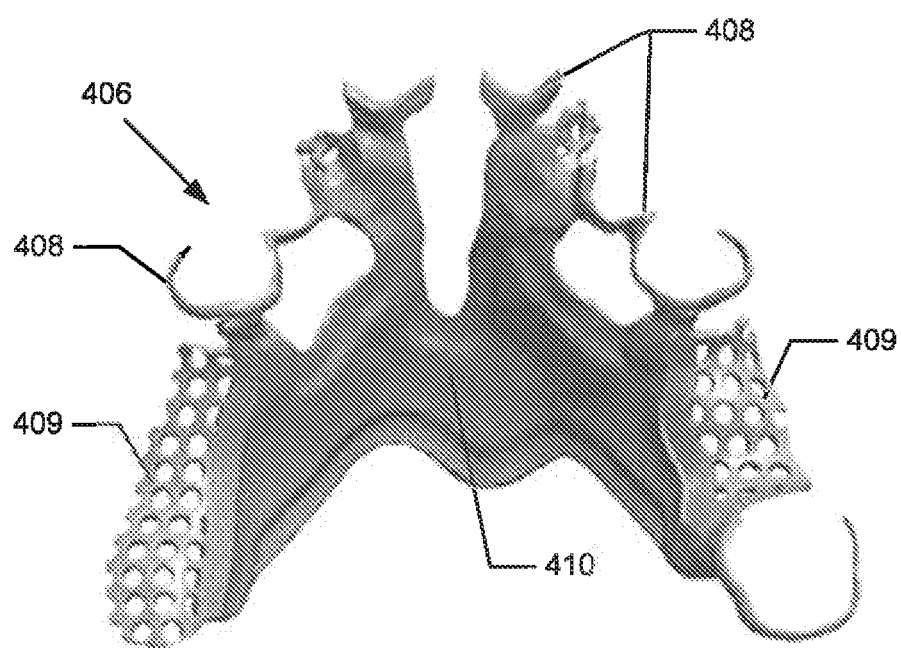
FIGS. 4a to 4b show an example of a modeled removable partial denture.

FIG. 4a) shows an example of a digital CAD model of the removable partial denture 406.

Figure 4B:
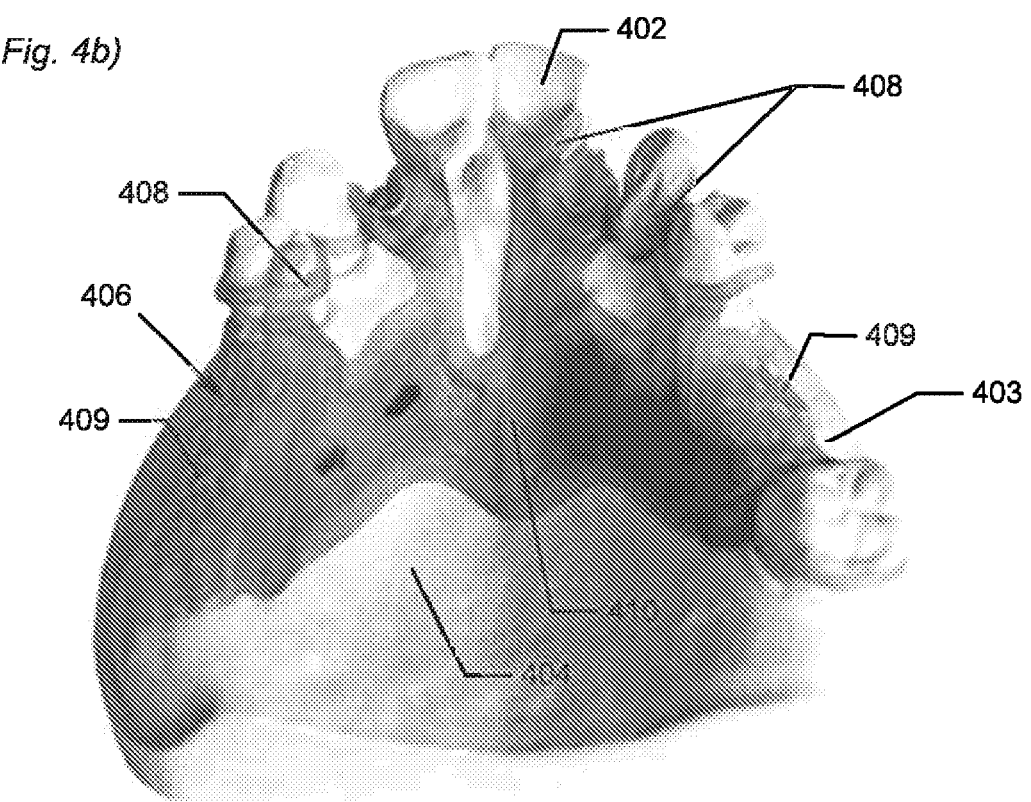

FIG. 4b) shows an example of the manufactured removable partial denture 406 attached to a model 401 of a patient's teeth 402, gingival 403 and palate 404.

The removable partial denture 406 comprises clasps 408 for attachment to the teeth 402, retention grids 409 which stretches out on the gums where there are no teeth, the major connector 410 on the palate 404 connecting the retention grids 409 and the claps 408.

FIG. 5 shows examples of a preparation margin line as a feature.

Figure 5A:
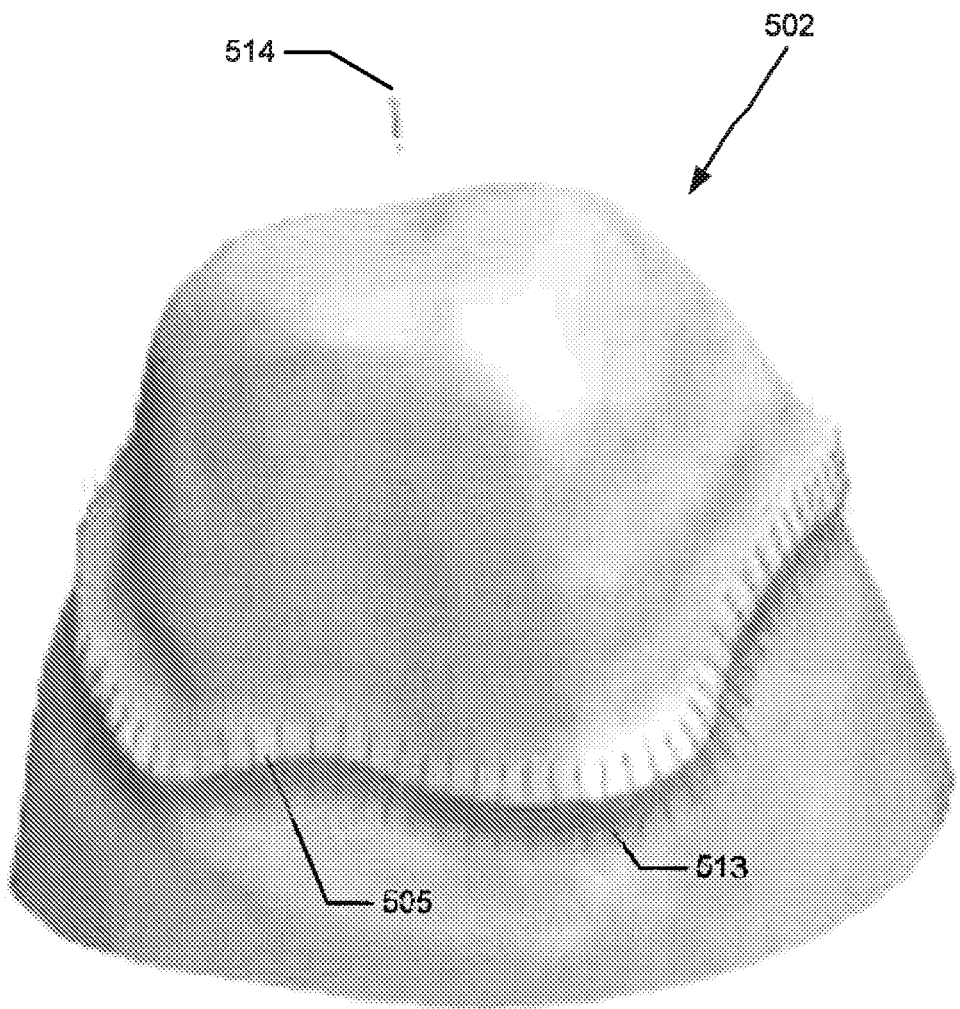
FIGS. 5a to 5m show examples of a preparation margin line as a feature.

FIG. 5a) shows a CAD drawing of a die or tooth 502 which is prepared meaning that it has been grinded such that a restoration, such as a crown, can be placed on the tooth 502. The preparation of the tooth 502 provides a preparation margin line 505 which is a feature which can be detected as a geometrical feature and/or as a textural feature when scanning or imaging the tooth 502. In FIG. 5a), the preparation margin line 505 is also marked with a colored line, and at points on the line small markers 513 indicate the perpendicular direction of the margin line at that point. The arrow 514 indicate the overall perpendicular direction of the margin line 505 or the insertion direction of the tooth 502.

Figure 5B:
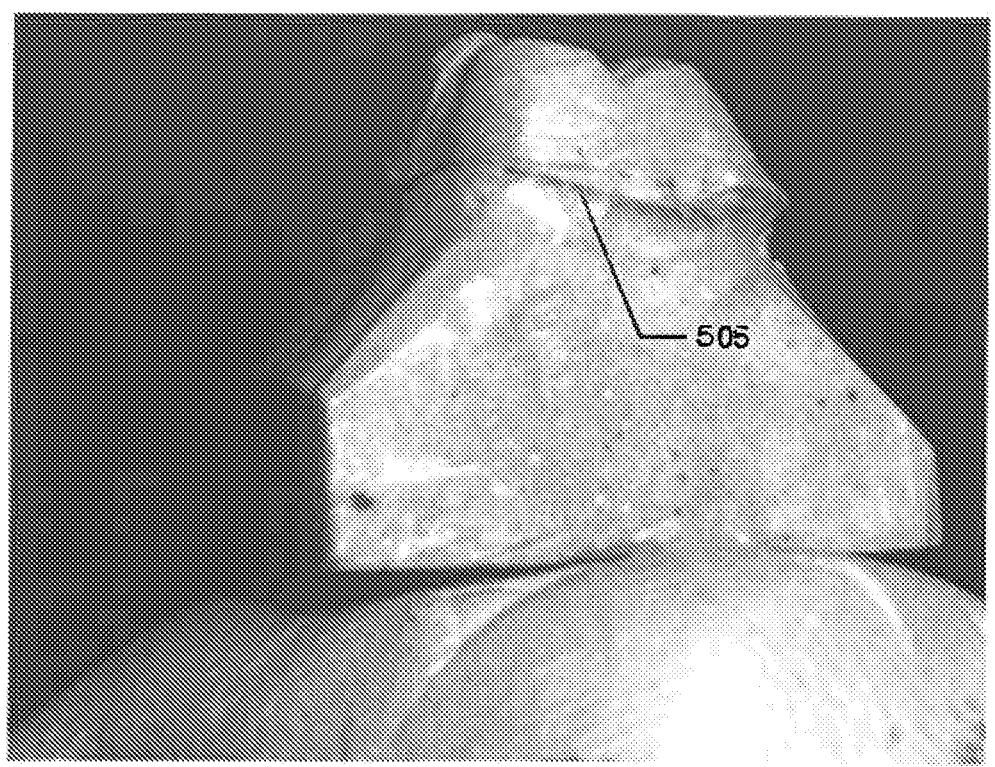
Figure 5C:
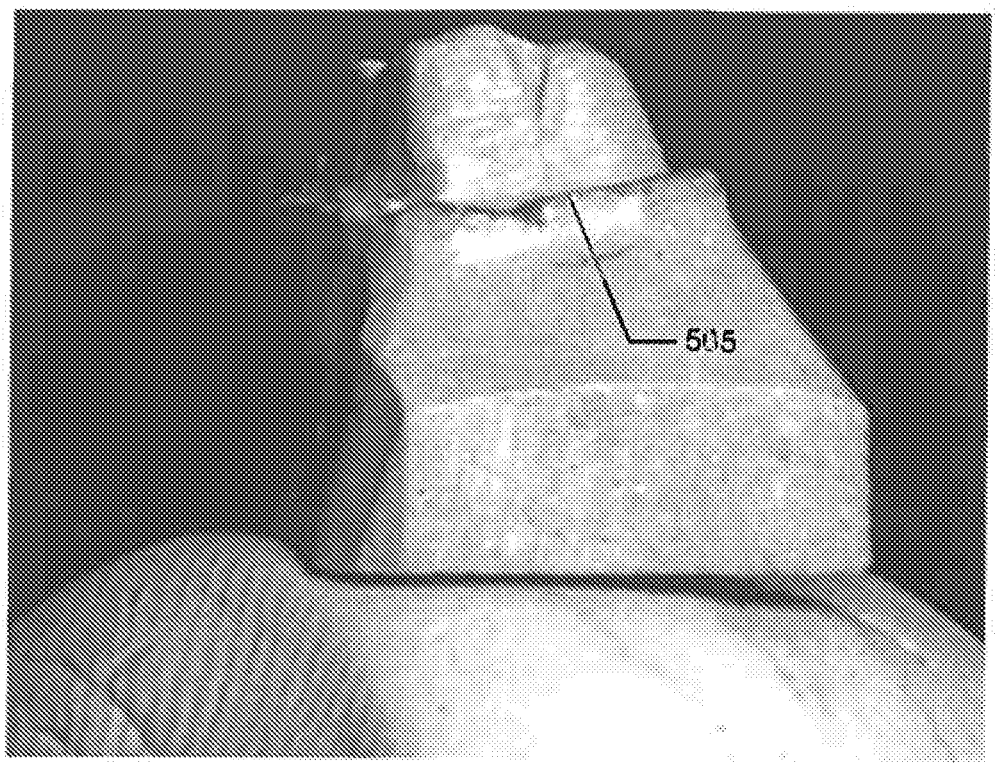
Figure 5D:
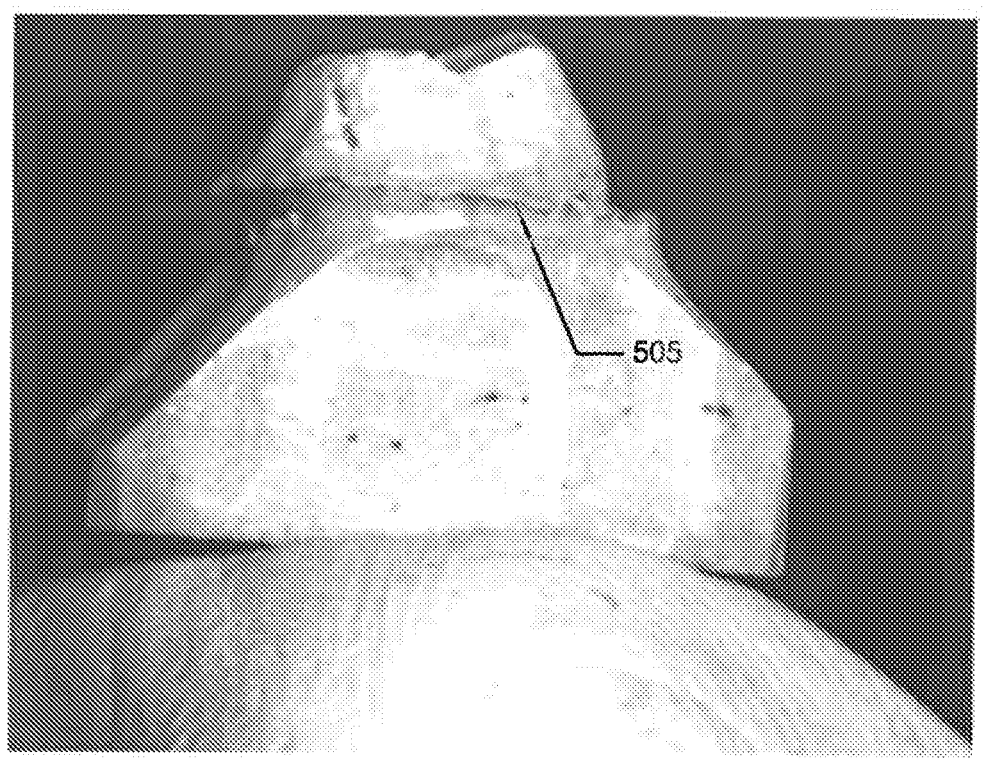
Figure 5E:
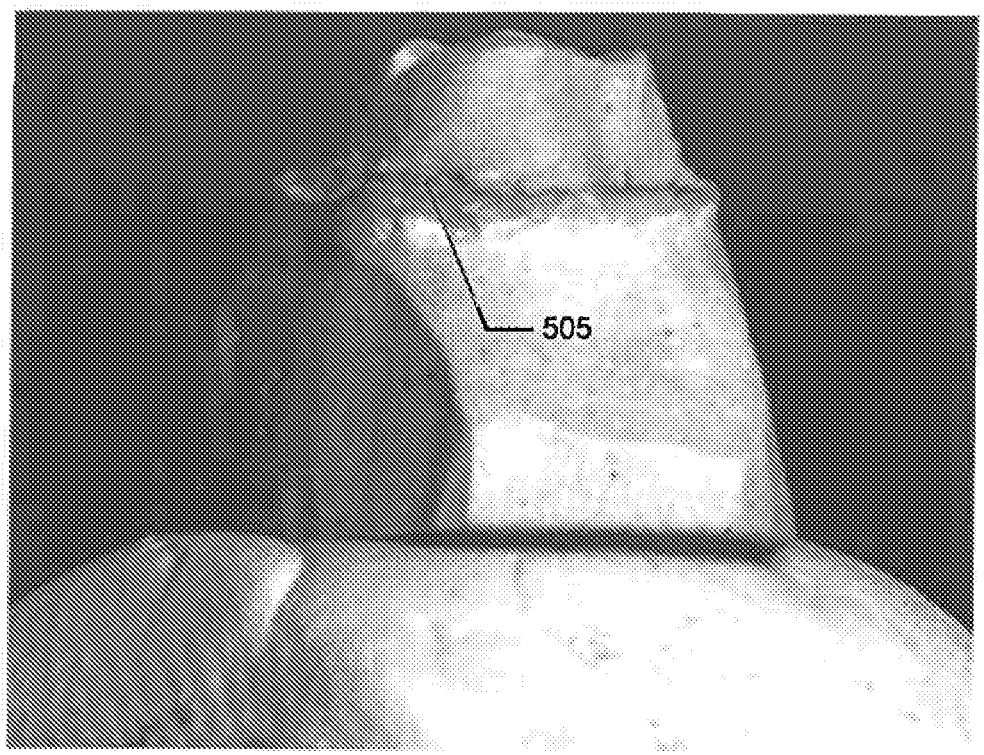

FIGS. 5b)-5e) show a number of texture images from different viewpoints of a die 502 which has been prepared meaning that it has been grinded such that a restoration, such as a crown, can be placed on the die 502. The preparation of the die 502 provides a preparation margin line 505 which is a feature which can be detected as a geometrical feature and/or as a textural feature when scanning or imaging the tooth 502. The preparation margin line 505 is also sketched or drawn on the die 502 with a color creating contrast to the color of the die and/or the background. The specular effects which are dominant in FIG. 5d) can be removed by means of texture weaving between the different images.

Figure 5F:
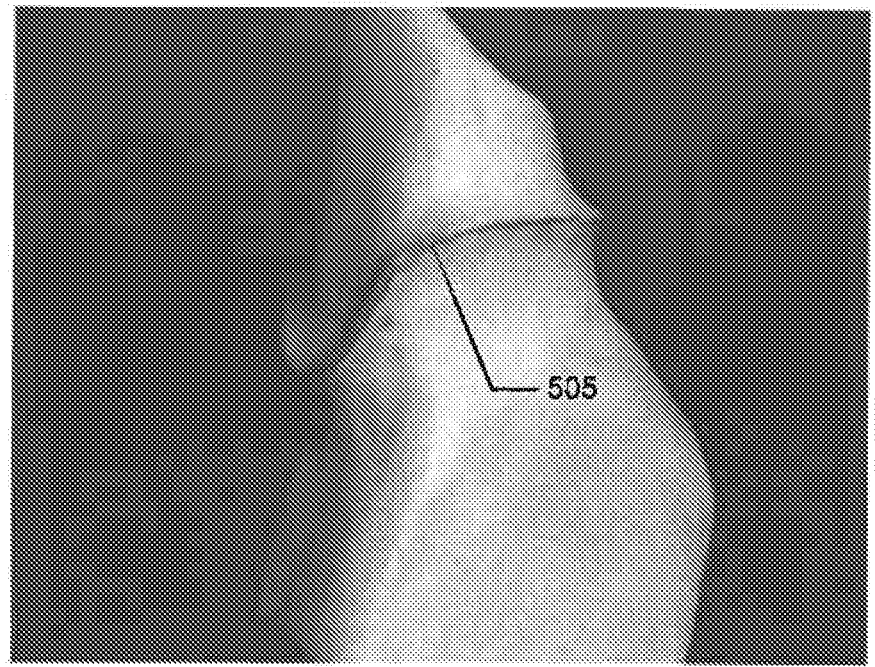
Figure 5G:
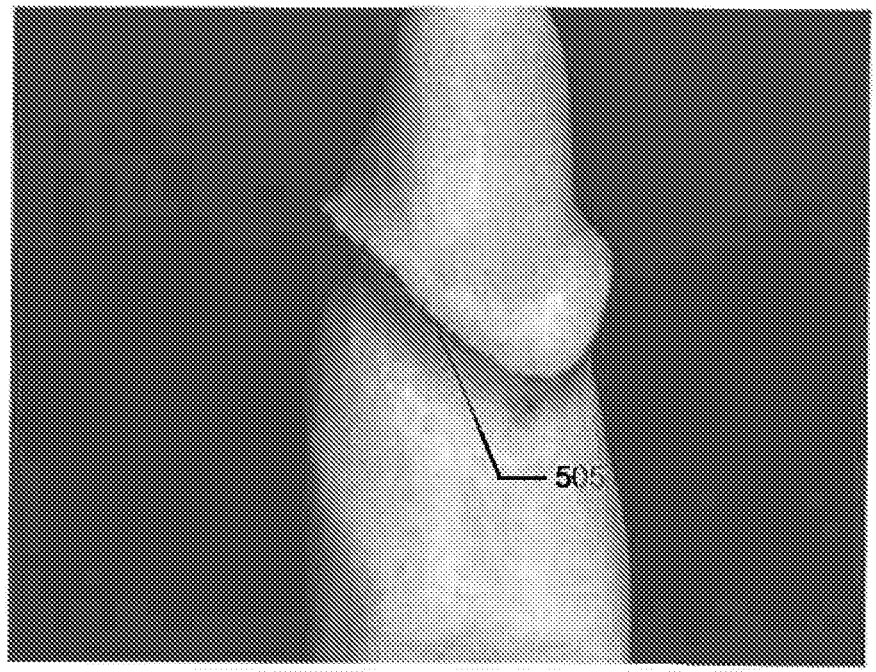
Figure 5H:
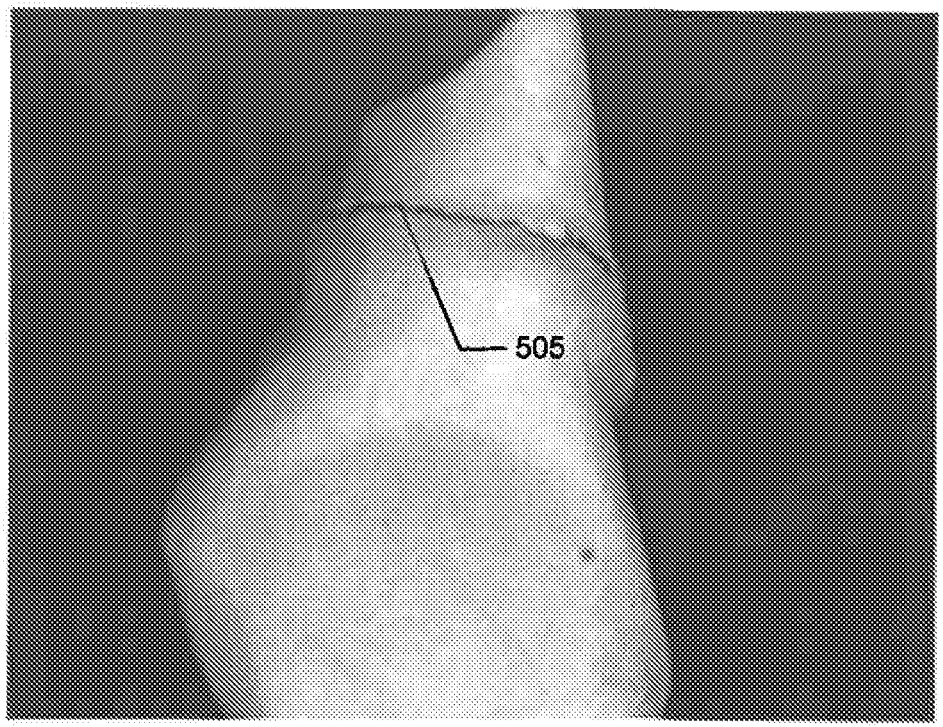
Figure 5I:
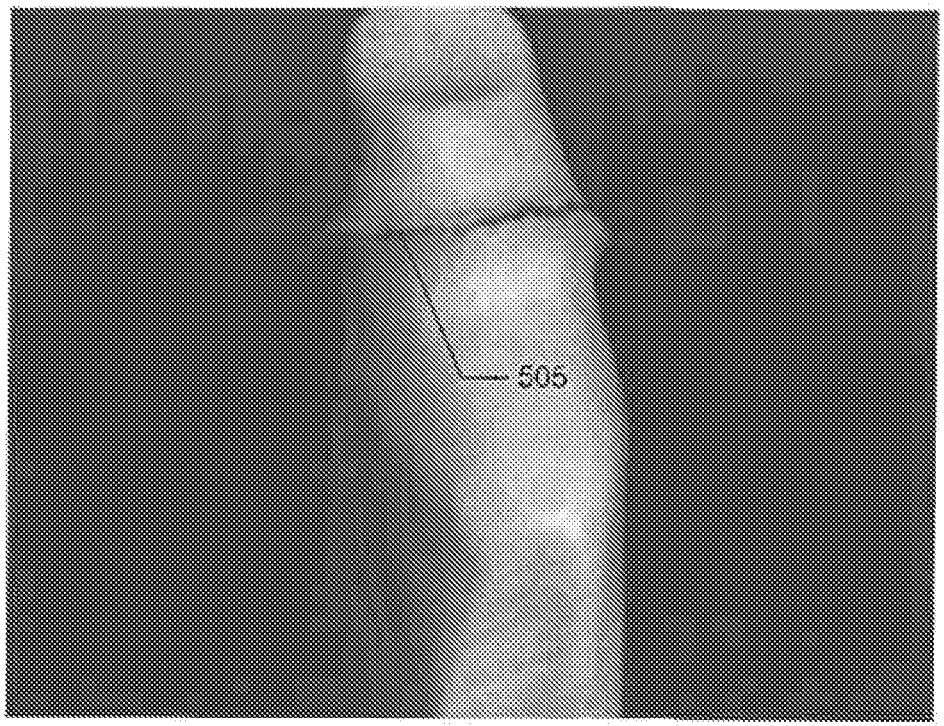

FIGS. 5f)-5i) show a number of texture scans from different viewpoints of another die 502 which has been prepared meaning that it has been grinded such that a restoration, such as a crown, can be placed on the die 502. The preparation of the die 502 provides a preparation margin line 505 which is a feature which can be detected as a geometrical feature and/or as a textural feature when scanning or imaging the tooth 502. The preparation margin line 505 is also sketched or drawn on the die 502 with a color creating contrast to the color of the die and/or the background.

Figure 5J:
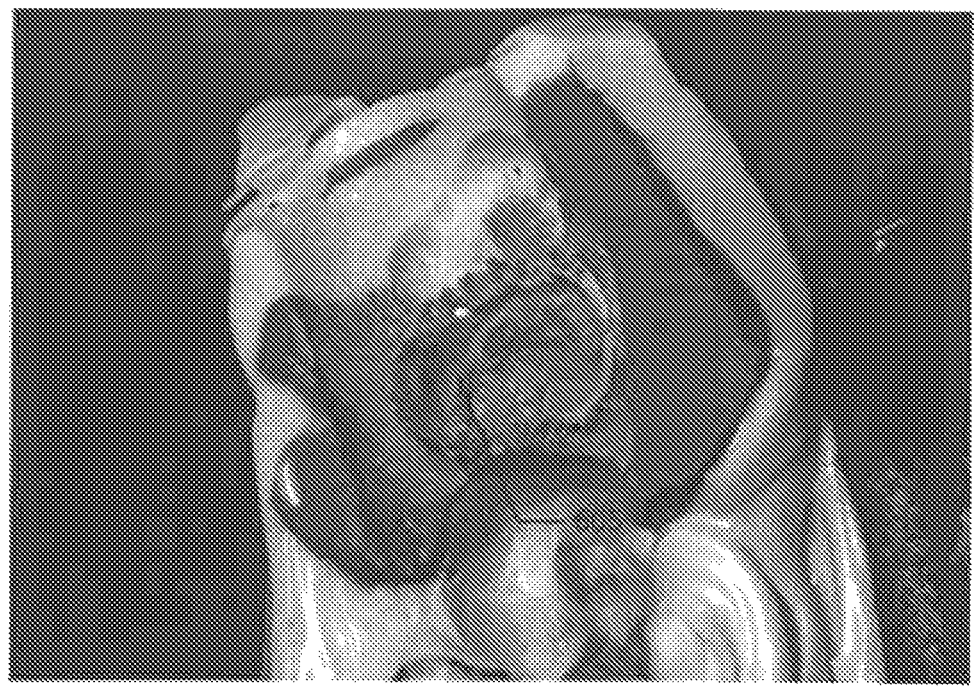
Figure 5K:
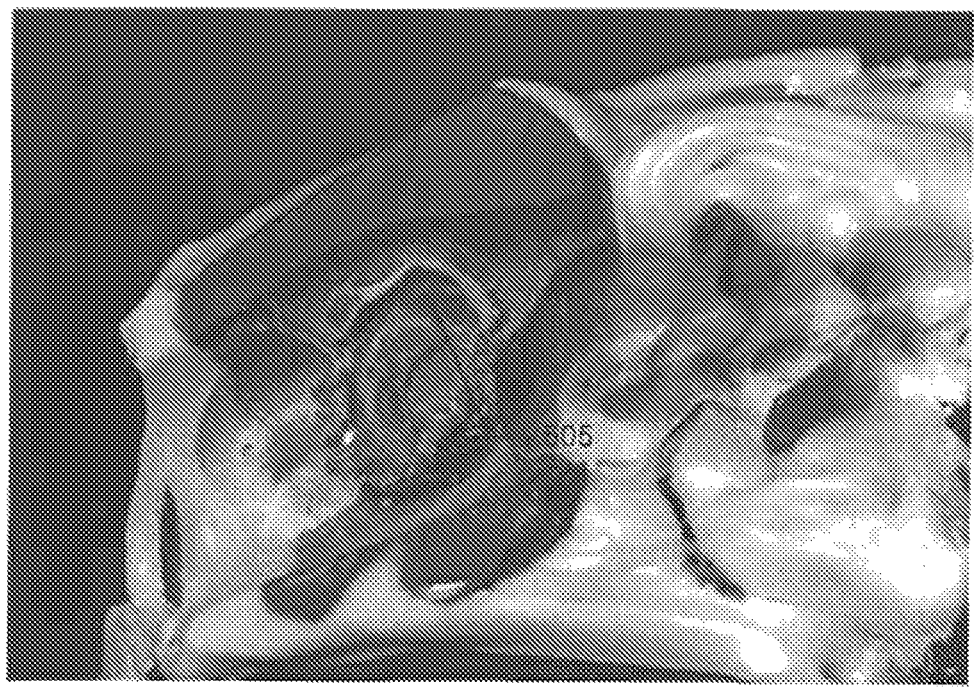
Figure 5L:
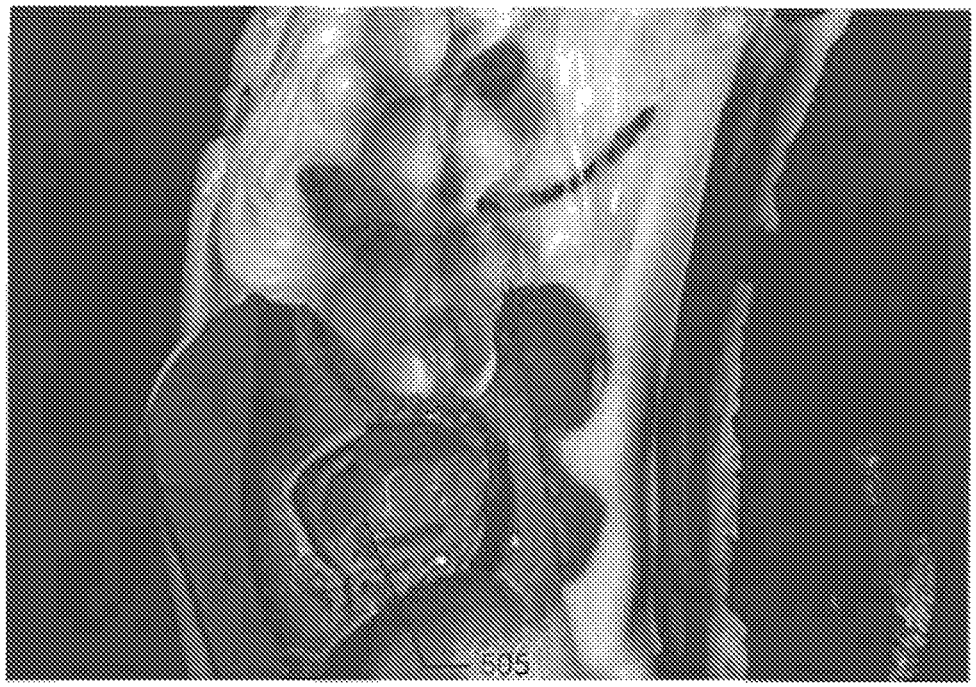
Figure 5M:
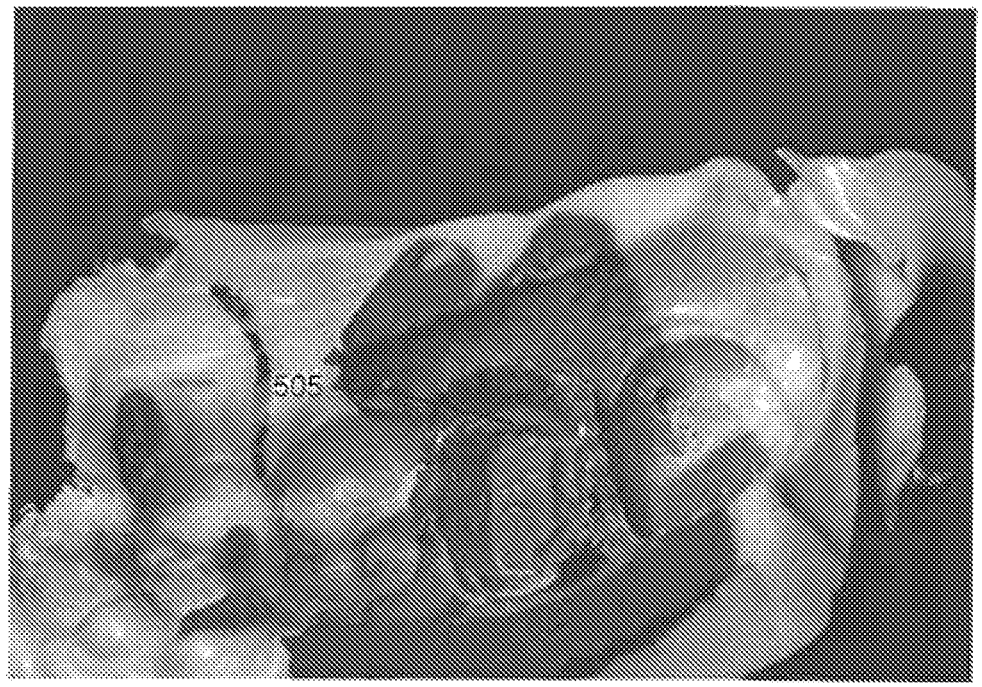

FIGS. 5j)-5m) show a number of texture scans from different viewpoints of an impression of a number of teeth, where one of the teeth is a prepared tooth 502. The impression of the prepared tooth 502 shows the preparation margin line 505 which is a feature which can be detected as a geometrical feature and/or as a textural feature when scanning or imaging the impression of the prepared tooth 502. The preparation margin line can also be sketched or drawn on the impression with a color creating contrast to the color of the impression and/or the background.

FIG. 6 shows an example of texture weaving.

Figure 6A:
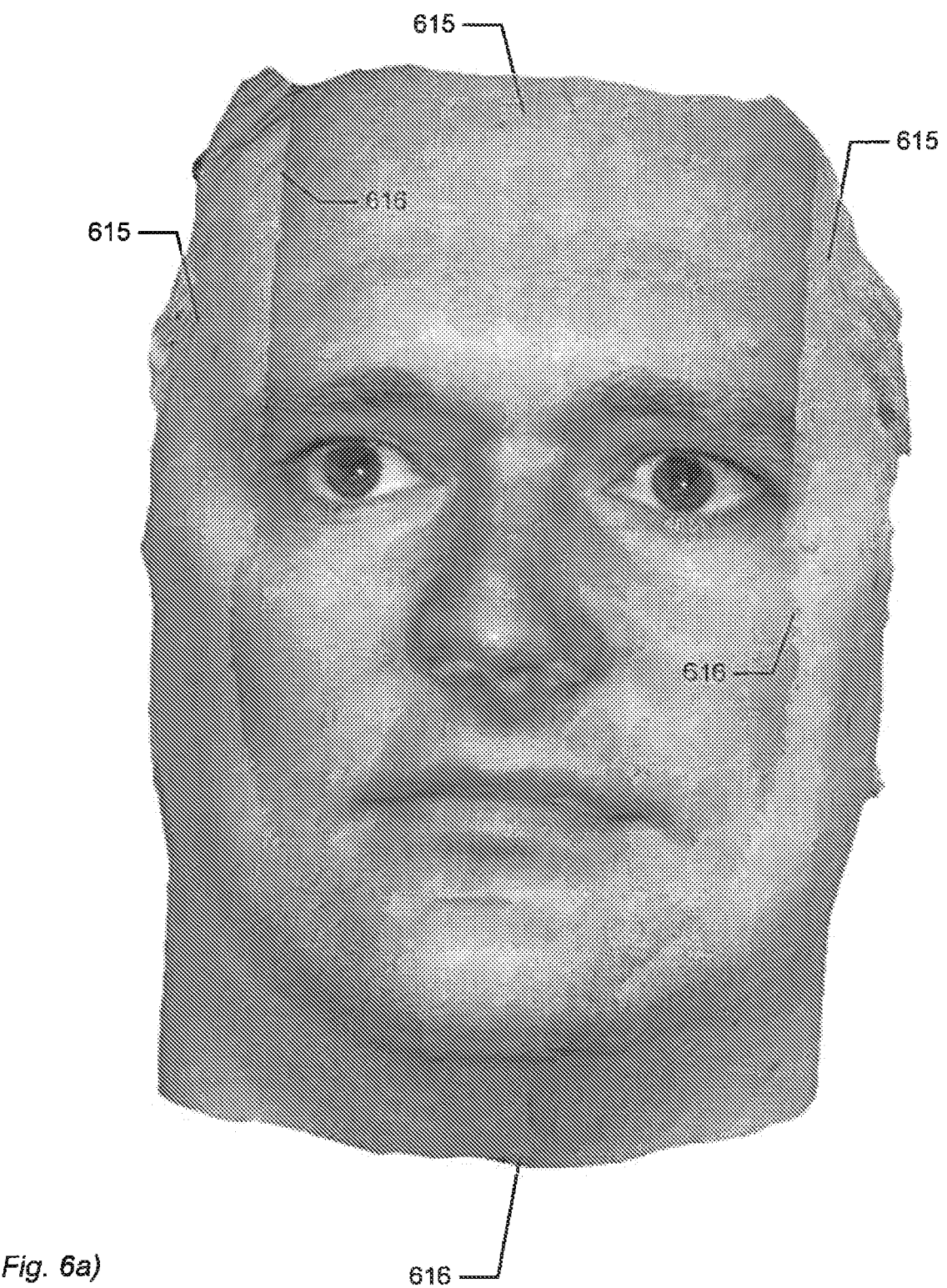
FIGS. 6a to 6b show an example of texture weaving.

FIG. 6a) shows an example where a number, e.g. three, texture images 615 have been acquired of a person's face from different viewpoints, and where the texture images 615 have been assembled into a composite or compound texture image. The transitions 616 between the different texture images 615 can be seen, since the colors or tones are not the same on the borders of the different images 615.

Figure 6B:
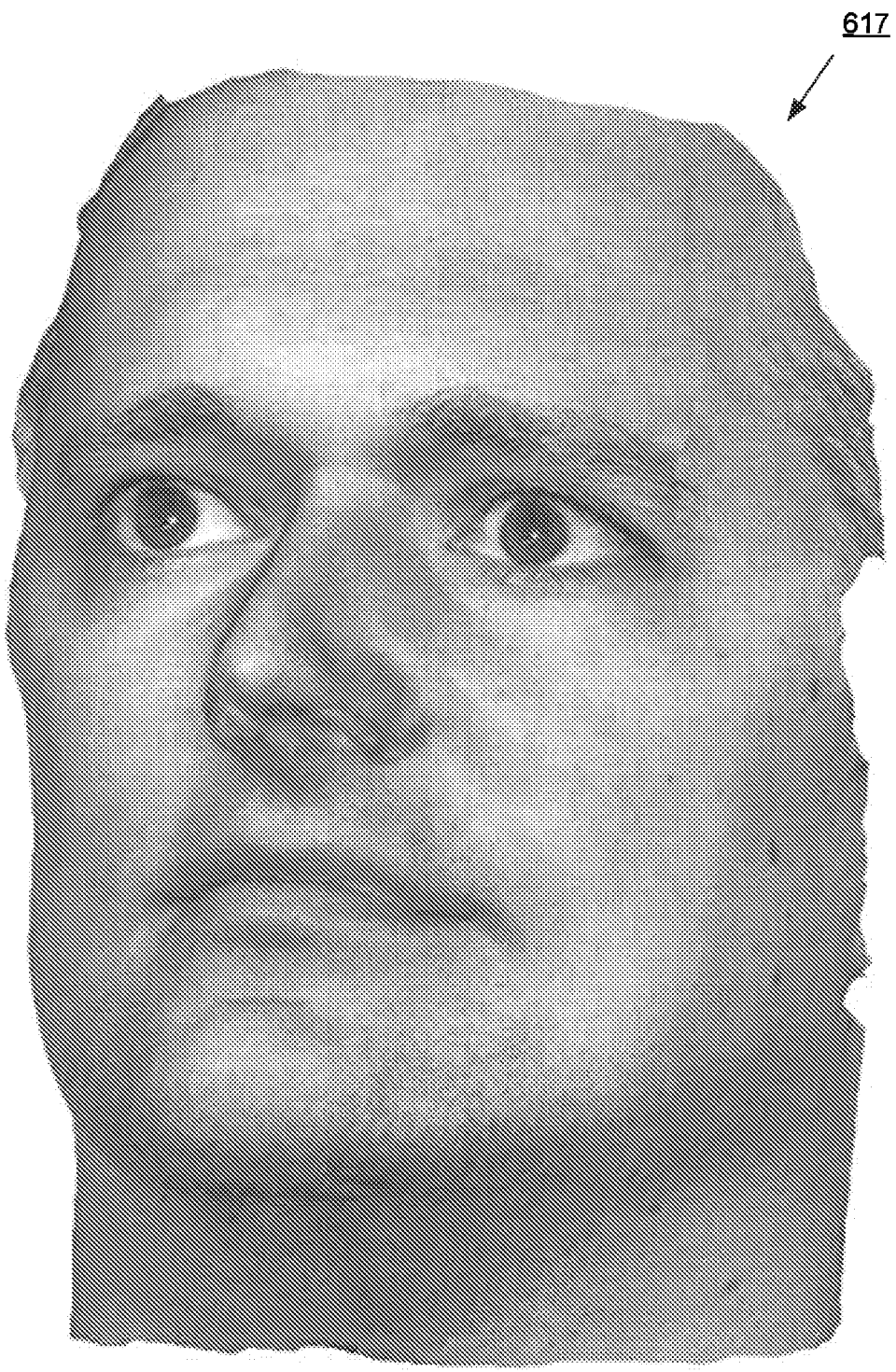

FIG. 6b) shows an example where the single texture images 615 from FIG. 6a) have been subjected to texture weaving, such that the transitions 616 which were dominant in FIG. 6a) cannot or hardly cannot be seen in the final processed texture image 617. The colors and tones of the different texture images 615 have been smoothed out in the final texture image 617 such that the colors and tones match at the borders of the different texture images 615.

Figure 7:
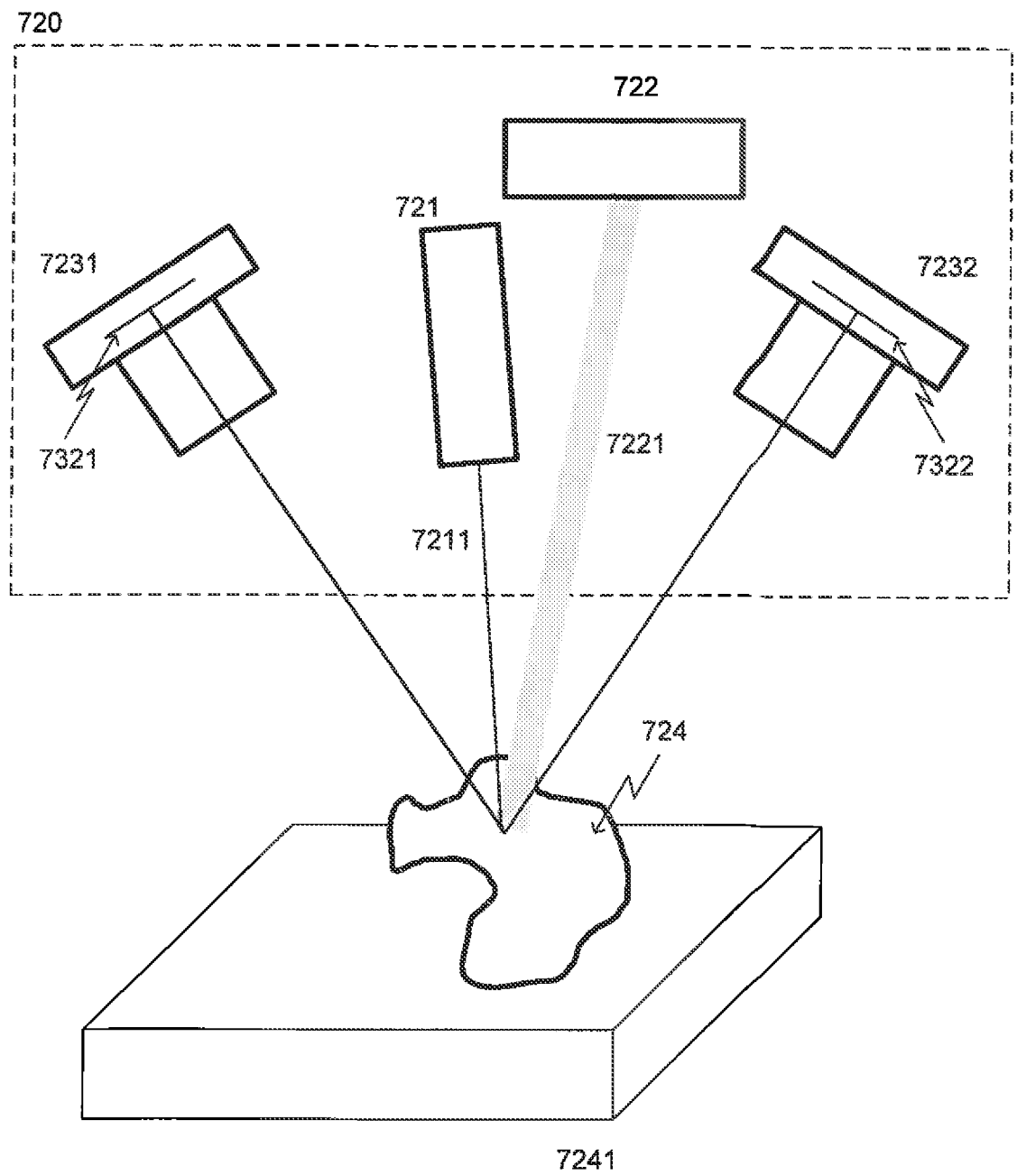
FIG. 7 shows an example of a setup for scanning a location using a first and a Second light source

FIG. 7 shows an example of a setup for scanning a location using a first and a second light source. In this example, the system is configured for acquiring digital representations of a physical model or an impression of the location. In the following, the system is described in relation to a physical model of the location, but the description provided is equally valid for the acquisition of digital representations from an impression of the location.

The optical assembly 720 of the system comprises a first light source 721, a second light source 722 and first set of cameras 7231, 7232. The optical axis of the first light source and the optical axis of the second light source intersects in a scan volume. The scan plate 7241 is arranged such that a physical model 724 placed on this scan plate is within this scan volume and the physical model can be illuminated by light from the first light source 721 and from the second light source 722. The first set of cameras 7231, 7232 are arranged such that their photosensitive elements 7321, 7322 can receive light from the scan volume, such as light reflected from the physical model 724 placed on the scan plate 7241. The system further comprises mechanics, such as a positioning unit (not included in the figure for simplicity) for translating and/or rotating the scan plate 7241 and hence the physical model 724 and the optical assembly 720 relative to each other. The first light source 721 may be a monochromatic laser. The second light source 722 may be broadband light source, such as a white light source, or a light source providing light at multiple distinct wavelengths, such as a light source comprising a number of diodes emitting light at different wavelengths. For some applications, the light emitted from the second light source is preferably diffusive allowing for a detailed detection of the texture of a feature on the physical model, such as e.g. surface roughness at a margin line.

The 3D digital representation comprising geometrical data may be acquired by scanning such a monochrome laser of the first light source 721 over the location 724 while recording the signals reflected from the location to the first set of cameras 7231, 7232.

The system can be used for the steps the method according to the present invention relating to acquiring the 2D digital representation comprising textural data and the 3D digital representations comprising geometrical data The system may be configured such that the 3D digital representations comprising geometrical data is acquired before the 2D digital representation comprising textural data.

Both cameras of the first set of cameras may be used for the acquisition of a 2D image of the 2D digital representation comprising textural data, such that the time used for acquiring a 2D digital representation comprising a large number of the 2D images is reduced. The use of 2D images acquired from both cameras may require a detailed knowledge of the position and orientation of the cameras relative to the location.

A desired coverage of the location may be obtained by acquiring the 2D digital representation comprising texture data and the 3D digital representation comprising geometrical data of the location from a number of different viewpoints. The 3D digital representation may be acquired by collecting individual parts of the 3D digital representation from a number of viewpoints. The individual parts of the 3D digital representation may then be merged to form the 3D digital representation comprising geometrical data of the location. Each individual part may be analyzed to detect a light pattern using a standard tracking algorithm. When the light pattern is known, potentially with sub-pixel precision, the corresponding 3D coordinates can be reconstructed using well-known projective geometry. A precise reconstruction of the 3D coordinates usually requires a high quality of the cameras and light source calibration. Subsequently the 3D coordinates reconstructed from the individual parts relating of the 3D digital representation acquired at the same or at different viewpoints may be merged. The merging may be performed by combining the individual parts taking into consideration their relative position. Finally the 3D coordinates may be triangulated using a standard triangulation algorithm to form the final geometry of the 3D digital representation.

A registration of a part of the 2D digital representation comprising textural data into the 3D digital representation of the location may provide a 3D model comprising textural data. The 2D images of the 2D digital representation comprising textural data may be registered into the 3D model one by one, or the textural data from the one or more 2D digital representations may be combined to provide a 3D models feature which then can be applied to the 3D digital representations comprising geometrical data.

The acquired digital representations may be analyzed in a digital signal processor or microprocessor. The analysis may be performed in real-time.

Figure 8:
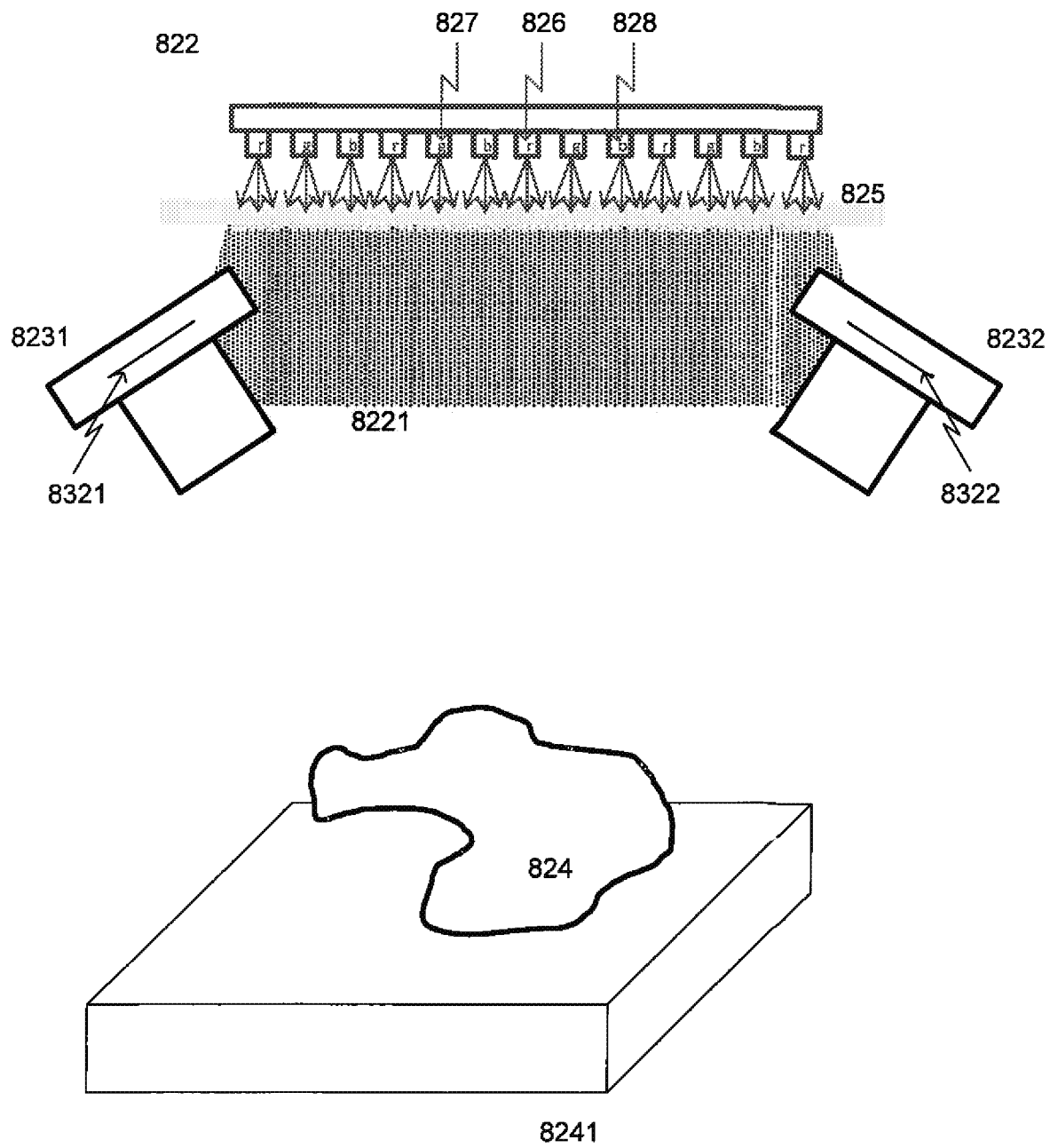
FIGS. 8 to 10 show schematic overviews of some configurations of the second light source that are capable of emitting light with its intensity distributed over a range of wavelengths
Figure 9:
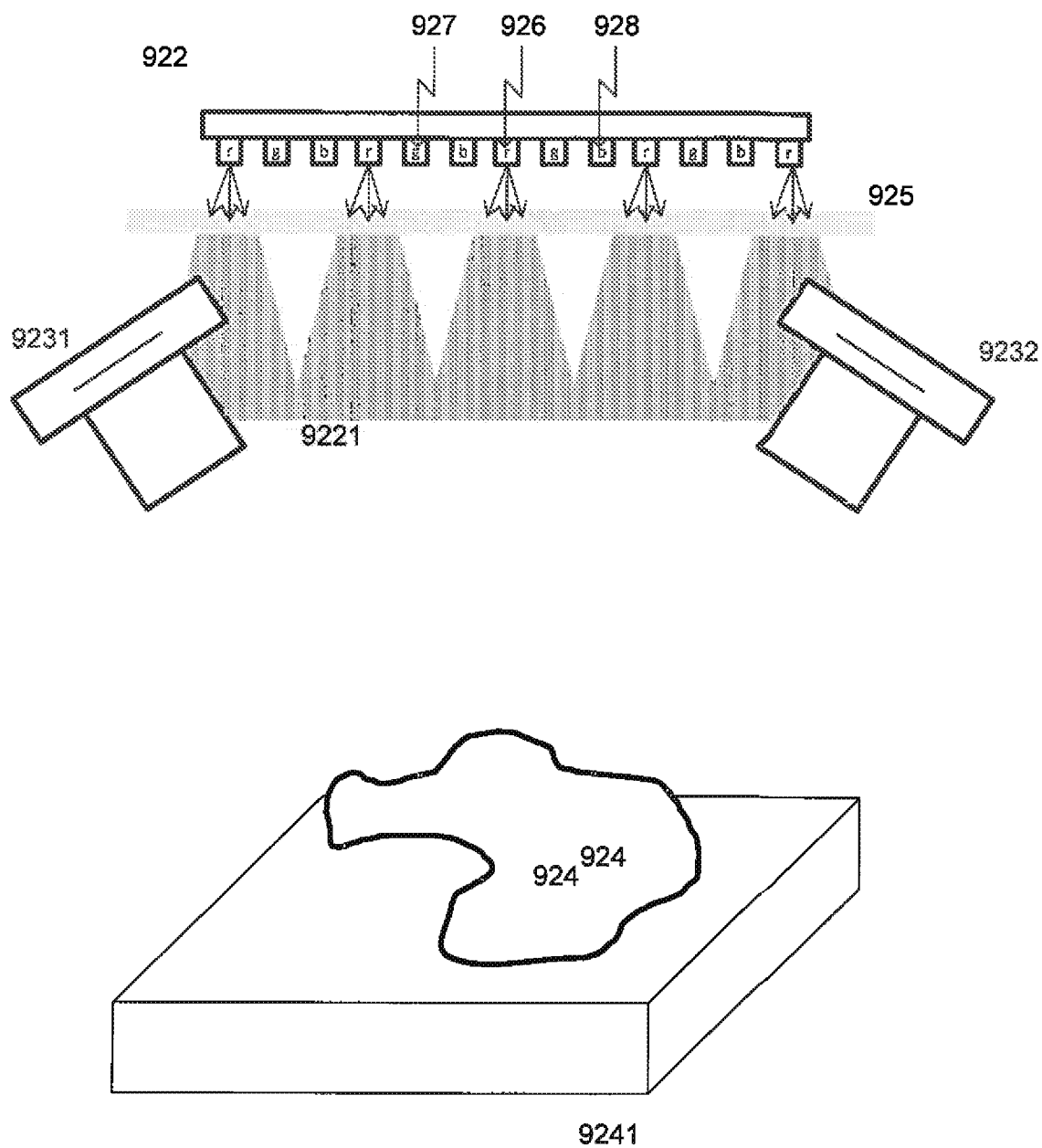
Figure 10:
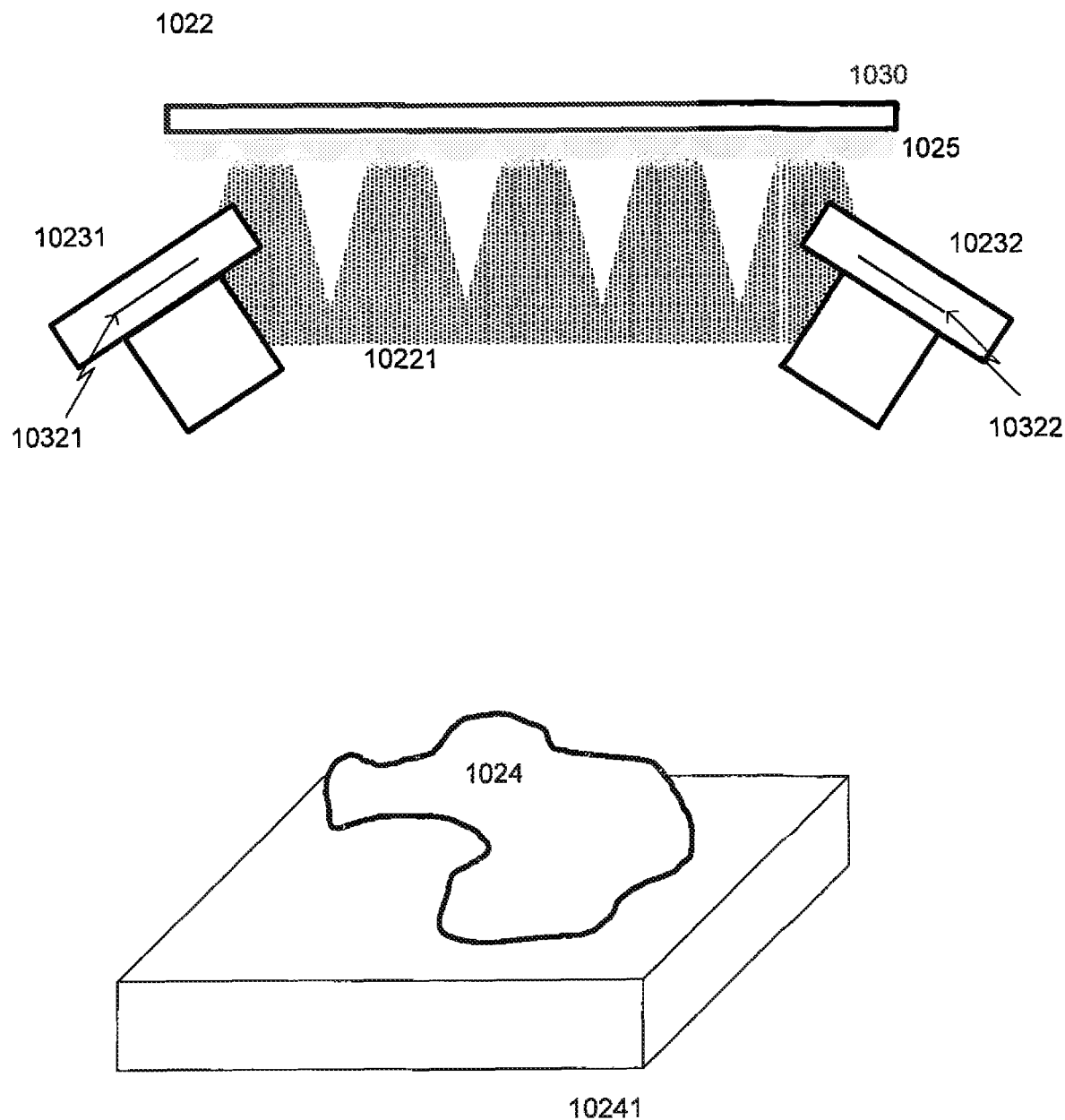

FIGS. 8 to 10 show schematic overviews of some configurations of the second light source that are capable of emitting light with its intensity distributed over a range of wavelengths. Such configurations may be advantageous when the textural data of the features are defined using different colors.

When a feature is defined by e.g. a colored line drawn by a user on a physical model of the location, the feature will only provide a strong reflection of light with a wavelength corresponding to the color of the line. For example, a red line on a physical model only reflects red light and the light emitted from the second light source must include wavelengths in the red range in order to have a reflection from the red line of this feature.

The examples of FIGS. 8 to 10 describe configurations where three colors are used to define different parts of a feature or different feature, but this choice is only for illustrative purposes.

In FIG. 8, the second light source 822 comprises an array of diodes comprising a number of first diodes 826 emitting light with a wavelength in the red range, a number of second diodes 827 emitting light with a wavelength in the green range, and a number of third diodes 828 emitting light with a wavelength in the blue range. A diffuser 825 is arranged to provide a diffusion of the light emitted from the array of diodes such that the physical model 824 arranged on the scan plate 8241 is illuminated by a beam 8221 comprising diffuse light from the second light source. The diffuser can be fabricated from opalized plastic or glass of a few millimeters thickness. All diodes of the array are driven to emit light continuously by a control unit configured for controlling the array of diodes. The control unit is not shown in the figure for simplicity. The control unit can optionally also be configured for controlling the first set of cameras 8231, 8232. The first set of cameras 8231, 8232 are arranged to receive light reflected from the physical model 824 placed on the scan plate 8241.

The cameras 8231, 8232 of the first set of cameras are color cameras such that light at all the wavelengths emitted from the array of diodes can be detected by the camera and identified from the wavelength of the individual signals.

Such a design of the optical assembly is advantageous for acquiring textural data from a physical model on which a first, a second, and a third feature are defined using red, green, and blue color, respectively. The red part of the 2D image acquired by the color cameras relates to the first feature, the green part to the second feature, and the blue part to the third feature. The different parts in each acquired 2D image are hence related to the different features and information for all three features can be derived from one 2D image. Several color 2D images acquired from different relative viewpoints may still be needed in order to obtain the desired coverage.

This arrangement with continuously having light emitted from all three types of diodes, i.e. at all three wavelengths, in the second light source and color cameras in the first set of cameras may have the advantage that each acquired 2D digital representation of the physical model can provide textural data of features defined using the different colors. Acquisition of textural data relating to different features can hence be performed in parallel.

FIG. 9 shows a system where the array of diodes is similar to the array of diodes illustrated in FIG. 8. The diodes of the array are however driven sequentially instead of continuously as described in FIG. 8. The diodes may be driven such that the physical model at any time only is illuminated from one type of the diodes, i.e. illuminated with light at one wavelength only.

The control unit ensures that the first, second and third diodes 926, 927, 928 emits light sequentially, such that the physical model is illuminated by a sequence of light signals, where the sequence e.g. may be first wavelength, second wavelength, third wavelength. The sequence may be repeated a number of times, such as one for each relative arrangement physical model and the second light source and the cameras. The diffuser 925 of the second light source 922 provides that the light in the beam 9221 emerging from the second light source is diffusive.

The acquisition of 2D digital representations using the cameras 9231, 9232 and the driving of the diodes of the second light source 922 is timed such that a 2D digital representation is acquired for every step in the sequence of light signals. A 2D digital representation is hence acquired for each of the wavelengths that is emitted by the array of diodes. Since each of these 2D digital representations is correlated to a single wavelength from the second light source, there is no need for color cameras, and the cameras 9231, 9232 may be monochrome cameras.

A colored line will appear dark grey in a 2D image acquired by the monochrome cameras when the second light source emits light with a wavelength which is outside the wavelength range where this color reflects light. A line having a color which matches a wavelength of the light emitted from the second light source will appear light gray in the acquired 2D image. Standard procedures for processing a grayscale 2D image comprising light grey and dark grey lines can then be applied to identify the color of the drawn lines from their monochrome appearance in 2D digital representations that are acquired while illuminating the physical model with light at the different wavelengths of the second light source.

This arrangement of the second light source and the first set of cameras may have the advantage that a physical model can be scanned using three colors to provide three times the information which can be assessed with one color only, while still using the more simple monochrome cameras. Information relating to three different features from the same physical model of the location may be obtained and distinguished from each other using a monochrome camera.

For the green channel, this approach may double the amount of information, while for the blue and red channels, we have 4 times as much information. Totally, this gives 0.5*2+2*0.25*4=3 times.

The reduced complexity of the scanner when using monochrome cameras may be at the expense of an extended process time since the textural data are acquired sequentially instead of in parallel as seen in FIG. 8.

In FIG. 10, the second light source 1022 comprises a white light source 1030 and a diffuser 1025 arranged to provide a diffusion of the light emitted from the white light source 1030 to provide a diffused light beam 10221. The first set of cameras 10231, 10232 are color cameras.

The white light source 1030 is capable of emitting light over a wavelength range which covers the blue to red wavelengths, such that red, green, and blue color can be used to identify different features on the physical model. The cameras 10231, 10232 may be color cameras, in which case the system only differs from that of FIG. 8 with respect to the second light source.

An alternative to using color cameras, is to use monochrome cameras and place filters, such as Bayer filters in the optical path between the scan volume and the cameras. The Bayer filters then provide a correlation between the position on the photosensitive elements 10321, 10322 where a signal is received and the wavelength of the received signal. Only a number of the pixels of the photosensitive elements 10321, 10322 will receive red light, while others will receive only green light and others will only receive blue light. A calibration wherein the photosensitive elements 10321, 10322 are exposed to monochromatic light sources (red, green, blue) though the Bayer filters establishes the wavelength-pixel correlation, such that the signals detected by the different pixels of the photosensitive elements 10321, 10322 are linked to the different colors of the light reflected by the physical model 1024. The correlation may be stored in the first set of cameras or in a digital signal processor unit used for analysing the 2D digital representations acquired by the first set of cameras.

In FIG. 10, the filters could be arranged between the scan plate 10241 and the photosensitive elements 10321, 10322 of the cameras 10231, 10232.

The white light source 1030 should then preferably be capable of emitting light over a wavelength range which covers the blue to red wavelengths, i.e. the entire wavelength span of the Bayer filter.

This design of the system has the advantage, that the electronics is more simple than that of the design illustrated in FIG. 9 and that the representations can be acquired as fast as in the design of FIG. 8.

Color cameras are often made from a monochrome CCD chip and a Bayer filter arranged in front of this chip.

Figure 11A:
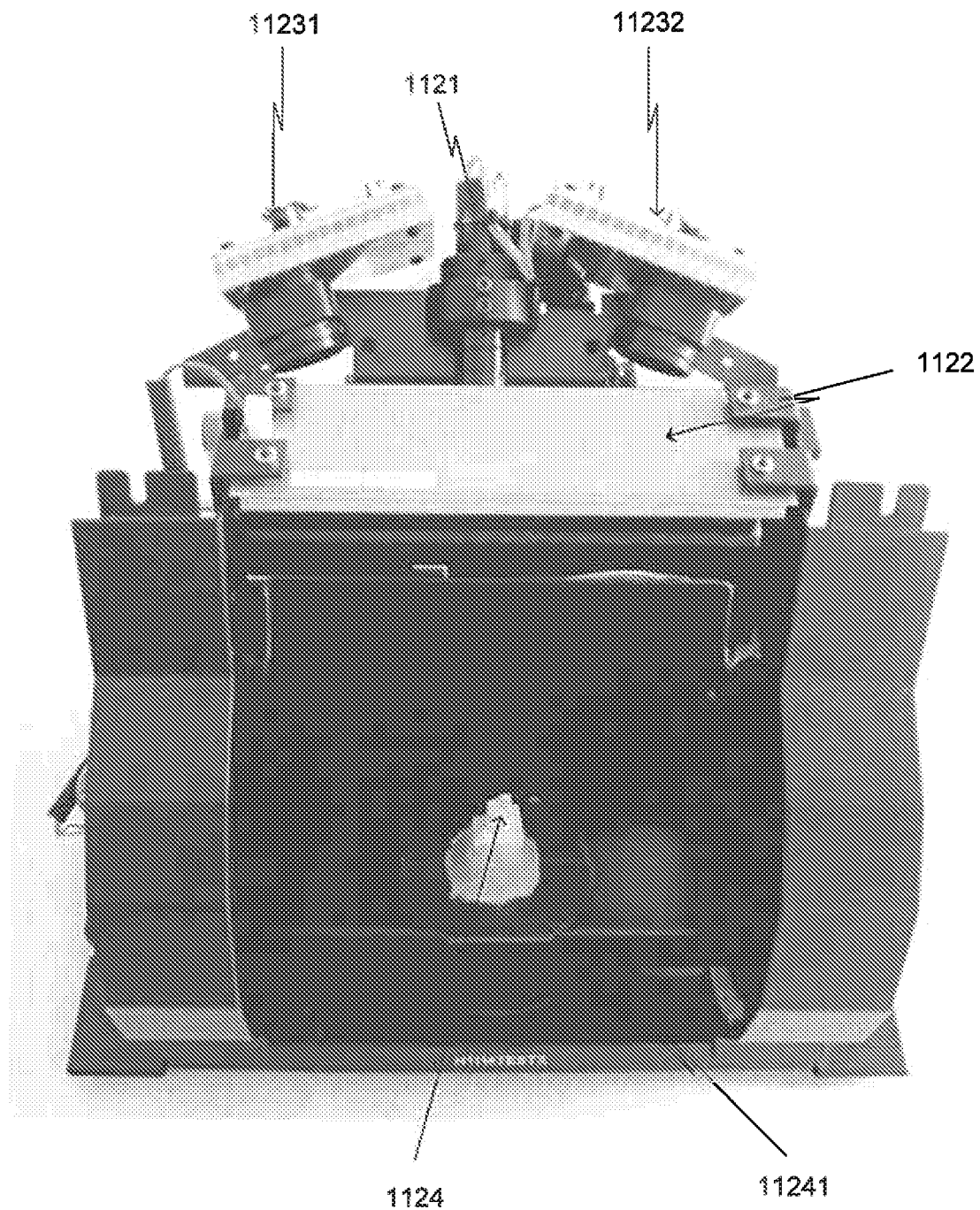
FIGS. 11a to 11b show pictures of the optical assembly of a system according to the present invention.
Figure 11B:
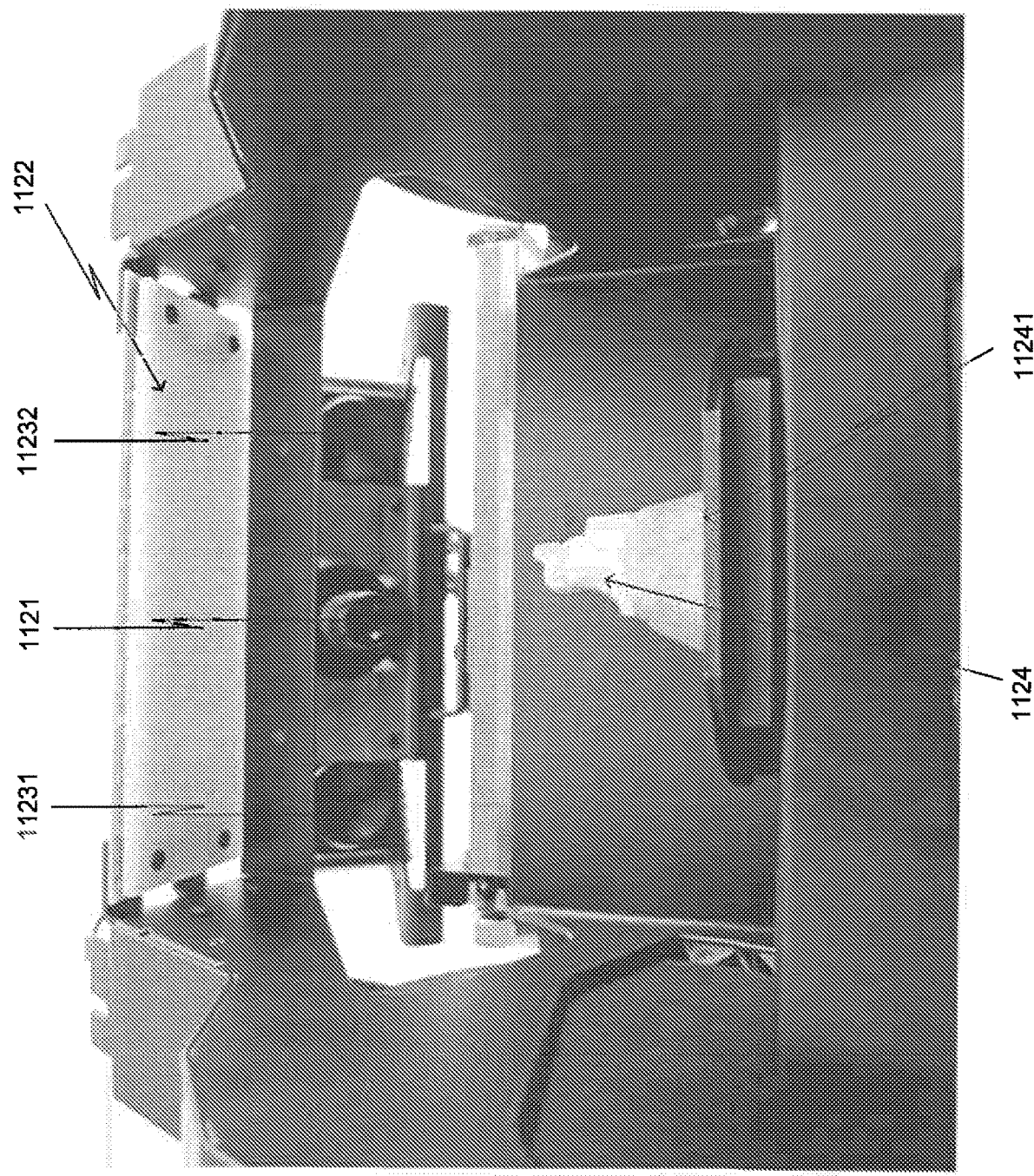

FIG. 11 shows pictures of the optical assembly of a system according to the present invention.

The pictures are taken from different angles and show the components of the optical assembly. The first light source 1121 is a red laser emitting light at a wavelength of 650 nm. The cameras 11231, 11232 of the first set of cameras are arranged at opposite sides of the first light source 1121 to enable a stereo imaging of the surface of a physical model 1124 arranged at the scan plate 11241. The second light source 1122 has a diffuser 1125 arranged to provide that the emitted light is diffuse. Here the 3D digital representation comprising geometrical data and the 2D digital representation comprising textural data are acquired using the first set of cameras 11231, 11232. The first light source 1121 and the second light source 1122 are arranged at a different angles relative to the scan plate 11241 such that light from both light sources can be reflected from a physical model 1124 at the scan plate towards the cameras 11231, 11232.

In one configuration of the optical assembly, the second light source 1122 has diodes that emits light at e.g. red, green and blue wavelengths, where the diodes are driven to emit light sequentially. The cameras 11231, 11232 may then be monochrome cameras.

In one configuration of the optical assembly, the second light source 1122 has diodes that continuously emits white light during the acquisition of the 2D digital representation. The cameras 11231, 11232 may then be color cameras, such that features marked in different colors can be distinguished in the acquired 2D digital representation. The color cameras 11231, 11232 may have color filter arrays (CFA) arranged in a Bayer-type arrangement in front of their photosensitive element. In this case, the spatial resolution provided by light at green wavelengths is twice the spatial resolution provided by light at red and blue wavelengths, such that for some applications it could be preferred to use a green laser instead of a red laser as the first light source 1121.

Figure 12A:
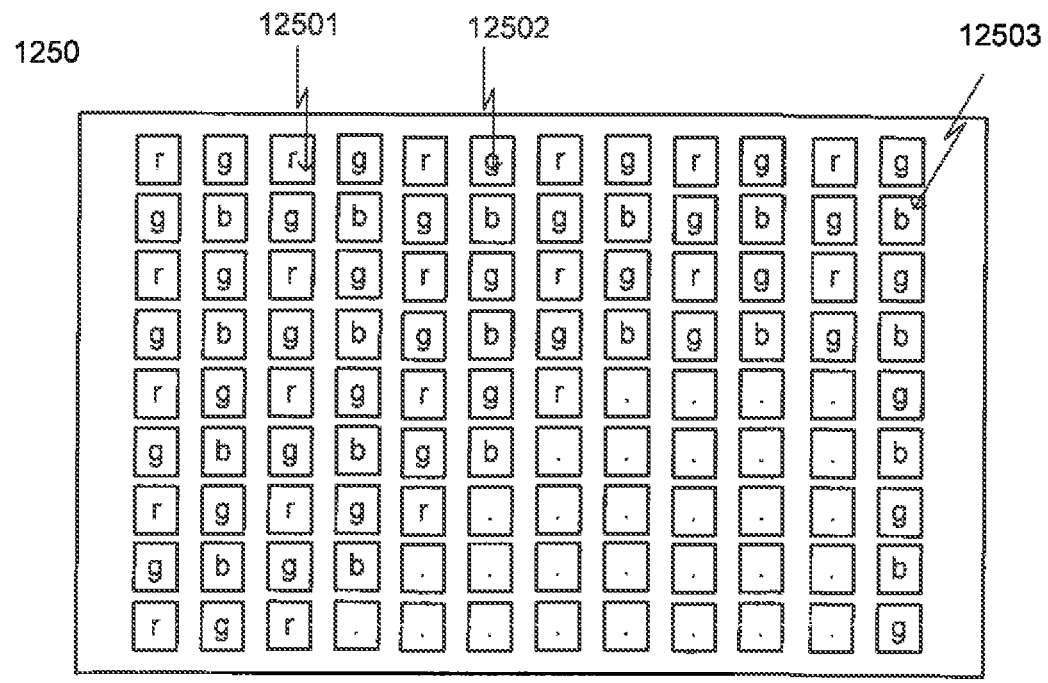
FIGS. 12a to 12b show examples of arrangements of the array of diodes in the second light source.

FIG. 12 shows examples of an arrangement of the array of diodes in the second light source.

Figure 12B:
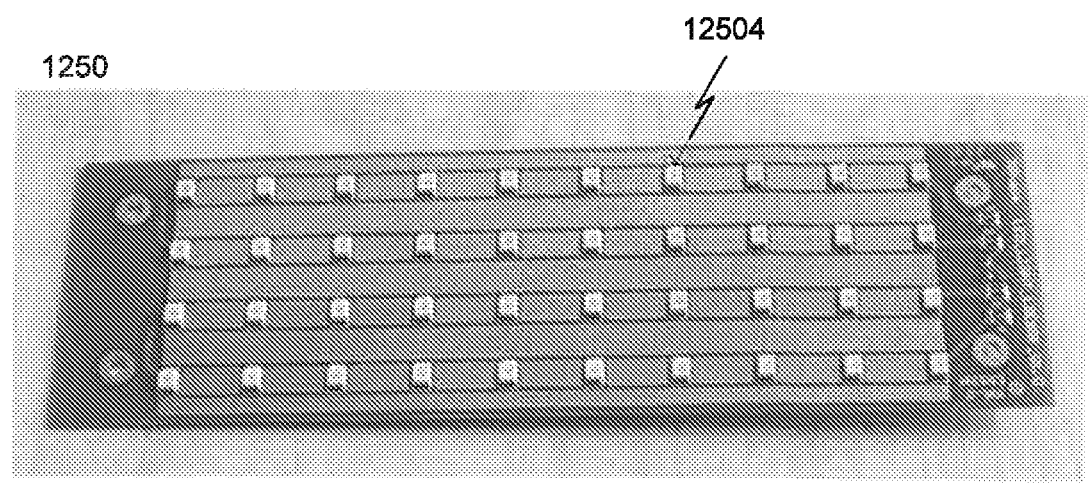

In FIG. 12b is illustrated an arrangement of red diodes 12501, green diodes 12502 and blue diodes 12503 in a 9×12 array on a circuit board 1250 with the red, green and blue diodes arranged similar to the distributions of these colors in a Bayer filter. FIG. 12b shows a picture of a circuit board 1250 of second light source, where the white diodes 12504 are arranged in a 4×10 array.

Figure 13A:
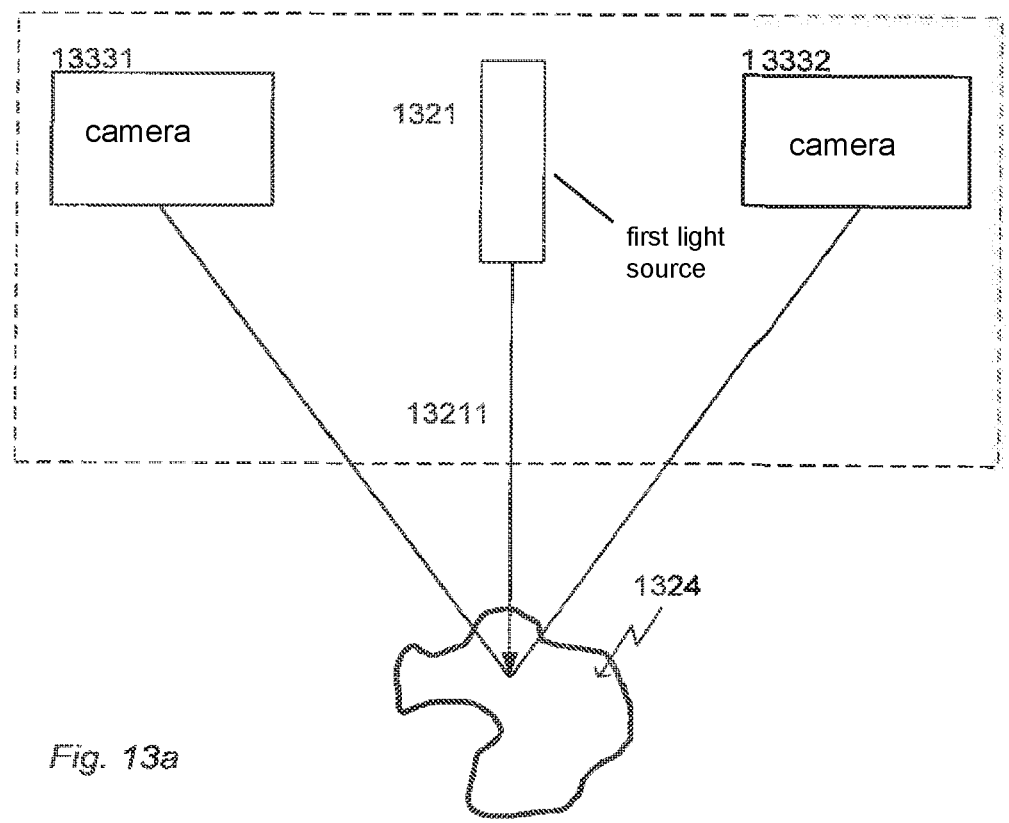
FIGS. 13a to 13b show a schematic of a system using two-photon fluorescence for acquiring a combined 3D digital representation comprising both geometrical data and textural data.
Figure 13B:
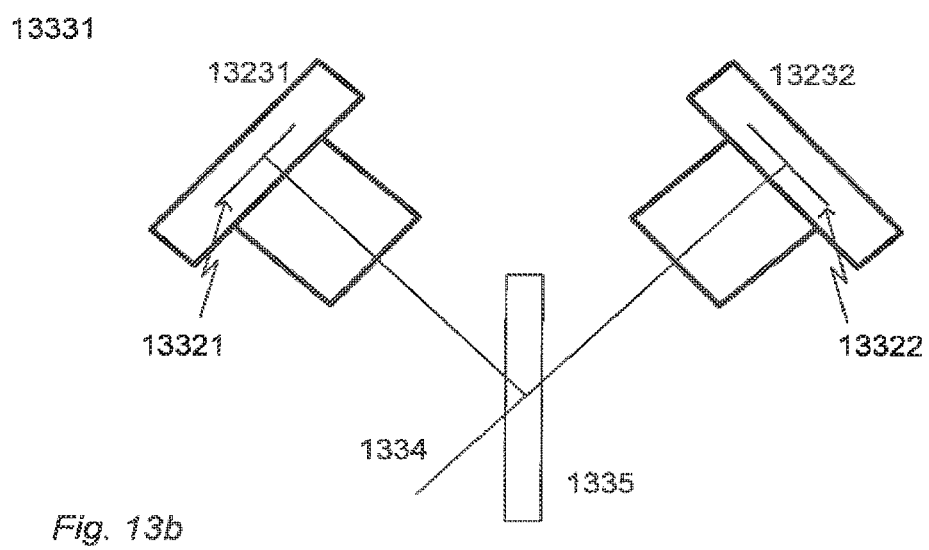

FIG. 13 shows a schematic of a system using two-photon fluorescence for acquiring a combined 3D digital representation comprising both geometrical data and textural data.

A feature is defined on the physical model 1324 of the location using a paint or ink comprising a fluorescent material configured for two-photon excitation and the first light source 1321 emits light at a wavelength in the infrared range. When two infrared photons are absorbed, a photon in the visible range is emitted from the feature.

The 3D representation acquired by detecting the reflected infrared photons from the location can directly be combined with the 3D representation acquired by detecting the fluorescence from the feature.

A feature on comprising a fluorescent material having an excitation band including the wavelength of the first light source 1321 may provide a Stoke shift of the wavelength of the first light source. In contrast, the light reflected from the location maintains its wavelength. Using various optical configurations known to the skilled person it is then possible to extract both the geometrical data and the texture data using only the first light source to illuminate the location.

Since the fluorescence typically is orders of magnitudes weaker than the reflected light it may be advantageous to detect the reflected light using the first set of cameras, while the fluorescence signal is detected using a second set of cameras 13331, 13332. The second set of cameras 13331, 13332 may comprise a filter arranged to block light within the wavelength of the first light source, or filters may be placed between the location and the second set of cameras 13331, 13332.

Several parts of the optical assemblies illustrated in FIGS. 7 to 13 can also be integrated in a handheld scanner, where the change between different relative arrangements of the system and the location (or a model or impression of the location) is obtained by moving the handheld scanner. The integration in a handheld scanner may require that some of the components of the system are reduced in size. In a handheld scanner system, a digital signal processor or a microprocessor configured for analyzing the acquired 2D digital representations may be placed in the scanner handle or in a separate processing box.

Figure 14:
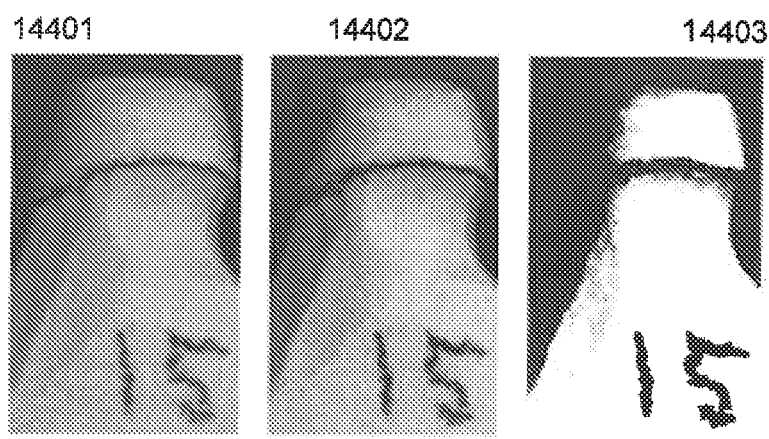
FIG. 14 shows contrast enhancement for 2D images of a physical model of a tooth preparation.

FIG. 14 shows contrast enhancement for 2D images of a physical model of the location.

Figure 15:
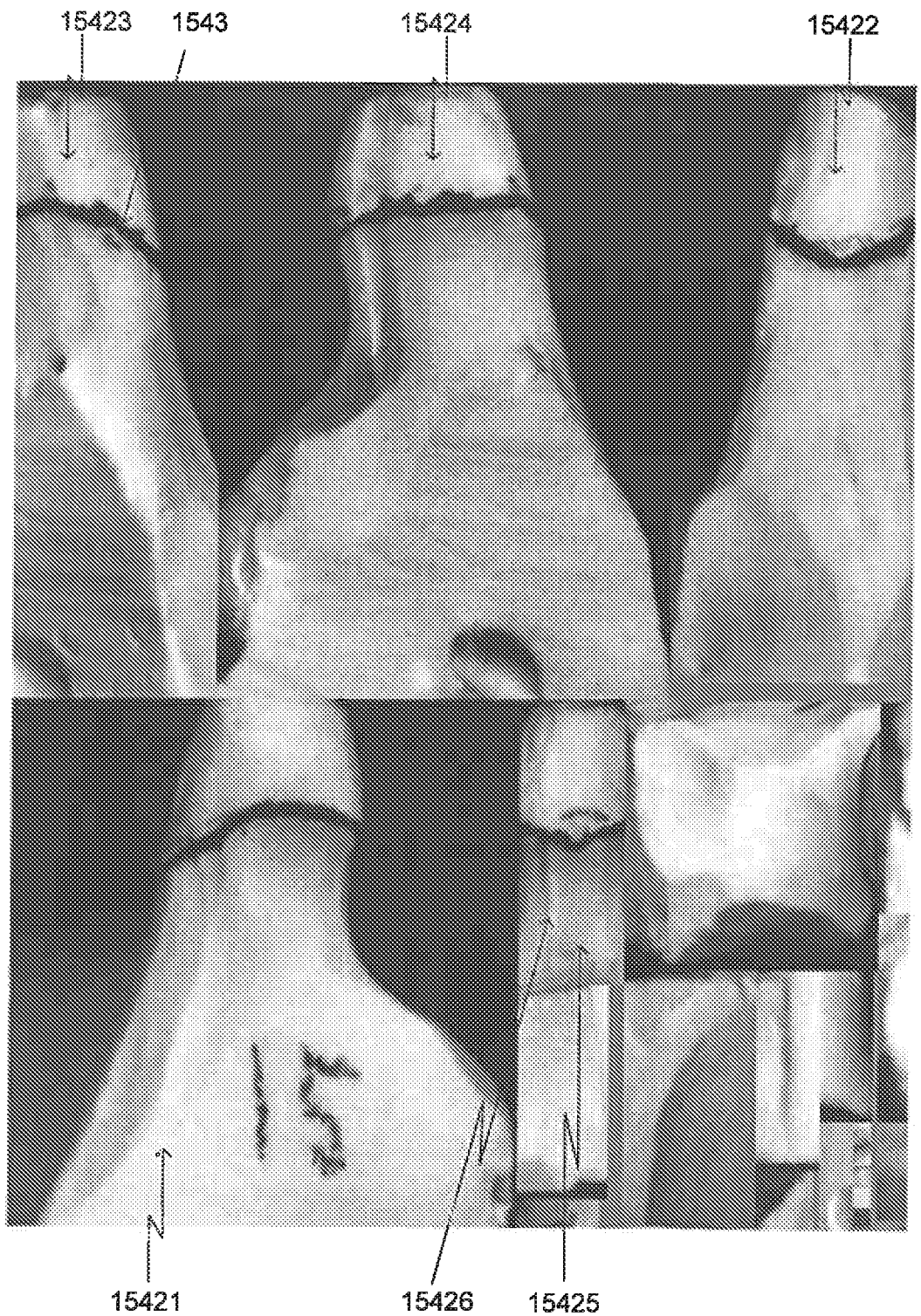
FIG. 15 shows a texture atlas for a physical model of a tooth preparation.

Here the location is a tooth preparation and the 3D object a restoration, such as a crown or a bridge. The physical model is a die of the prepared tooth on which die the margin line has been marked using a pen. Each 2D image of the acquired 2D digital representation is processed to enhance the visibility of the margin line (the feature) before the 2D digital representation is projected onto the 3D digital representation comprising geometrical data. Some image processing may also be performed after this projection. For this physical model, the contrast enhancement appears to be best for alpha values in the range 0.2 to 0.6. When the 3D spline of the margin line has been extracted from the textural data, the restoration is modeled using standard techniques FIG. 15 shows a texture atlas for a physical model of a tooth preparation.

The texture atlas is formed by combining image patches from 2D images acquired of the physical model. The images patches 15421, 15422, 15423, 15424, and 15425 covers the marging line 1543 marked on the physical model using a pencil, with the numbering indicating the order of the 2D images along the margin line.

Texture weaving has been applied to assure that the texture of the image patches is seamless, which e.g. can be seen in 2D image 15425 where the bright elongated section 15426 is due to the somewhat brighter appearance of the neighboring patch 15421.

When projected onto the 3D digital representation, the position of the feature, i.e. the margin line 1543, can be extracted in the form of a 3D spline.

Figure 16:
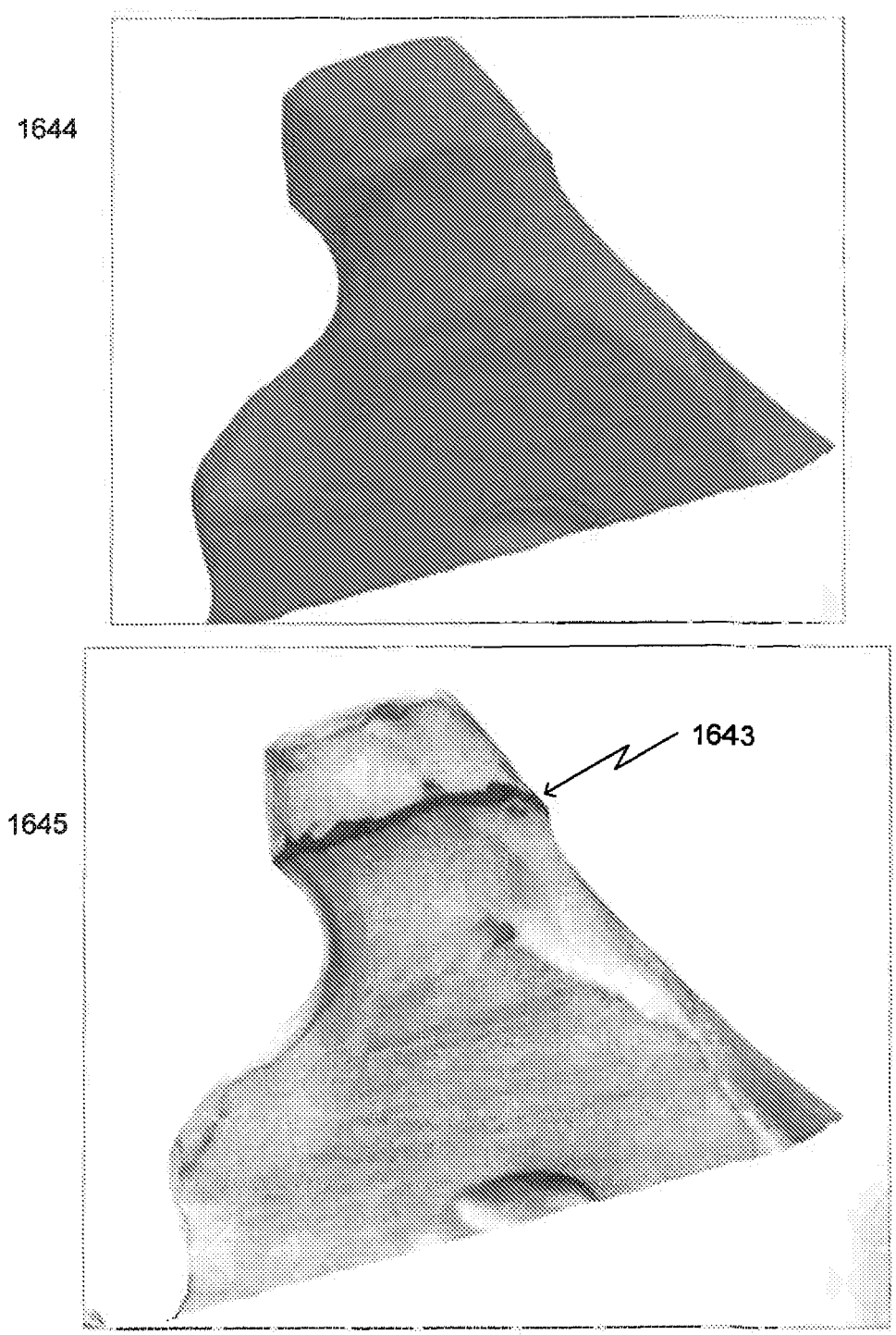
FIGS. 16, 17a and 17b show screen shots from computer software used for implementing the method according to the present invention.

FIG. 16 shows screen shots from computer software used for implementing the method according to the present invention.

The feature is here a margin line drawn on a physical model of a prepared tooth. A 3D digital representation comprising geometrical data 1644 and a combined 3D digital representation comprising geometrical data and textural data 1645 as seen from the same (virtual) position relative to the digital representations. In the combined 3D digital representation where the textural data are projected onto the 3D digital representation comprising geometrical data, the margin line 1643 can be seen. From this combined 3D digital representation, a 3D spline of the margin line can be extracted using computer implemented algorithms.

Figure 17A:
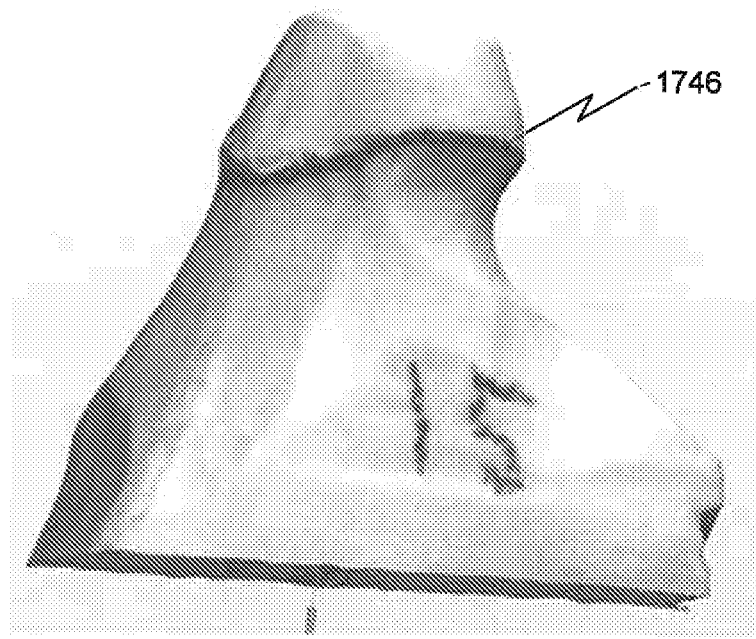

FIG. 17 shows screen shots from computer software used for implementing the method according to the present invention.

This figure shows part of a 3D spline extracted from the textural data of the acquired 2D digital representation. The 3D spline 1746 following the feature of the location, i.e. the margin line, is derived automatically from the texture data of the 2D digital representation by projecting the 2D digital representation onto the 3D digital representation comprising geometrical data.

Figure 17B:
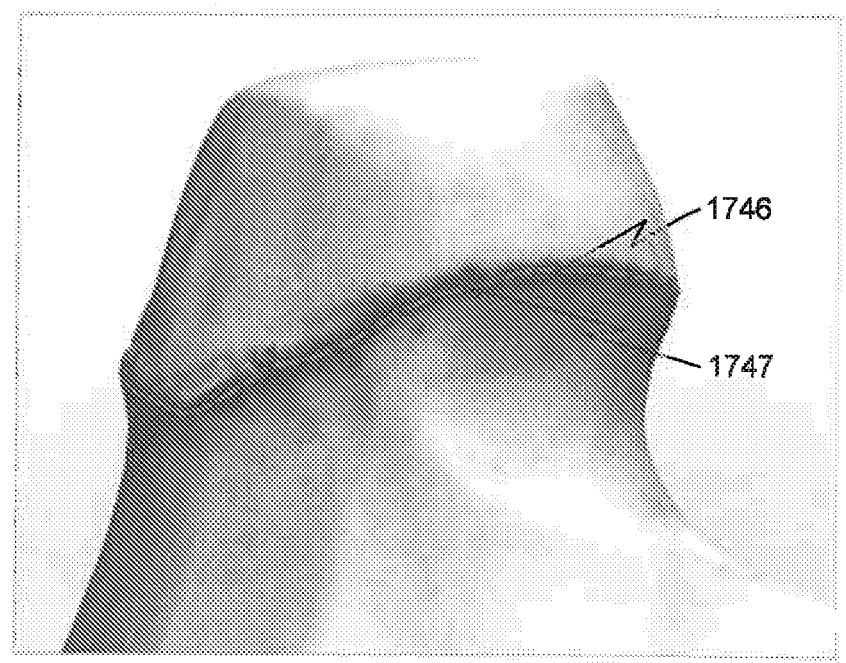

FIG. 17b shows a close-up of the extracted 3D spline 1746 with control points 1747. The form of the 3D spline can be adjusted by moving the control points 1747 relative to the 3D digital representation of the tooth preparation The 3D modeling of the restoration, i.e. of the 3D object, may comprise a defining the surfaces of the restoration based on the 3D digital representation comprising geometrical data and from a target shape of the restoration, while using the 3D spline to define the shape of the restoration in the part facing the marging line.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method for 3D modeling of a dental restoration, wherein the method comprises:
   acquiring a 3D digital representation of at least a part of a location of a patient in which the dental restoration is adapted to be inserted or worn, where the 3D digital representation comprises geometrical data of the location;
   acquiring a 2D digital representation of the at least a part of the location where the dental restoration is adapted to be inserted or worn, where the 2D digital representation comprises information of one or more features of the location, wherein the features are added to the location by an operator, wherein the one or more features include a marking manually drawn on one of the location, on a physical model of the location, or on an impression of the location, by a user prior to the acquisition of the 2D digital representation,
   wherein the marking which is manually drawn is an outline of the dental restoration, or a preparation margin line for a tooth restoration or a partial denture;
   where each of the 2D digital representation and the 3D digital representation includes a representation of the location from one or more different viewpoints relative to the location;
   aligning the 2D digital representation and the 3D digital representation;
   extracting the information of the one or more features from the 2D digital representation;
   combining the extracted information of the one or more features and the 3D digital representation to obtain a combined 3D digital representation comprising both geometrical data of the location and the extracted information of the one or more features;
   visualizing the combined 3D representation; and
   creating a 3D model of the dental restoration based on the combined 3D representation that includes the extracted information of the one or more features, where said 3D model of the dental restoration is created by applying the extracted information of the one or more features.

2. The method according to claim 1, wherein the method comprises translating the one or more features from the 2D digital representation into one or more 3D features.

3. The method according to claim 1, wherein combining the 2D digital representation and the 3D digital representation to obtain a combined 3D digital representation comprises projecting the extracted information from the 2D digital representation onto the 3D digital representation.

4. The method according to claim 1, wherein the 3D digital representation is acquired by scanning a physical model of the location, by scanning an impression of the location, or by performing a direct scanning of the location, wherein the location is one or more teeth of the patient.

5. The method according to claim 1, wherein the 3D modeling comprises defining one or more edges of the dental restoration based on the information.

6. The method according to claim 1, wherein the method comprises providing a 3D model of the dental restoration, and the 3D modeling comprises adapting the provided 3D model of the dental restoration based on the information.

7. The method according to claim 1, wherein extracting information of the one or more features of the location comprises feature detection.

8. The method according to claim 1, wherein the one or more features comprises identification marks arranged within a substantially closed edge of the one or more features.

9. The method according to claim 1, wherein the one or more features comprises a margin line of a prepared tooth or die.

10. The method according to claim 1, wherein the one or more features comprises the shades of the patient's teeth.

11. The method according to claim 1, wherein the dental restoration comprises a removable partial denture, and the one or more features are major connectors, clasps or retention grids, such that the 3D modeling comprises defining one or more edges of the removable partial denture from the 3D feature.

12. The method according to claim 1, wherein the one or more features is a borderline between different structures of the location.

13. The method according to claim 1, wherein the one or more features is a borderline between different materials of the location.

14. The method according to claim 1, wherein at least one of the digital representations is acquired by illuminating at least part of the location, a physical model of the location, or an impression of the location with light, wherein the light used to acquire at least one of the digital representations is multispectral light comprising light at N wavelengths, wherein the number N is equal to or larger than 2, and wherein the method comprises using different colors or color codes to identify different features, where the different colors or color codes correspond to the N wavelengths of the multispectral light.

15. The method according to claim 14, wherein the N wavelengths in the multispectral light are provided in a sequence.

16. The method according to claim 14, wherein the N wavelengths in the multispectral light are provided simultaneously.

17. The method according to claim 14, wherein a 2D image is acquired for each of said N wavelengths and wherein the 2D images acquired for each of the N wavelengths in the multispectral light are stitched together into a common 2D image, such that the 2D digital representation comprises one or more common 2D images, each common 2D image comprising 2D images acquired at each of the N wavelengths.

18. The method according to claim 1, wherein the information of the one or more features is textural data.

19. The method according to claim 1, wherein the information of the one or more features includes a marking drawn on a patient's tooth or a marking drawn on a model of a set of teeth.

20. The method according to claim 1, wherein the information of the one or more features includes a margin line of a tooth prepared for a restoration.

21. A method for 3D modeling of a dental restoration, wherein the method comprises:
   acquiring a 3D digital representation of at least a part of a location of a patient in which the dental restoration is adapted to be inserted or worn, where the 3D digital representation comprises geometrical data of the location;
   acquiring a 2D digital representation of the at least a part of the location where the dental restoration is adapted to be inserted or worn, where the 2D digital representation comprises information of one or more features of the location, wherein the features are added to the location by an operator, wherein the one or more features are manually drawn with different colors by the user on one of the location, on a physical model of the location, or on an impression of the location by a user prior to the acquisition of the 2D digital representation;

where each of the 2D digital representation and the 3D digital representation includes a representation of the location from one or more different viewpoints relative to the location;

aligning the 2D digital representation and the 3D digital representation;

extracting the information of the one or more features from the 2D digital representation;

combining the extracted information of the one or more features and the 3D digital representation to obtain a combined 3D digital representation comprising both geometrical data of the location and the extracted information of the one or more features;

visualizing the combined 3D representation; and creating a 3D model of the dental restoration based on the combined 3D representation that includes the extracted information of the one or more features, where said 3D model of the dental restoration is created by applying the extracted information of the one or more features.

22. The method according to claim 21, wherein the one or more features are manually line-drawn with the different colors.

* * * * *